US011786547B2

(12) United States Patent
Baker et al.

(10) Patent No.: US 11,786,547 B2
(45) Date of Patent: Oct. 17, 2023

(54) METHODS AND COMPOSITIONS FOR DISRUPTING BIOFILM UTILIZING CHITOSAN-DERIVATIVE COMPOUNDS

(71) Applicant: SYNEDGEN, INC., Claremont, CA (US)

(72) Inventors: Shenda M. Baker, Upland, CA (US); William P. Wiesmann, Chevy Chase, MD (US); Stacy Marie Townsend, Rancho Cucamonga, CA (US)

(73) Assignee: SYNEDGEN, INC., Claremont, CA (US)

(*) Notice: Subject to any disclaimer, the term of this patent is extended or adjusted under 35 U.S.C. 154(b) by 0 days.

(21) Appl. No.: 16/572,053

(22) Filed: Sep. 16, 2019

(65) Prior Publication Data
US 2020/0009182 A1    Jan. 9, 2020

Related U.S. Application Data

(63) Continuation of application No. 15/419,436, filed on Jan. 30, 2017, now abandoned, which is a continuation of application No. 13/411,147, filed on Mar. 2, 2012, now abandoned, which is a continuation of application No. PCT/US2010/047758, filed on Sep. 2, 2010.

(60) Provisional application No. 61/239,180, filed on Sep. 2, 2009.

(51) Int. Cl.
*A61K 31/722* (2006.01)
*A61K 9/00* (2006.01)

(52) U.S. Cl.
CPC .......... *A61K 31/722* (2013.01); *A61K 9/0014* (2013.01); *A61K 9/0043* (2013.01); *A61K 9/0053* (2013.01); *Y02A 50/30* (2018.01)

(58) Field of Classification Search
CPC ..... A61K 9/007; A61K 9/0053; A61K 31/722
See application file for complete search history.

(56) References Cited

U.S. PATENT DOCUMENTS

| 8,119,780 B2 | 2/2012 | Baker et al. |
| 8,399,635 B2 | 3/2013 | Baker et al. |
| 8,658,775 B2 | 2/2014 | Baker et al. |
| 8,916,542 B2 | 12/2014 | Baker et al. |
| 9,012,429 B2 | 4/2015 | Baker et al. |
| 9,029,351 B2 | 5/2015 | Baker et al. |
| 9,234,050 B2 | 1/2016 | Baker et al. |
| 9,439,925 B2 | 9/2016 | Baker et al. |
| 9,732,164 B2 | 8/2017 | Baker et al. |
| 2003/0087414 A1 | 5/2003 | Aerts et al. |
| 2003/0181416 A1 | 9/2003 | Comper |
| 2004/0242626 A1 | 12/2004 | Achari et al. |
| 2006/0140911 A1 | 6/2006 | Sharp et al. |
| 2007/0117783 A1 | 5/2007 | Brueck-Scheffler |
| 2007/0281904 A1 | 12/2007 | Baker et al. |
| 2010/0056474 A1* | 3/2010 | Baker ............... A61K 31/722 514/55 |
| 2012/0295355 A1 | 11/2012 | Baker et al. |
| 2012/0301408 A1 | 11/2012 | Baker et al. |
| 2012/0329751 A1 | 12/2012 | Baker et al. |
| 2013/0019860 A1 | 1/2013 | Depla et al. |
| 2013/0210761 A1 | 8/2013 | Baker et al. |
| 2014/0080785 A1 | 3/2014 | Baker et al. |
| 2014/0221308 A1 | 8/2014 | Baker et al. |
| 2014/0234310 A1 | 8/2014 | Shapiro |
| 2015/0031610 A1 | 1/2015 | Baker et al. |
| 2015/0224044 A1 | 8/2015 | Baker et al. |
| 2016/0022564 A1 | 1/2016 | Townsend et al. |
| 2016/0022730 A1 | 1/2016 | Baker et al. |
| 2016/0060362 A1 | 3/2016 | Baker et al. |
| 2017/0119810 A1 | 5/2017 | Baker et al. |
| 2017/0136056 A1 | 5/2017 | Baker et al. |
| 2017/0304355 A1 | 10/2017 | Baker et al. |
| 2020/0009182 A1 | 1/2020 | Baker et al. |
| 2020/0009183 A1 | 1/2020 | Baker et al. |

FOREIGN PATENT DOCUMENTS

| JP | 2009522328 A | 6/2009 |
| JP | 201507617 A | 1/2015 |
| WO | 0036915 A1 | 6/2000 |
| WO | WO-07/077164 A1 | 7/2007 |
| WO | WO-2007/142704 A3 | 5/2008 |
| WO | WO-2008/072230 A1 | 6/2008 |
| WO | WO2008072230 A1 * | 6/2008 |
| WO | WO-08049842 A3 | 9/2008 |

(Continued)

OTHER PUBLICATIONS

Khalil, H. et al., Antimicrobial Agents and Chemotherapy, "Synergy between Polyethylenimine and Different Families of Antibiotics against a Resistant Clinical Isolate of Pseudomonas aeruginosa", 2008, vol. 52, No. 5, pp. 1635-1641 (Year: 2008).*
Sharma et al. "Antibiotics versus biofilm: an emerging battleground in microbial communities", Antimicrobial Resistance and Infection Control (2019) 8:76.
Flemming, et al. "The EPS Matrix: The House of Biofilm Cells", Journal of Bacteriology, Nov. 2007, p. 7945-7947.
Supplementary European Search Report dated Apr. 10, 2013 for EP 10 81 4536.
International Search Report and Written Opinion for International Application No. PCT/US2010/047758, dated Nov. 1, 2010.
Singh, P. K et al., Nature, "Quorum-sensing signals indicate that cystic fibrosis lungs are infected with bacterial biofilms", Oct. 2000, vol. 407, pp. 762-764.
Extended European Search Report for EP application No. 17182792. 6, dated Mar. 2, 2018.

(Continued)

*Primary Examiner* — Bahar Craigo
(74) *Attorney, Agent, or Firm* — GOODWIN PROCTER LLP

(57) ABSTRACT

Described herein are methods of disrupting (e.g., reducing the viscosity of, or dissolving) a preformed biofilm in a subject, the method comprising: administering to the subject an effective amount of a composition comprising a soluble chitosan or derivatized chitosan wherein the soluble chitosan or derivatized chitosan when administered contacts the preformed biofilm, thereby disrupting (e.g., reducing the viscosity of, or dissolving) the preformed biofilm.

18 Claims, 34 Drawing Sheets

(56) References Cited

FOREIGN PATENT DOCUMENTS

| WO | WO-2010056927 A1 | 5/2010 |
|---|---|---|
| WO | WO-2011/028967 A1 | 3/2011 |
| WO | WO-2011028968 A1 | 3/2011 |
| WO | WO-2011028968 A8 | 4/2011 |
| WO | WO-2013134129 A3 | 6/2015 |
| WO | WO-2016/040899 A1 | 3/2016 |
| WO | WO-2016/172595 A1 | 10/2016 |
| WO | 2021/221656 A1 | 11/2021 |
| WO | 2021/222727 A1 | 11/2021 |

OTHER PUBLICATIONS

Full Examination Report for Australian Patent Application No. 2015314755, dated Jan. 29, 2019.
International Search Report and Written Opinion for PCT/US2015/049835, dated Dec. 31, 2015.
Supplementary European Search Report dated Mar. 22, 2018 for EP 15840207.
European Search Opinion dated Mar. 22, 2018 for EP15840207.
Deneuville et al. "Revisited Physicochemical and Transport Properties of Respiratory Mucus in Genotyped Cystic Fibrosis Patients" American Journal of Respiratory Critical Care Medicine. 1997, vol. 156 pp. 166-172.
Actor et al. "Lactoferrin as a Natural Immune Modulator" Curr Pharm Des. 2009, vol. 15, pp. 1956-1973.
Tre-Hardy, et al., "In vitro activity of antibiotic combinations against Pseudomonas aeruginosa biofilm and planktonic cultures", International Journal of Antimicrobial Agents, Elsevier Science, Amsterdam, NL., vol. 31, No. 4; Feb. 14, 2008.
Tin San, et al., "Activity of Chitosans in combination with antibiotics in Pseudomonas aeruginosa" International Journal of Biological Sciences, vol. 5., No. 2, Mar. 1, 2009.
Herrero R, et al. "New insights into the mechanisms of pulmonary edema in acute lung injury." Ann Transl Med 2018;6(2):32. doi: 10.21037/atm.2017.12.18.
Jiang et al. "Regulation of lung injury and repair by Toll-like receptors and hyaluronan" Nature, (2005) pp. 1173-1179.
Pechos RD " With Friends Like These: The Complex Role of Neutrophils in the Progression of Severe Pneumonia", Front. Cell. Infect. Microbiol. 7:160.
Yang S-C et al., "Understanding the role of neutrophils in acute respitory distress syndrome." Biomedical Journal, http://doi.org/10/1016/j.bj.2020.09.001.
Maria Cristina Bonferoni et.al. (2009) Chitosan and its salts for mucosal and transmucosal delivery, Expert Opinion on Drug Delivery, 6:9, 923-939, DOI: 10.1517/17425240903114142.
Narayanswamy et al., (2018) "Novel Glycopolymer Eradicates Antibiotic- and CCCP-Induced Persister Cells in Pseutomonas aeruginosa," Front. Micbrobiol, 9:1724.
Robert C. Read et al. "Effective nasal influenza vaccine delivery using chitosan". Vaccine 23 (2005) 4367-4374.
International Seach Report and Written Opinion issued for PCT/US20/30702, dated Jul. 27, 2020 (8 pages).
International Search Report and Written Opinion issued for PCT/US21/30132, dated Sep. 9, 2021.
Johnson et al., "Nontuberculous mycobacterial pulmonary infections" J Thorac Dis 2014;6(3):210-220.
Henkle et al., "Nontuberculous Mycobacteria Infections in Immunosuppressed Hosts" Clin Chest Med. Mar. 2015; 36(1):91-99.
Narayanaswamy et al., "In Vitro Activity of a Novel Glycopolymer against Biofilms of Burkholderia cepacia Complex Cystic Fibrosis Clinical Isolates" Antimicrobial Agents and Chemotherapy, 2019; 63(6); 1-11.
Fang et al., "Characterization of Burkholderia cepacia complex from cystic fibrosis patients in China and their chitosan susceptibility," World Journal of Microbiology and Biotechnology; 2010; 27, 443-450.
U.S. Appl. No. 17/922,229, Compositions and Methods of Use Thereof, filed Oct. 28, 2022, Pending.
Garcia et al., "Poly (acetyl, arginyl) glucosamine disrupts Pseudomonas aeruginosa biofilms and enhances bacterial clearance in a rat lung infection model", Microbilogy 2022; 168:001121, 12 pages.
Fisher et al., "Persistent bacterial infections and persister cells," Nat. Rev. Microbiol., 2017, 15, pp. 453-464.
U.S. Appl. No. 16/573,559, Compositions and Methods of Use Thereof, filed Sep. 17, 2019, Published US 2020/0009183.

\* cited by examiner $1.0 \times 10^6$ cells/ml $5.0 \times 10^5$ cells/ml

Treatment: 100 ppm chitosan-arginine;
THP-1 human monocytes do not clump;
Time after challenge: 24 hours Salmonella C. perfringens E. coli

GAS

Shigella

S. mutans

PAO1

Chitosan-arginine

Water

METHODS AND COMPOSITIONS FOR DISRUPTING BIOFILM UTILIZING CHITOSAN-DERIVATIVE COMPOUNDS

CROSS REFERENCE TO RELATED APPLICATIONS

The present application is a continuation application of U.S. application Ser. No. 15/419,436 filed Jan. 30, 2017, which is a continuation of U.S. application Ser. No. 13/411,147, filed Mar. 2, 2012, which is a continuation of International Patent Application No. PCT/US2010/047758 filed Sep. 2, 2010, which claims the benefit of U.S. Application No. 61/239,180 filed Sep. 2, 2009; each of the foregoing applications is hereby incorporated by reference in its entirety.

GOVERNMENT SUPPORT

This invention was made with government support under grant number W81-XWH-05-1-0504 awarded by the DoD/Army/MRMC. The government has certain rights in the invention.

FIELD OF THE INVENTION

The invention relates to soluble chitosans or derivatized chitosans and their use to disrupt or dissolve a biofilm in a subject.

BACKGROUND

Microbial populations are present in body cavities including the mouth, ear, nose, throat, sinuses, respiratory tree including the lungs, gastrointestinal tract, skin, or wound. Unbalanced populations of bacteria can cause increases in particular microbial populations that are no longer controlled or in balance with the body. These conditions can occur through e.g., pathogenic infections, compromised immune system, and side effects from antibiotics. Pathogenic bacteria can adhere to a host or a surface, colonizing it to form biofilms.

SUMMARY OF THE INVENTION

Compositions comprising soluble chitosans and derivatized chitosans (e.g., liquid, solid particulate and semisolid compositions) and related methods of use are described herein. In these embodiments, the derivatized chitosans are water soluble. Exemplary methods using the compositions described herein include, for example, methods of disrupting preformed biofilm in a subject; methods of preventing or delaying the time to the formation of biofilm in the mouth, ear, nose, throat, sinuses, eyes, respiratory system, and/or digestive tract of a subject; methods of treating or preventing complications of cystic fibrosis in a subject; methods of treating or preventing pulmonary infections in a subject; methods of treating or preventing gastrointestinal tract infections in a subject; and methods of treating a wound, e.g., treating or preventing wound infection in a subject. In some embodiments, a composition described herein can result in the clumping of bacteria, for example, to a chitosan derivative. The clumped bacteria can be discarded, for example, expirated or expectorated by a subject, or can be ingested.

In one aspect, the invention features a method of disrupting (e.g., reducing the viscosity of, or dissolving) a preformed biofilm in a subject, the method comprising: administering to the subject an effective amount of a composition comprising a soluble derivatized chitosan wherein the soluble derivatized chitosan when administered contacts the preformed biofilm, thereby disrupting (e.g., reducing the viscosity of, or dissolving) the preformed biofilm.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the composition.

In one embodiment, the viscosity (e.g., apparent viscosity) of the biofilm is reduced by at least 1, 2, 5, 10, 50, 100, 200, 500, or 1000 fold, compared to the biofilm that has not been contacted with the composition.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the composition.

In one embodiment, the method further comprises administering an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same composition or dosage form).

In one embodiment, the method further comprises administering an antibiotic, anti-inflammatory, or mucolytic (expectorant) compound to a subject in conjunction with, prior to or subsequent to the administration of the composition.

In one embodiment, the antibiotic, anti-inflammatory, or mucolytic (expectorant) compound is administered in a dosage to achieve a synergistic effect.

In one embodiment, the biofilm is in the respiratory system (e.g., airways, lung, throat, nose), ear, mouth (e.g., tooth, tongue, mucosal surface), digestive system (e.g., stomach, small intestine, large intestine, colon, bowel), skin, or wound.

In one embodiment, the subject has a complication of cystic fibrosis (e.g., lung infection or respiratory congestion), pneumonia, oral disease (e.g., gingivitis, dental caries, or halitosis), ear infection, throat infection, sinusitis, a complication in immunocompromised patient (e.g., lung infection or respiratory congestion), gastrointestinal infection, enteritis, or a symptom thereof.

In one embodiment, the subject is infected with bacteria listed in Table 1, 2, 3, or 4.

In one embodiment, the composition is administered topically, orally, or enterally.

In one embodiment, the composition is administered by inhalation (e.g., nebulizer, nasal spray, nasal swab, or sinus spray).

In one embodiment, the effective amount is therapeutically effective amount.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in wounds or duodenum.

In one embodiment, the derivatized chitosan is soluble in aqueous solution from about pH 2.0 to about pH 4.0, e.g., in stomach.

In one embodiment, the derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

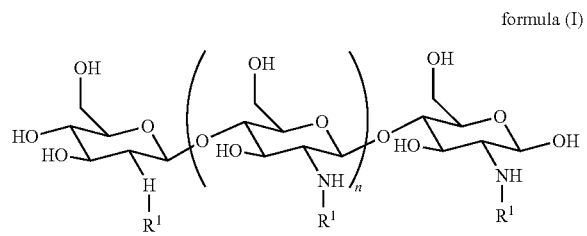

formula (I)

wherein:

n is an integer between 20 and 6000; and each $R^1$ is independently selected for each occurrence from hydrogen, acetyl, and a group of formula (II):

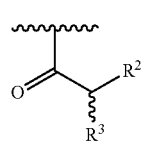

formula (II)

or R1, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

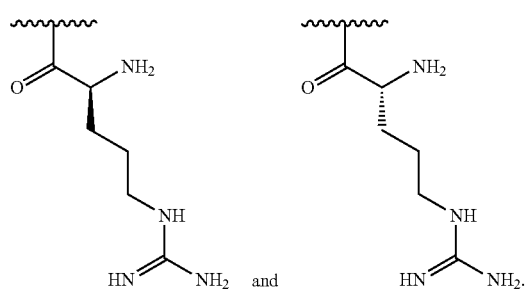

In one embodiment, $R^2$ is amino and $R^3$ is a lysine side chain.

In one embodiment, $R^1$ is selected from one of the following:

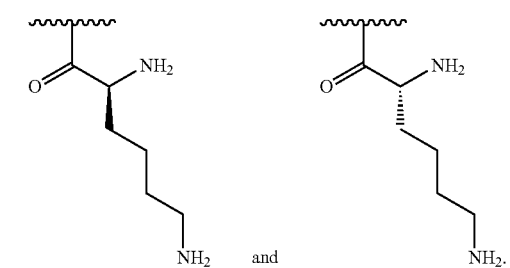 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

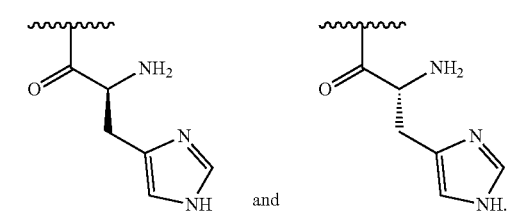 [SMILES: *C(=O)[C@@H](N)Cc1c[nH]cn1 ; *C(=O)[C@H](N)Cc1c[nH]cn1]

In one embodiment, at least 1% of $R^1$ substituents are selected from one of the following:

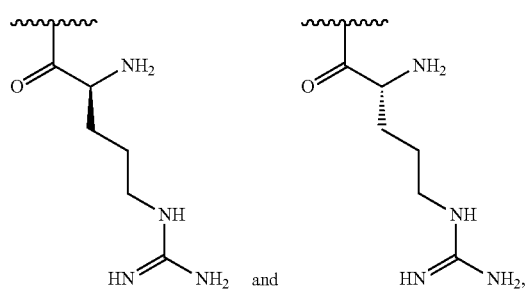 [SMILES: *C(=O)[C@@H](N)CCCNC(=N)N ; *C(=O)[C@H](N)CCCNC(=N)N]

AND at least 1% of $R^1$ substituents are selected from the following:

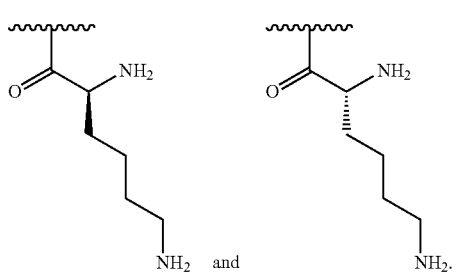 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

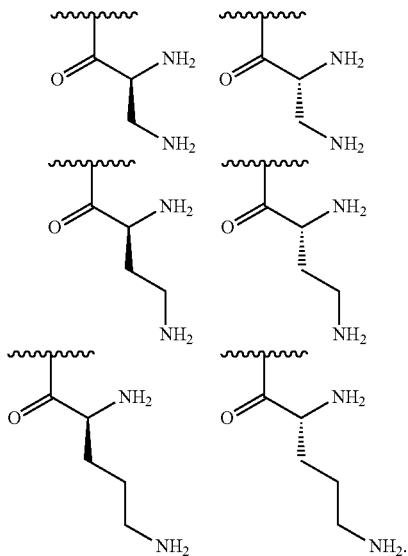

In one embodiment, R is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

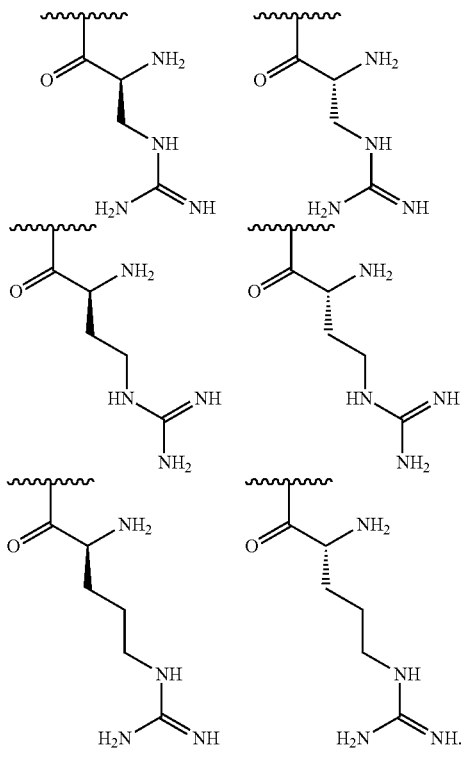

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^1$ is selected from one of the following:

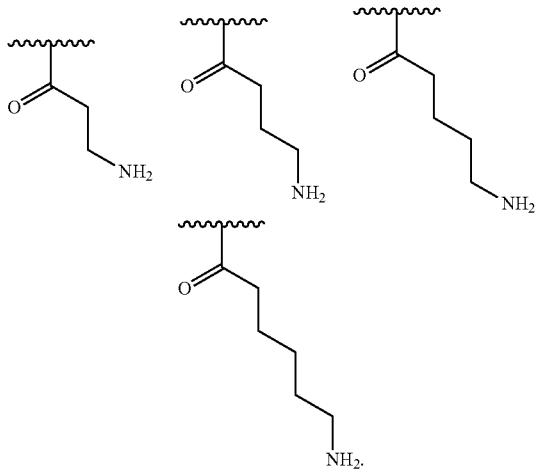

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

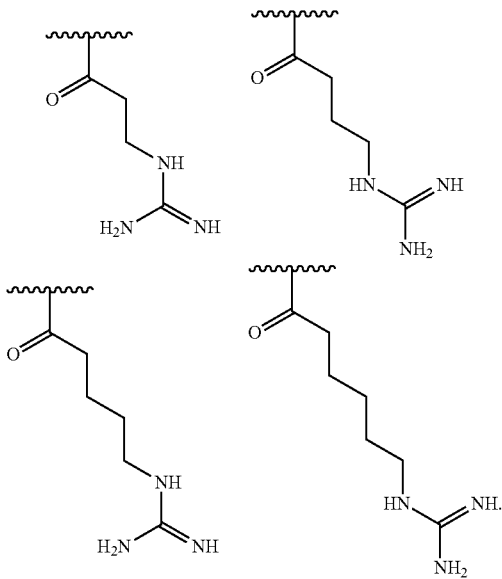

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the functionalized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a method of preventing (e.g., reducing the degree of) the formation of a biofilm in the respiratory system of a subject, the method comprising: administering to the respiratory system of the subject an effective amount of a composition comprising a soluble derivatized chitosan, thereby preventing or treating the formation of a biofilm in the respiratory system of the subject.

In one embodiment, the method further comprises administering an additional agent, e.g., a pharmaceutical agent, or a non-pharmaceutical agent (e.g., a non-toxic surfactant).

In one embodiment, the second agent is administered in a dosage to achieve a synergistic effect.

In one embodiment, the method further comprises administering an antibiotic, anti-inflammatory, or mucolytic (expectorant) compound to a subject in conjunction with or subsequent to the administration of the composition.

In one embodiment, the method further comprises administering an antibiotic, anti-inflammatory, or mucolytic (expectorant) compound to a subject in conjunction with, prior to or subsequent to the administration of the composition.

In one embodiment, the subject is infected with planktonic bacteria or infected with bacteria listed in Table 3.

In one embodiment, the subject is diagnosed with bacterial pneumonia.

In one embodiment, the composition reduces the viability of planktonic bacteria.

In one embodiment, the composition reduces colonization of the planktonic bacteria.

In one embodiment, the composition is administered by inhalation (e.g., nebulizer, nasal spray, or sinus spray).

In one embodiment, the effective amount is therapeutically effective amount.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan comprises a chitosan of the following formula (I):

formula (I)

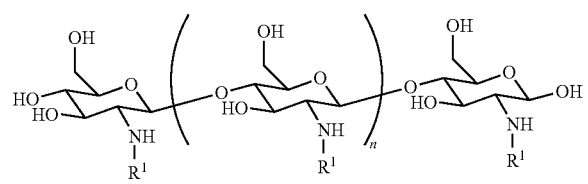

wherein:
n is an integer between 20 and 6000; and
each $R^1$ is independently selected for each occurrence from hydrogen, acetyl, and a group of formula (II):

formula (II)

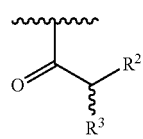

or R1, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

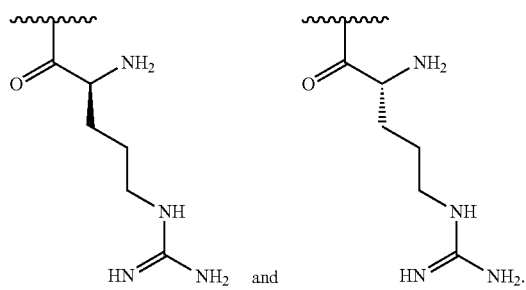 [SMILES: *C(=O)[C@@H](N)CCCNC(=N)N ; *C(=O)[C@H](N)CCCNC(=N)N]

In one embodiment, $R^2$ is amino and $R^3$ is a lysine side chain.

In one embodiment, $R^1$ is selected from one of the following:

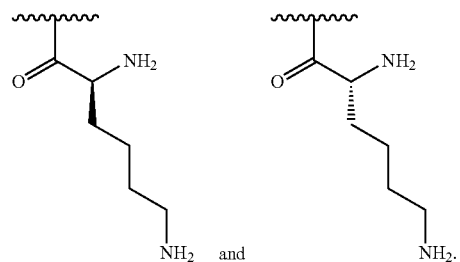 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

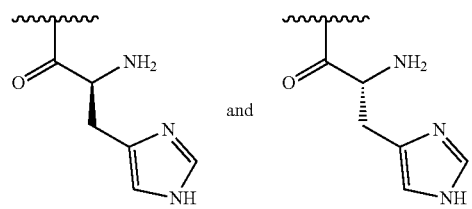

In one embodiment, at least 1% of $R^1$ substituents are selected from one of the following:

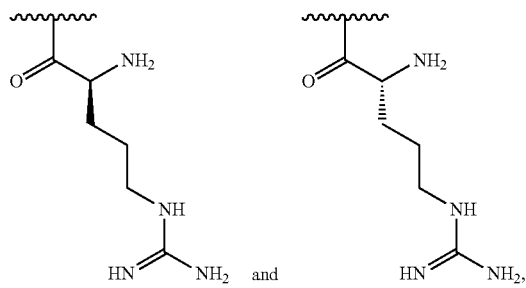

and at least 1% of $R^1$ substituents are selected from the following:

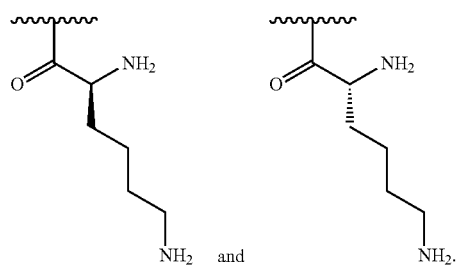 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

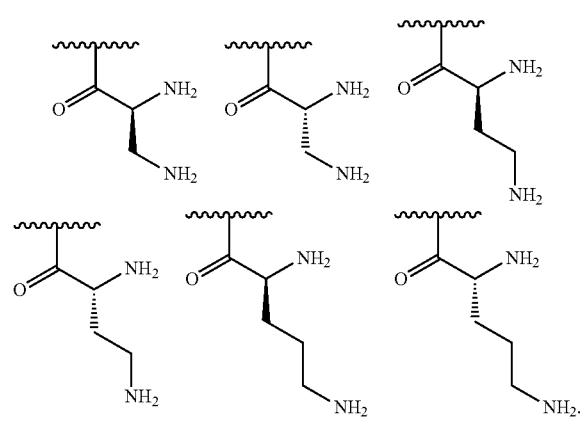

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

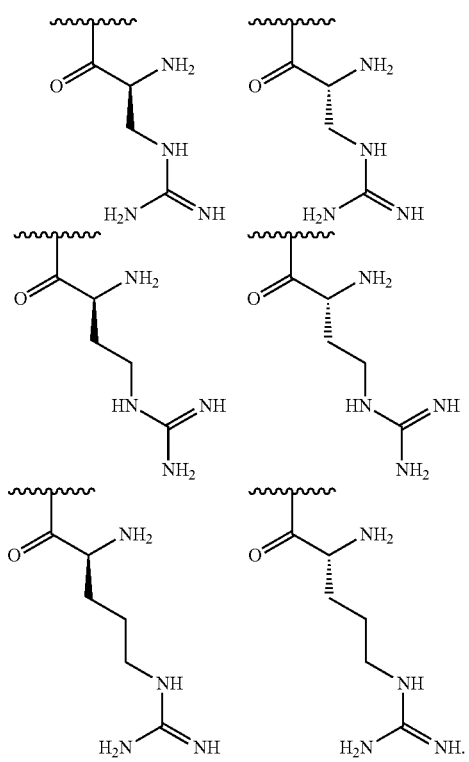

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

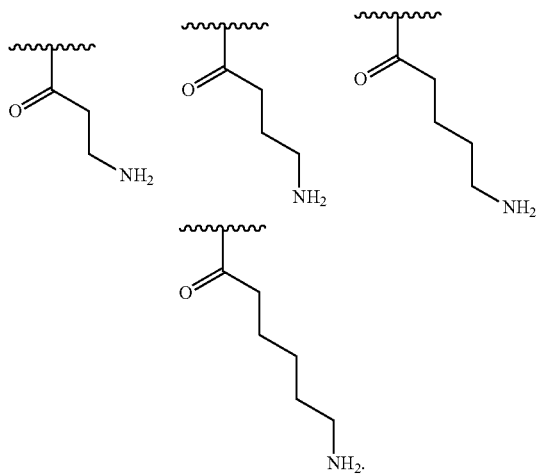

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

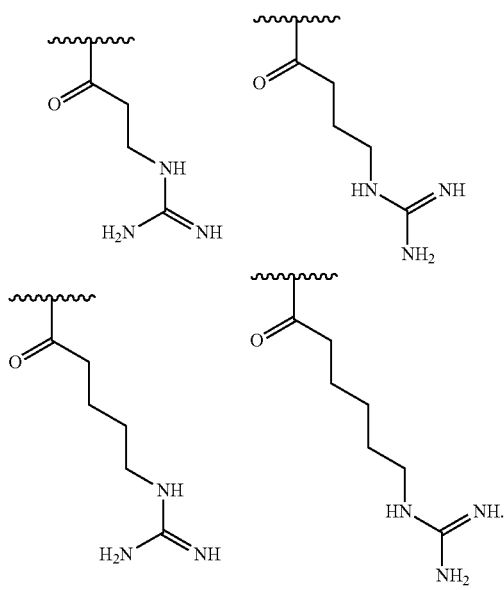

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a method of preventing (e.g., reducing the degree of) the formation of a biofilm in the mouth, nose, throat, ear, skin, wound, or digestive tract of a subject, the method comprising: administering to the mouth, nose, ear or digestive tract of the subject an effective amount of a composition comprising a soluble derivatized chitosan, thereby preventing the formation of a biofilm in the mouth, nose, throat, ear, skin, wound, or digestive tract of the subject.

In one embodiment, the method further comprises administering an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the method further comprises administering an antibiotic, anti-inflammatory, or mucolytic (expectorant) compound to a subject in conjunction with or subsequent to the administration of the composition.

In one embodiment, the method further comprises administering an antibiotic, anti-inflammatory, or mucolytic (expectorant) compound to a subject in conjunction with, prior to or subsequent to the administration of the composition.

In one embodiment, the subject is infected with planktonic bacteria.

In one embodiment, the subject is infected with bacteria listed in Tables 1 and/or 2.

In one embodiment, the composition reduces the viability of planktonic bacteria.

In one embodiment, the composition reduces colonization of the planktonic bacteria.

In one embodiment, the composition is administered topically, orally, enterally, or by inhalation (e.g., nebulizer, nasal spray, or sinus spray).

In one embodiment, the effective amount is therapeutically effective amount.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan comprises a chitosan of the following formula (I):

formula (I)

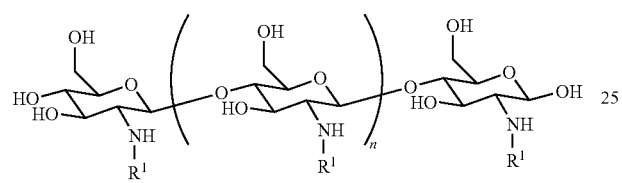

wherein:
n is an integer between 20 and 6000; and
each $R^1$ is independently selected for each occurrence from hydrogen, acetyl, and a group of formula (II):

formula (II)

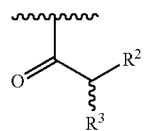

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

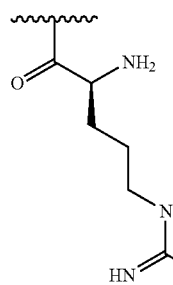 and 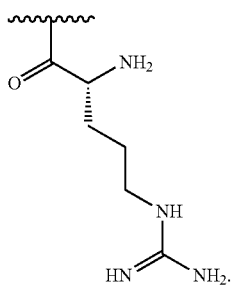

In one embodiment, $R^2$ is amino and $R^3$ is a lysine side chain.

In one embodiment, $R^1$ is selected from one of the following:

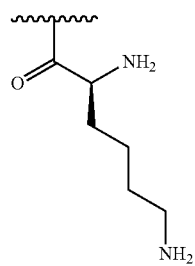 and 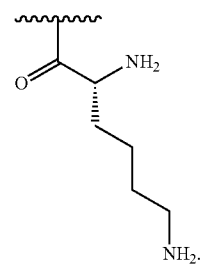

In one embodiment, $R^2$ is amino and $R^3$ is a histidine side chain.

In one embodiment, $R^1$ is selected from one of the following:

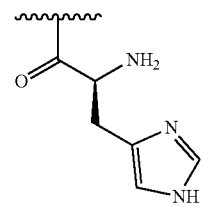 and 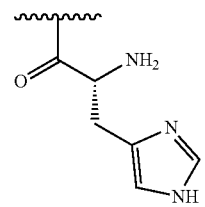

In one embodiment, at least 1% of $R^1$ substituents are selected from one of the following:

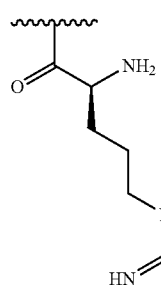 and 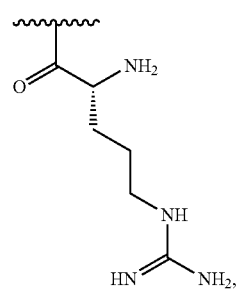

and at least 1% of $R^1$ substituents are selected from the following:

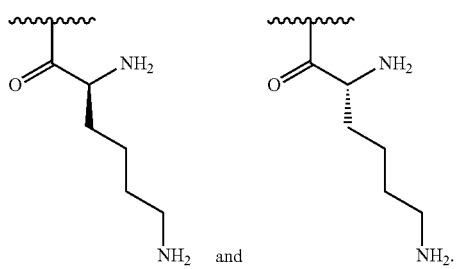 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

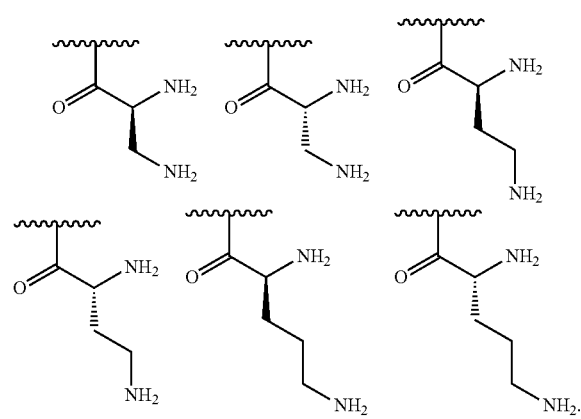

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

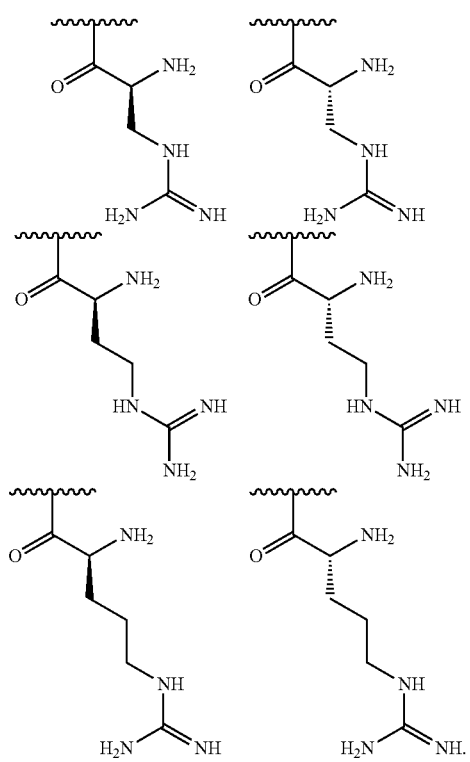

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is C alkyl substituted with an amino group.

In one embodiment, $R^3$ is $C_6$ alkyl substituted with an amino group.

In one embodiment, $R^1$ is selected from one of the following:

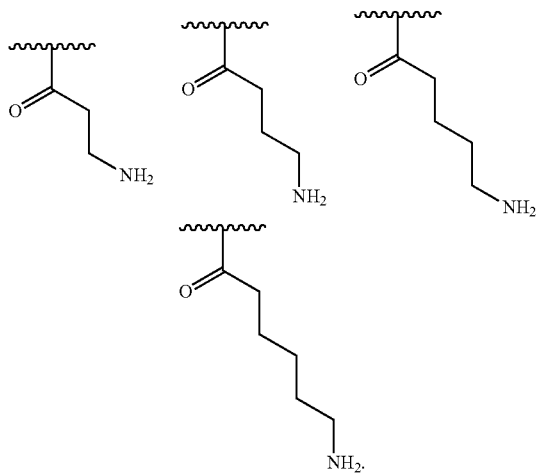

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

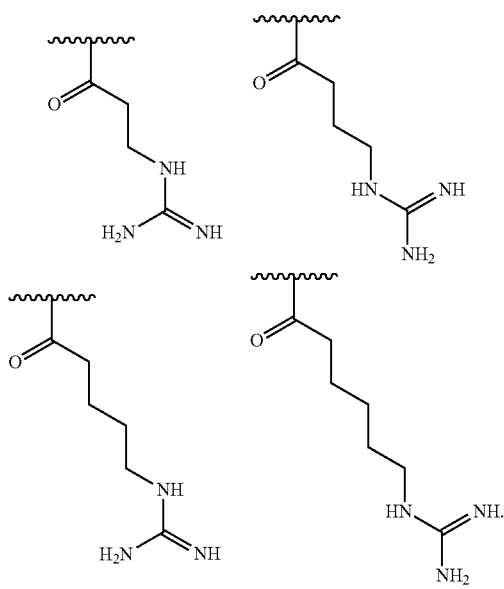

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the functionalized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a method of treating or preventing (e.g., reducing the degree of) a complication of cystic fibrosis in a subject, the method comprising: administering to the subject an effective amount of a composition comprising a soluble chitosan or derivatized chitosan, thereby treating or preventing a complication of cystic fibrosis.

In one embodiment, the complication of cystic fibrosis is lung infection or respiratory congestion.

In one embodiment, the subject has a bacterial infection, e.g., bacteria list in Table 3, e.g., *Pseudomonas aeruginosa*.

In one embodiment, the subject comprises at least one biofilm.

In one embodiment, exopolysaccharides (EPS) of the biofilm comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea*, or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the composition.

In one embodiment, the viscosity (e.g., apparent viscosity) of the biofilm is reduced by at least 1, 2, 5, 10, 50, 100, 200, 500, or 1000 fold, compared to the biofilm that has not been contacted with the composition.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the composition.

In one embodiment, the method further comprises administering an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same composition or dosage form).

In one embodiment, the method further comprises administering an antibiotic, anti-inflammatory, or mucolytic (expectorant) compound to a subject in conjunction with, prior to or subsequent to the administration of the composition.

In one embodiment, the antibiotic, anti-inflammatory, or mucolytic (expectorant) compound is administered in a dosage to achieve a synergistic effect.

In one embodiment, the biofilm is in the respiratory system (e.g., airways, lung, throat, nose).

In one embodiment, the subject is infected with planktonic bacteria.

In one embodiment, the composition reduces the viability of planktonic bacteria.

In one embodiment, the composition reduces colonization of the planktonic bacteria.

In one embodiment, the planktonic bacteria are clumped, e.g., to facilitate removal by expectoration, lavage, or chest percussion.

In one embodiment, the composition is administered by inhalation (e.g., nebulizer, nasal spray, nasal swab, or sinus spray).

In one embodiment, the effective amount is therapeutically effective amount.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan comprises a chitosan of the following formula (I):

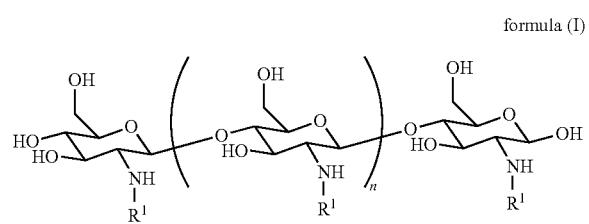

formula (I)

wherein:

n is an integer between 20 and 6000; and each $R^1$ is independently selected for each occurrence from hydrogen, acetyl, and a group of formula (II):

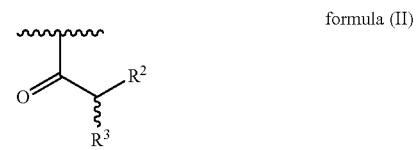

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

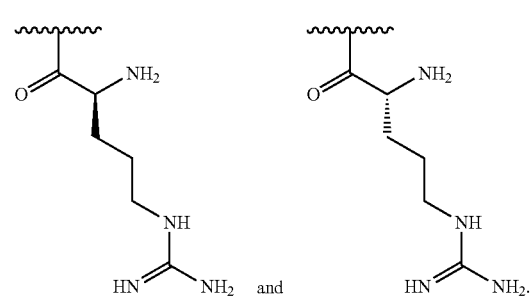

In one embodiment, $R^2$ is amino and $R^3$ is a lysine side chain.

In one embodiment, $R^1$ is selected from one of the following:

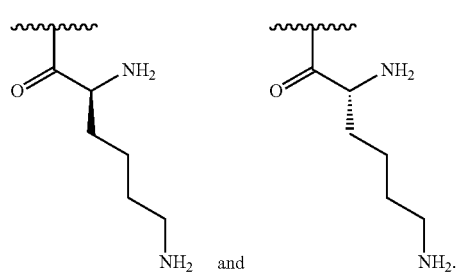 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

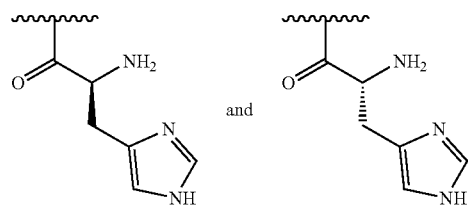

In one embodiment, at least 1% of $R^1$ substituents are selected from one of the following:

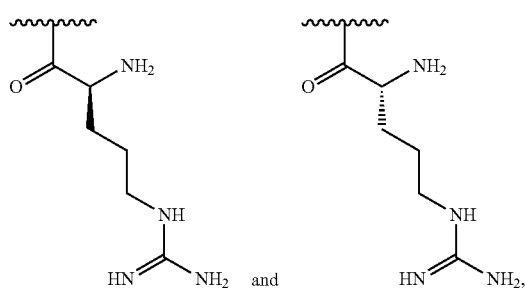 [SMILES: *C(=O)[C@@H](N)CCCNC(=N)N ; *C(=O)[C@H](N)CCCNC(=N)N]

AND at least 1% of $R^1$ substituents are selected from the following:

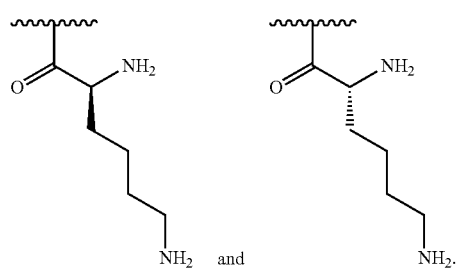 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

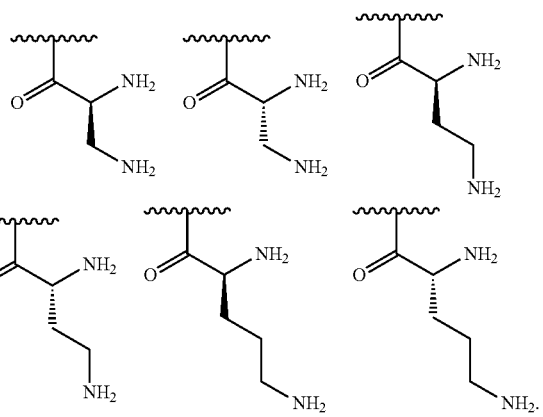

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

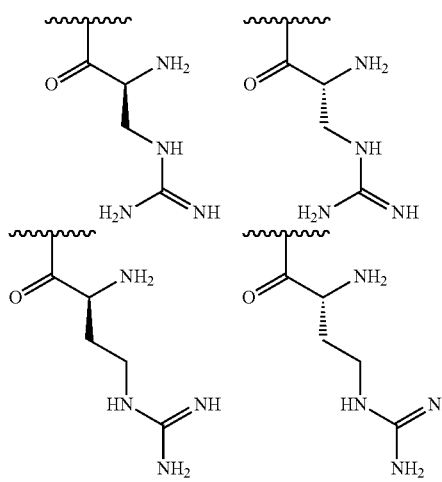

-continued

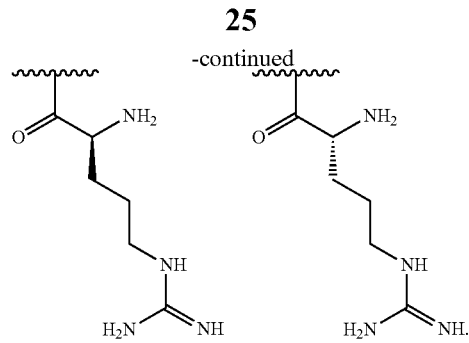

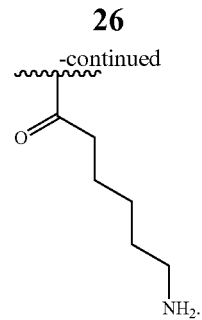

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

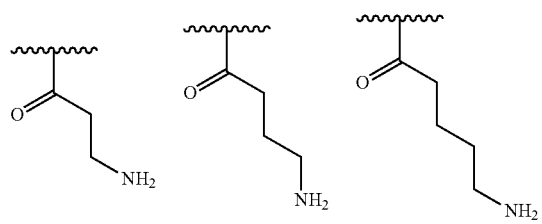

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

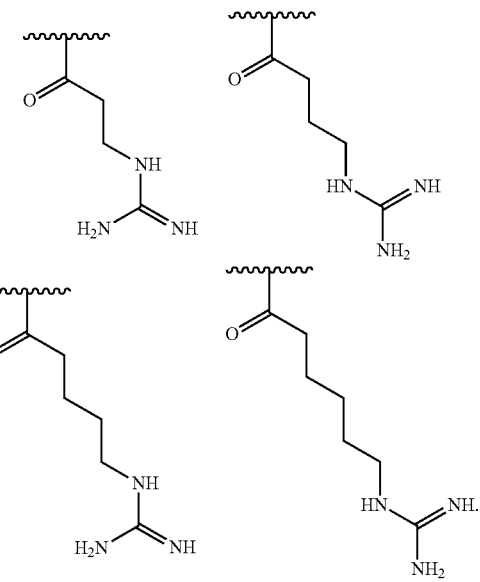

In one embodiment, at least 25% of R substituents are H, at least 1% of R substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a method of treating or preventing (e.g., reducing the degree of) a gastrointestinal tract infection in a subject, the method comprising: administering to the subject an effective amount of a composition comprising a soluble derivatized chitosan, thereby treating or preventing the gastrointestinal tract infection.

In one embodiment, the gastrointestinal tract infection is noninflammatory gastroenteritis, inflammatory gastroenteritis, invasive gastroenteritis, or nectrotic or necrotizing enteritis.

In one embodiment, the subject is infected with *Staphylococcus aureus, Bacillus cereus, Clostridium perfringens, Clostridium botulinum, Vibrio cholerae, Escherichia coli, Clostridium difficile, Vibrio parahemolyticus, Bacillus anthracis, Shigella* sp., *Salmonella* sp., *Campylobacter jejuni, Vibrion vulnificus, Yersinia* sp., *Francisella tularensis*, or *Helicobacter pylori*.

In one embodiment, the subject is infected with bacteria listed in Table 2.

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea*, or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the composition.

In one embodiment, the viscosity (e.g., apparent viscosity) of the biofilm is reduced by at least 1, 2, 5, 10, 50, 100, 200, 500, or 1000 fold, compared to the biofilm that has not been contacted with the composition.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the composition.

In one embodiment, the method further comprises administering an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same composition or dosage form).

In one embodiment, the method further comprises administering an antibiotic, anti-inflammatory, or mucolytic (expectorant) compound to a subject in conjunction with, prior to or subsequent to the administration of the composition.

In one embodiment, the antibiotic, anti-inflammatory, or mucolytic (expectorant) compound is administered in a dosage to achieve a synergistic effect.

In one embodiment, the biofilm is in the gastrointestinal tract.

In one embodiment, the subject is infected with planktonic bacteria.

In one embodiment, the composition reduces the viability of planktonic bacteria.

In one embodiment, the composition reduces colonization of the planktonic bacteria.

In one embodiment, the planktonic bacteria are clumped.

In one embodiment, the composition is administered orally, or enterally.

In one embodiment, the effective amount is therapeutically effective amount.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in duodenum.

In one embodiment, the derivatized chitosan is soluble in aqueous solution from about pH 2.0 to about pH 4.0, e.g., in stomach.

In one embodiment, the derivatized chitosan is soluble in aqueous solution from about pH 8.0 to about pH 8.5, e.g., in lower part of the gastrointestinal tract.

In one embodiment, the composition is active below pH 6 (e.g., in stomach and duodenum) or near or above pH 8 (e.g., in colon).

In one embodiment, the composition is active between pH 6 and pH 8.

In one embodiment, the composition is delivered e.g., by capsule, time release capsule, pH release capsule, as a powder dissolved in the digestive tract, or lozenge.

In one embodiment, the composition is delivered by mixing in food, or dissolved in any liquid, e.g., in a liquid formulation, e.g., daily or multiple times daily.

In one embodiment, the derivatized chitosan comprises a chitosan of the following formula (I):

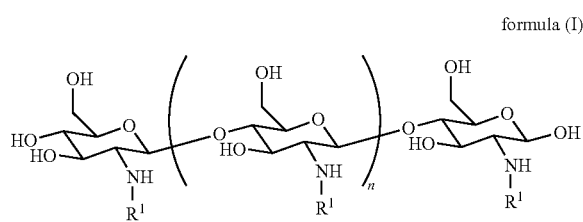

formula (I)

wherein:
n is an integer between 20 and 6000; and
each $R^1$ is independently selected for each occurrence from hydrogen, acetyl, and a group of formula (II):

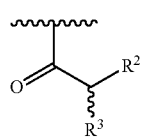

formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

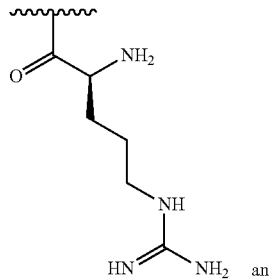 and 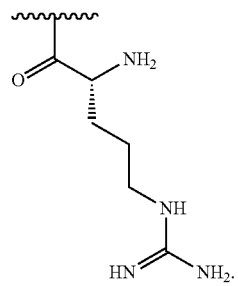

In one embodiment, $R^2$ is amino and $R^3$ is a lysine side chain.

In one embodiment, $R^1$ is selected from one of the following:

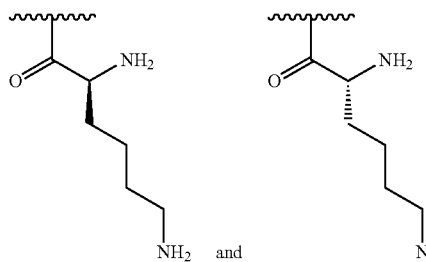 and 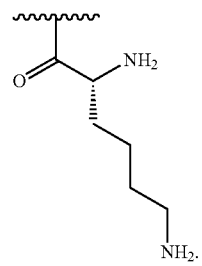

In one embodiment, $R^2$ is amino and $R^3$ is a histidine side chain.

In one embodiment, $R^1$ is selected from one of the following:

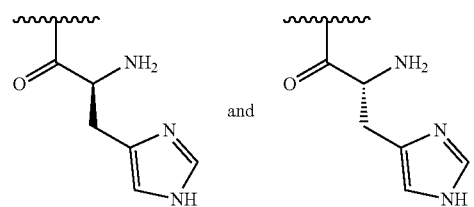 and 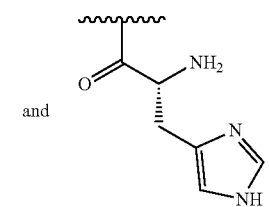

In one embodiment, at least 1% of $R^1$ substituents are selected from one of the following:

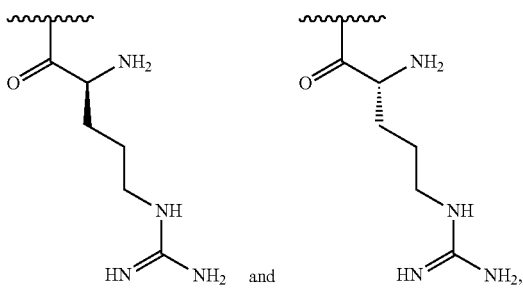 [SMILES: *C(=O)[C@@H](N)CCCNC(=N)N ; *C(=O)[C@H](N)CCCNC(=N)N] and 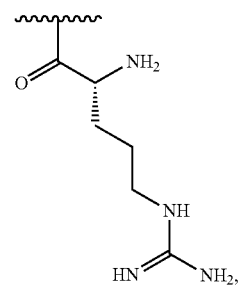

AND at least 1% of $R^1$ substituents are selected from the following:

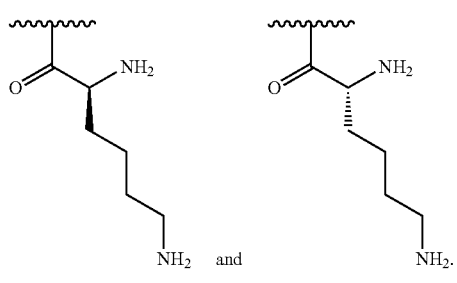 [SMILES: *C(=O)[C@@H](N)CCCCN ; *C(=O)[C@H](N)CCCCN] and 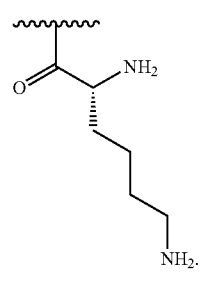

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

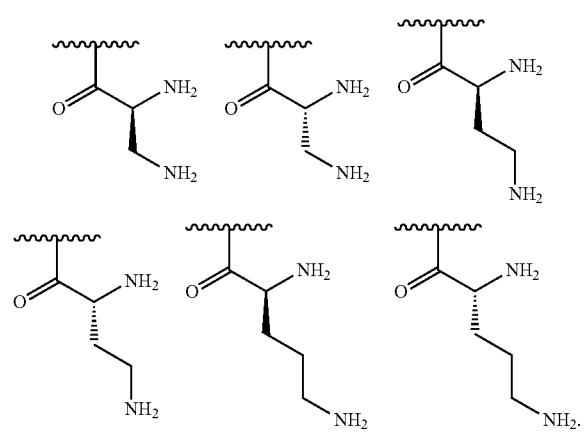

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

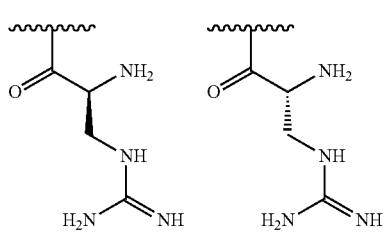

-continued

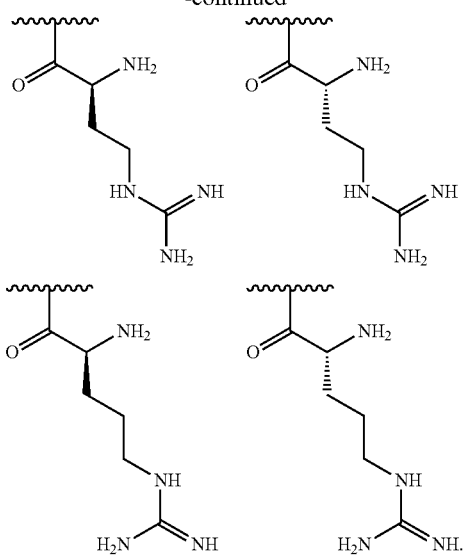

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is C alkyl substituted with an amino group.

In one embodiment, $R^3$ is $C_6$ alkyl substituted with an amino group.

In one embodiment, $R^1$ is selected from one of the following:

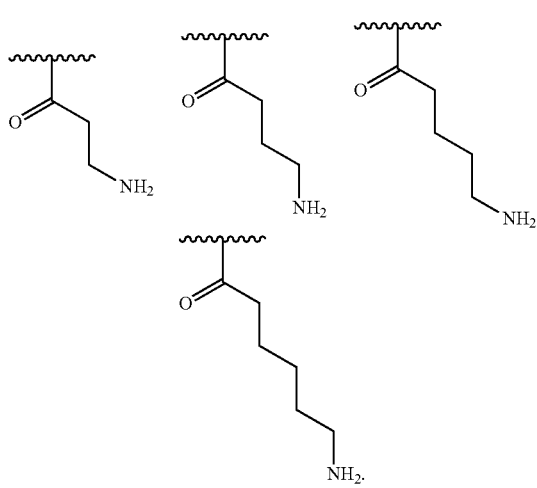

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

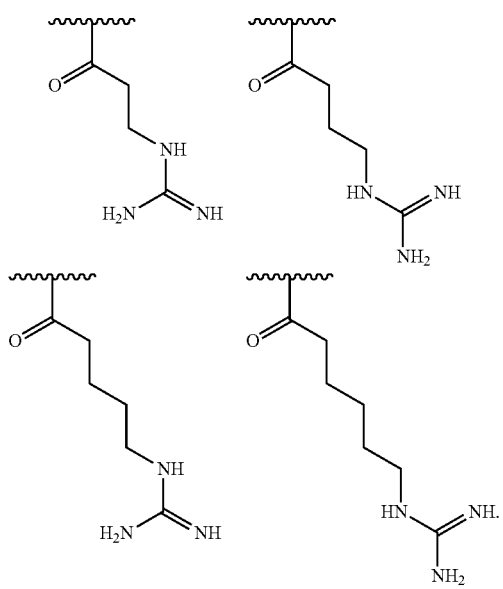

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a method of treating or preventing (e.g., reducing the degree of) a wound infection in a subject, the method comprising: administering to the wound of the subject an effective amount of a composition comprising a soluble derivatized chitosan, thereby treating or preventing the wound infection. Exemplary wounds include wounds on the skin of a subject, such as a wound that damages and/or penetrates the skin of a subject.

In one embodiment, the subject is infected with bacteria listed in Table 4.

In one embodiment, the wound of the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea,* or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the composition.

In one embodiment, the viscosity (e.g., apparent viscosity) of the biofilm is reduced by at least 1, 2, 5, 10, 50, 100, 200, 500, or 1000 fold, compared to the biofilm that has not been contacted with the composition.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the composition.

In one embodiment, the composition is a rinse, a leave-in rinse, a gel, a component of a dressing, or a time-release formulation.

In one embodiment, the method further comprises administering an additional agent, e.g., a pharmaceutical agent, or a non-pharmaceutical agent (e.g., a non-toxic surfactant).

In one embodiment, the second agent is administered in a dosage to achieve a synergistic effect.

In one embodiment, the second agent is administered together with the soluble derivatized chitosan (e.g., in the same composition or dosage form).

In one embodiment, the method further comprises administering an antibiotic, anti-inflammatory, or mucolytic (expectorant) compound to a subject in conjunction with, prior to or subsequent to the administration of the composition.

In one embodiment, the antibiotic, anti-inflammatory, or mucolytic (expectorant) compound is administered in a dosage to achieve a synergistic effect.

In one embodiment, the method further comprises rinsing the wound with a composition described herein.

In one embodiment, the subject is infected with planktonic bacteria.

In one embodiment, the composition reduces the viability of planktonic bacteria.

In one embodiment, the composition reduces colonization of the planktonic bacteria.

In one embodiment, the planktonic bacteria are clumped.

In one embodiment, the composition is administered topically.

In one embodiment, the effective amount is therapeutically effective amount.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in the wound.

In one embodiment, the derivatized chitosan comprises a chitosan of the following formula (I):

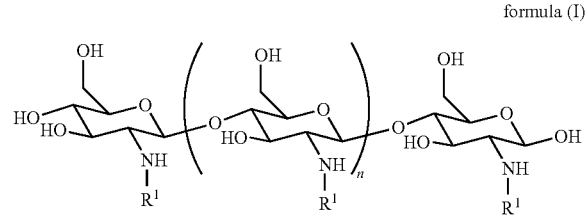

formula (I)

wherein:
n is an integer between 20 and 6000; and
each $R^1$ is independently selected for each occurrence from hydrogen, acetyl, and a group of formula (II):

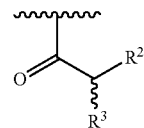

formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

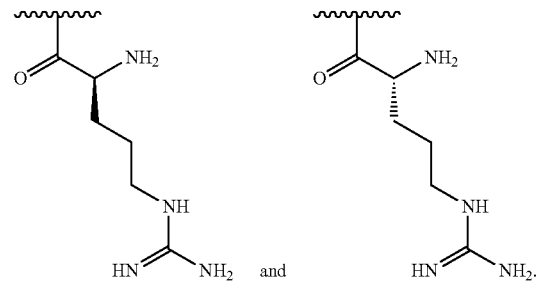 [SMILES: *C(=O)[C@@H](N)CCCNC(=N)N ; *C(=O)[C@H](N)CCCNC(=N)N]

In one embodiment, $R^2$ is amino and $R^3$ is a lysine side chain.

In one embodiment, $R^1$ is selected from one of the following:

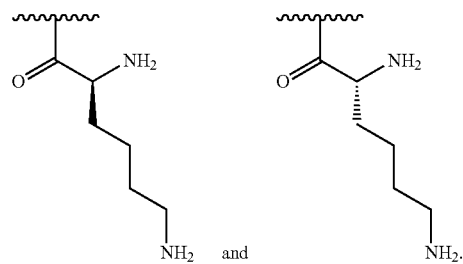 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

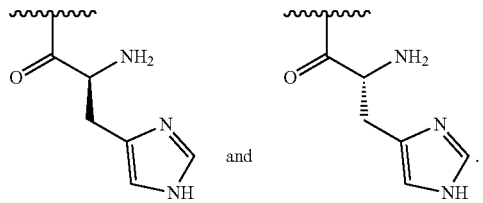 [SMILES: *C(=O)[C@@H](N)Cc1c[nH]cn1 ; *C(=O)[C@H](N)Cc1c[nH]cn1]

and

In one embodiment, at least 1% of $R^1$ substituents are selected from one of the following:

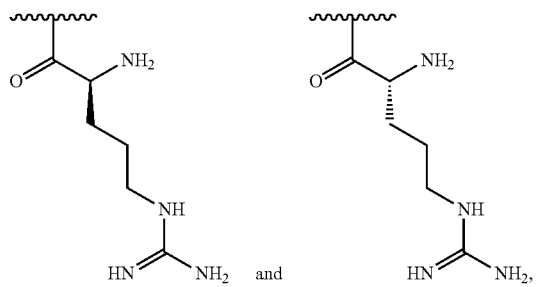 [SMILES: *C(=O)[C@@H](N)CCCNC(=N)N ; *C(=O)[C@H](N)CCCNC(=N)N]

and at least 1% of $R^1$ substituents are selected from the following:

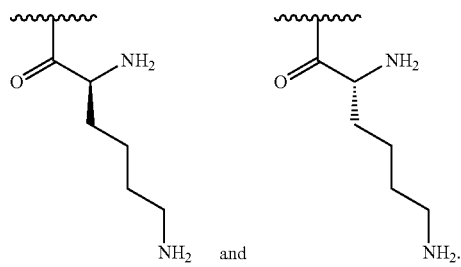

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^1$ is selected from one of the following:

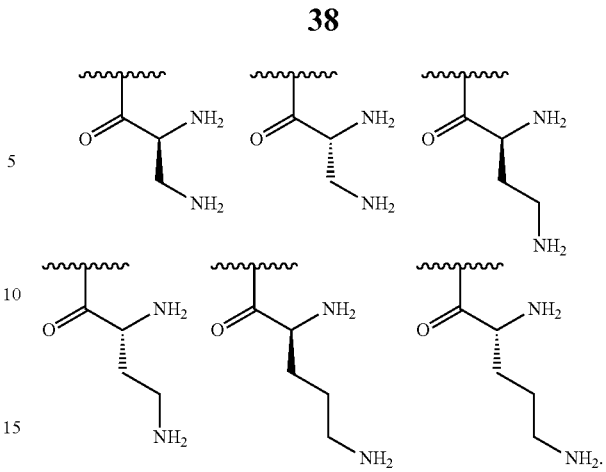

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^1$ is selected from one of the following:

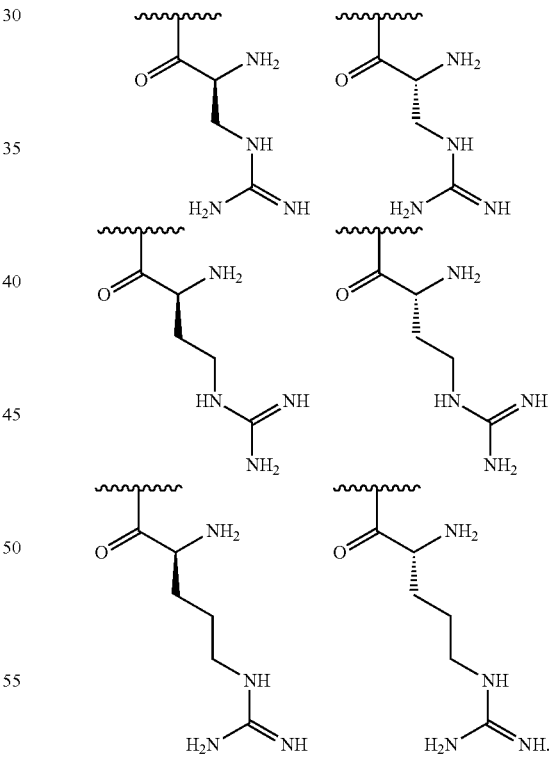

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^1$ is selected from one of the following:

[Chemical structures showing acyl groups with terminal NH₂ at various chain lengths]

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^1$ is selected from one of the following:

[Chemical structures showing acyl groups with terminal guanidino groups at various chain lengths]

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In another aspect, the invention features a liquid composition comprising a soluble chitosan or derivatized chitosan described herein.

In one embodiment, the composition further comprises a thickening agent.

In one embodiment, the derivatized chitosan comprises a chitosan of the following formula (I):

formula (I)

[Chemical structure of chitosan polymer showing repeating units with OH, HO, NH-R¹ substituents]

wherein:

n is an integer between 20 and 6000; and each $R^1$ is independently selected for each occurrence from hydrogen, acetyl, and a group of formula (II):

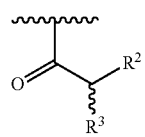

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

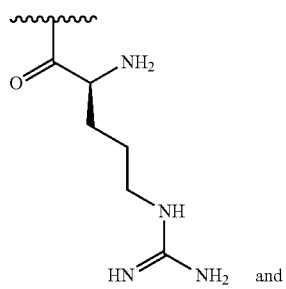 and 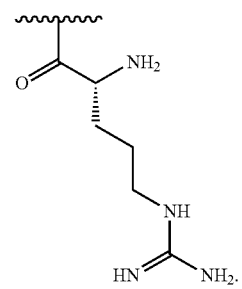

In one embodiment, $R^2$ is amino and $R^3$ is a lysine side chain.

In one embodiment, $R^1$ is selected from one of the following:

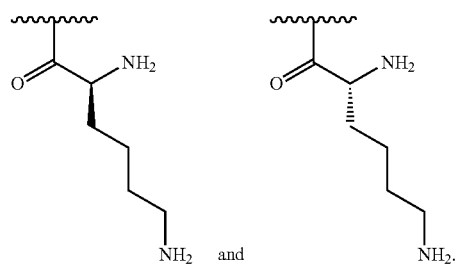 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

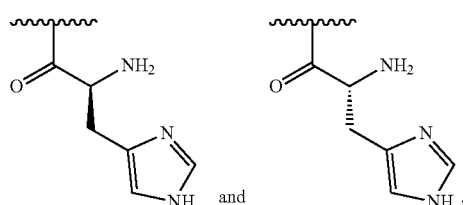

In one embodiment, at least 1% of $R^1$ substituents are selected from one of the following:

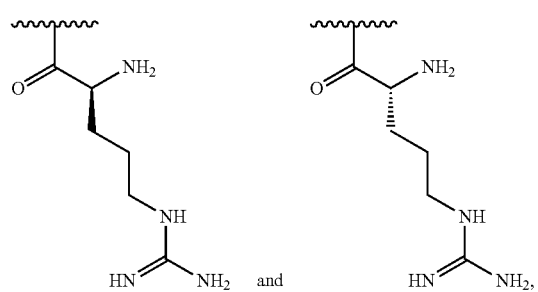 [SMILES: *C(=O)[C@@H](N)CCCNC(=N)N ; *C(=O)[C@H](N)CCCNC(=N)N]

AND at least 1% of $R^1$ substituents are selected from the following:

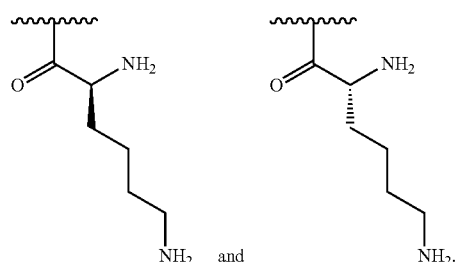

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

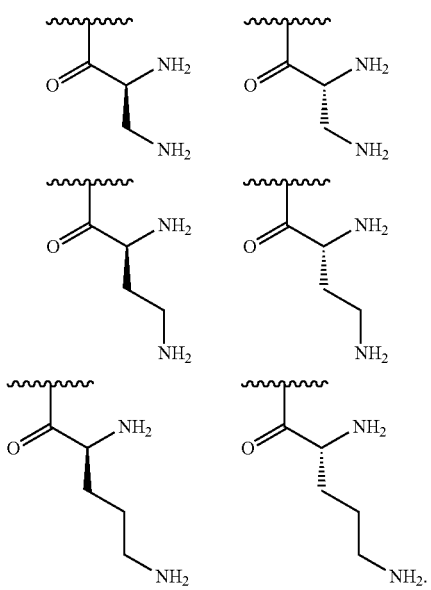

In one embodiment, R is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

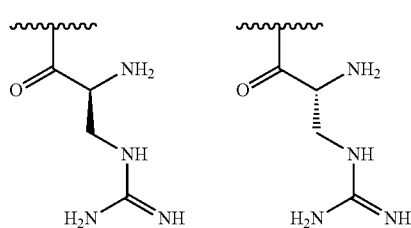

-continued

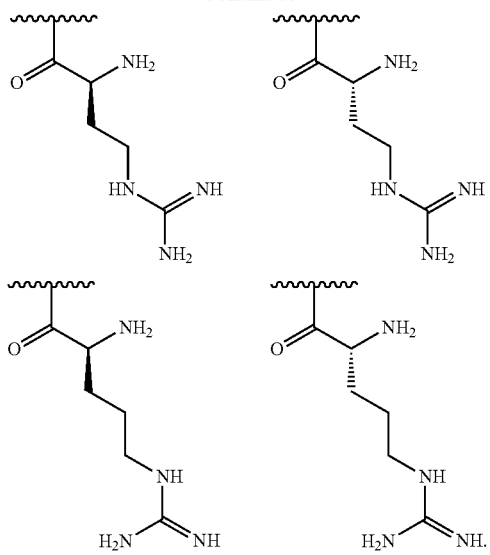

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

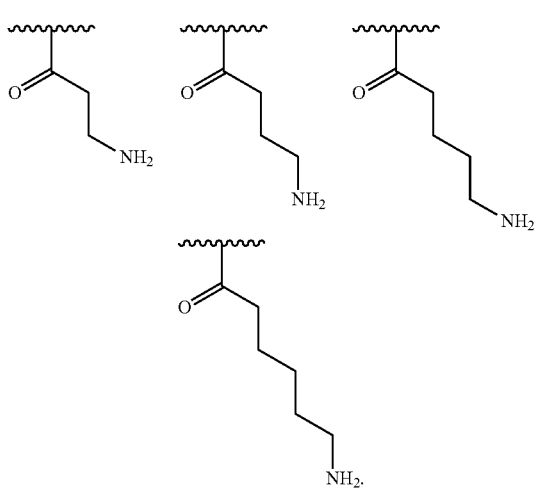

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

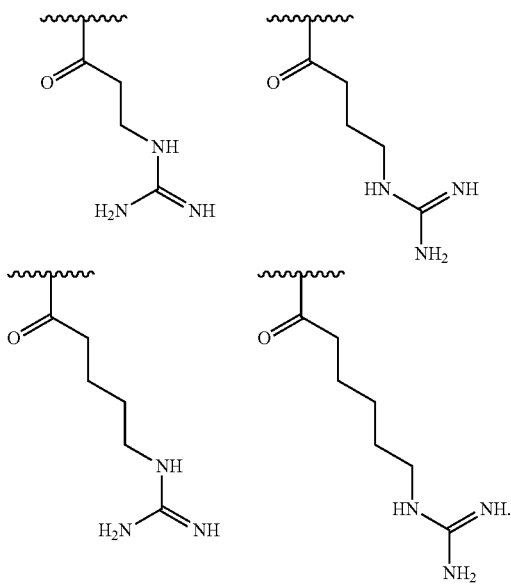

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the composition is active below pH 6 (e.g., in stomach and duodenum) or near or above pH 8 (e.g., in colon).

In one embodiment, the composition is active between pH 6 and pH 8.

In one embodiment, the composition further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the derivatized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a solid particulate (e.g., solid lipid particulate) composition comprising a soluble derivatized chitosan described herein.

In one embodiment, the derivatized chitosan comprises a chitosan of the following formula (I):

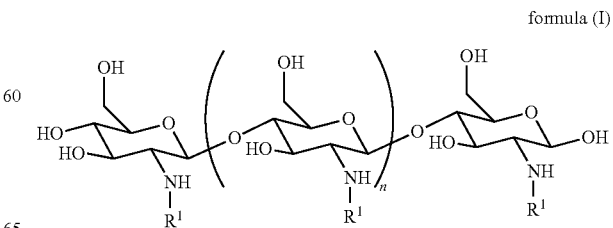

formula (I)

wherein:

n is an integer between 20 and 6000; and each $R^1$ is independently selected for each occurrence from hydrogen, acetyl, and a group of formula (II):

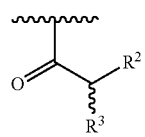

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

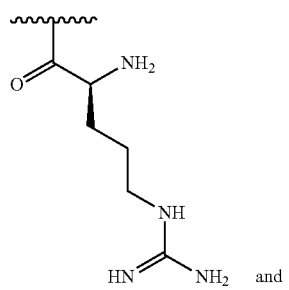

In one embodiment, $R^2$ is amino and $R^3$ is a lysine side chain.

In one embodiment, $R^1$ is selected from one of the following:

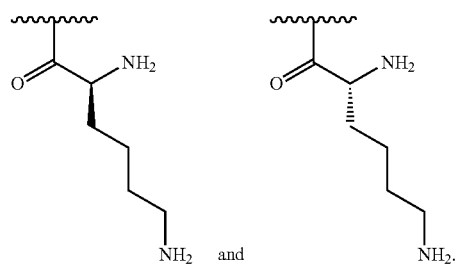 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

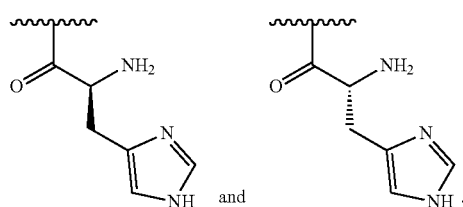 [SMILES: *C(=O)[C@@H](N)Cc1c[nH]cn1 ; *C(=O)[C@H](N)Cc1c[nH]cn1]

In one embodiment, at least 1% of $R^1$ substituents are selected from one of the following:

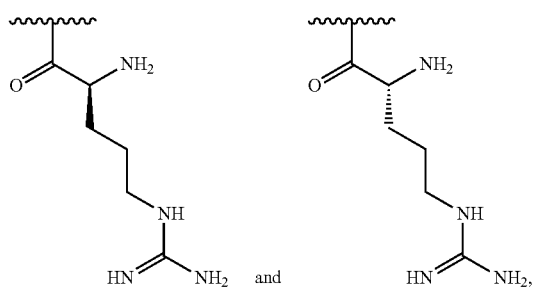 [SMILES: *C(=O)[C@@H](N)CCCNC(=N)N ; *C(=O)[C@H](N)CCCNC(=N)N]

and at least 1% of $R^1$ substituents are selected from the following:

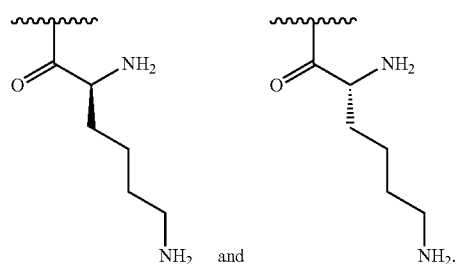

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

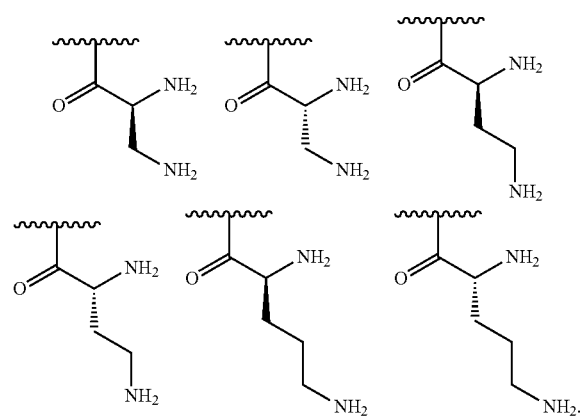

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

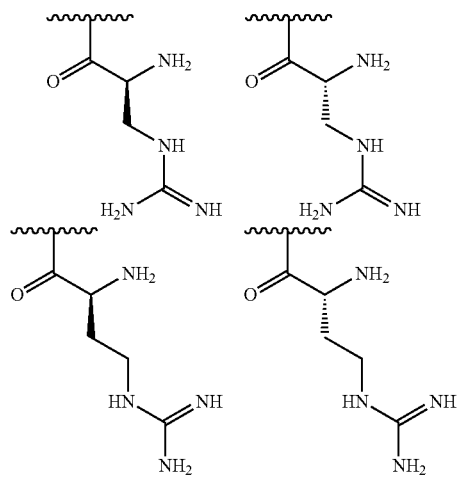

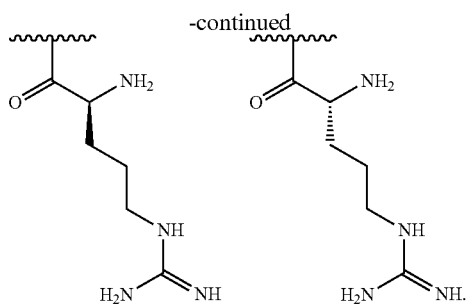

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is C alkyl substituted with an amino group.

In one embodiment, $R^3$ is $C_6$ alkyl substituted with an amino group.

In one embodiment, $R^1$ is selected from one of the following:

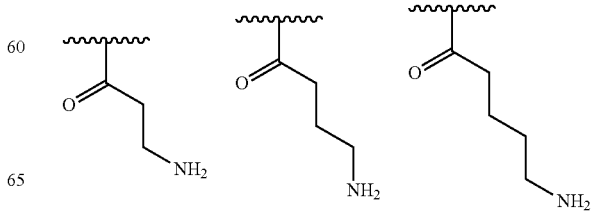

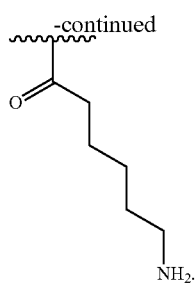

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

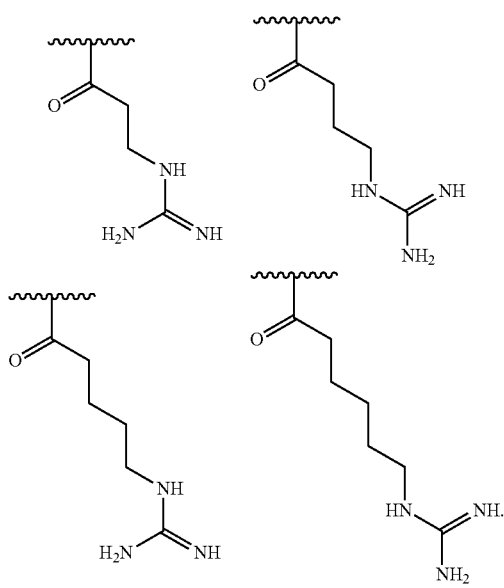

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in wounds or duodenum.

In one embodiment, the derivatized chitosan is soluble in aqueous solution from about pH 2.0 to about pH 4.0, e.g., in stomach.

In one embodiment, the derivatized chitosan is soluble in aqueous solution from about pH 8.0 to about pH 8.5, e.g., in lower part of the gastrointestinal tract.

In one embodiment, the composition further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the derivatized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a semisolid (e.g., ointment, cream, gel, paste, or liniment) composition comprising a soluble derivatized chitosan described herein.

In one embodiment, the derivatized chitosan comprises a chitosan of the following formula (I):

formula (I)

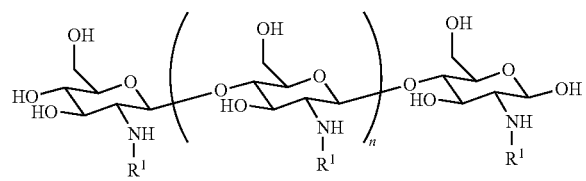

wherein:

n is an integer between 20 and 6000; and each $R^1$ is independently selected for each occurrence from hydrogen, acetyl, and a group of formula (II):

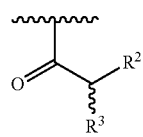

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

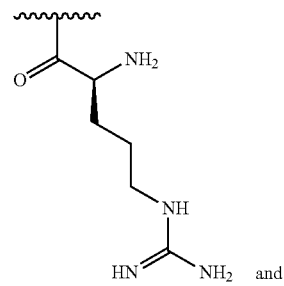

In one embodiment, $R^2$ is amino and $R^3$ is a lysine side chain.

In one embodiment, $R^1$ is selected from one of the following:

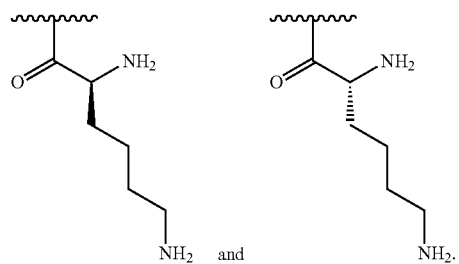 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

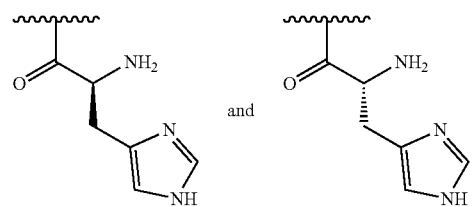

In one embodiment, at least 1% of $R^1$ substituents are selected from one of the following:

and at least 1% of $R^1$ substituents are selected from the following:

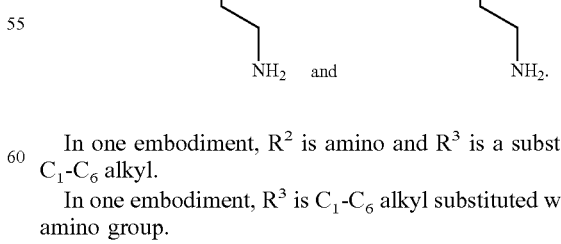

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

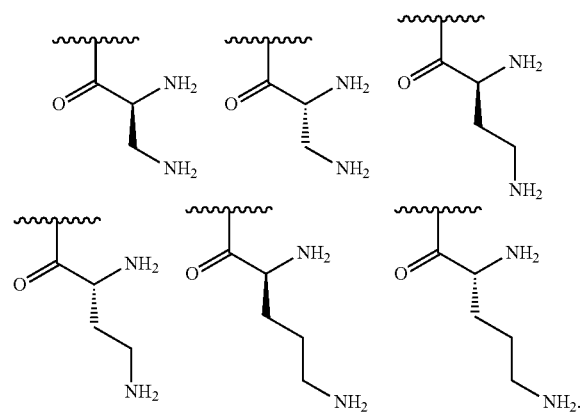

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

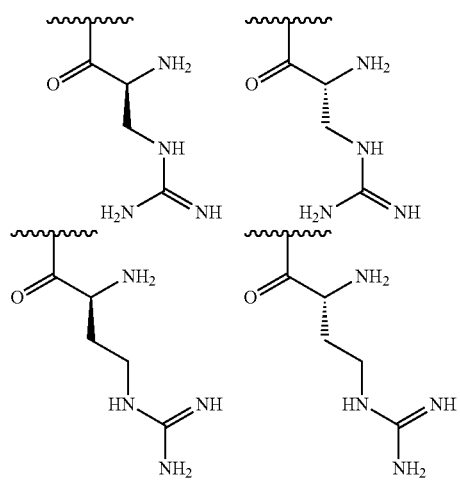

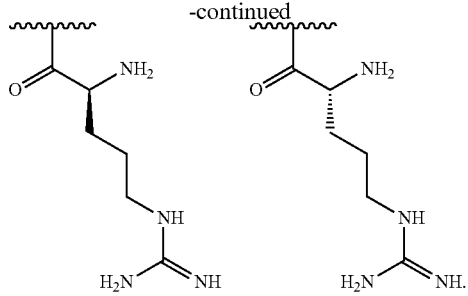

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

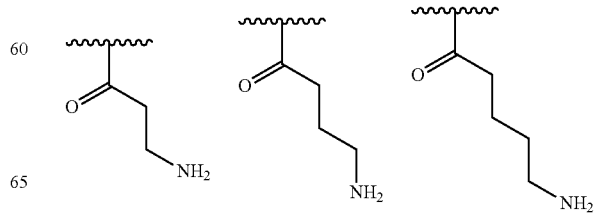

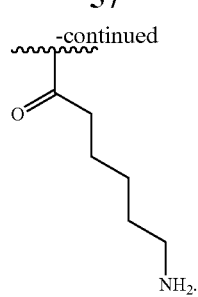

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

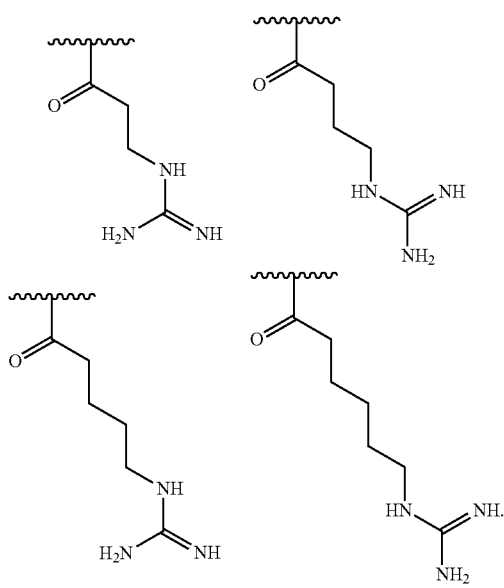

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in wounds.

In one embodiment, the composition further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the derivatized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a dressing or an ointment comprising soluble derivatized chitosan described herein, wherein the dressing or ointment is formulated such that the soluble chitosan or derivatized chitosan described herein is diffusible into a subject upon administration to the subject.

In one embodiment, the composition of the derivatized chitosan was autoclaved before use in the body.

In one embodiment, the derivatized chitosan comprises a chitosan of the following formula (I):

formula (I)

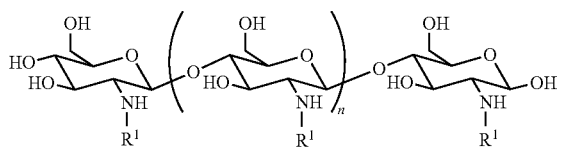

wherein:

n is an integer between 20 and 6000; and each $R^1$ is independently selected for each occurrence from hydrogen, acetyl, and a group of formula (II):

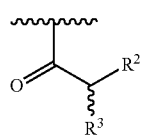
formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

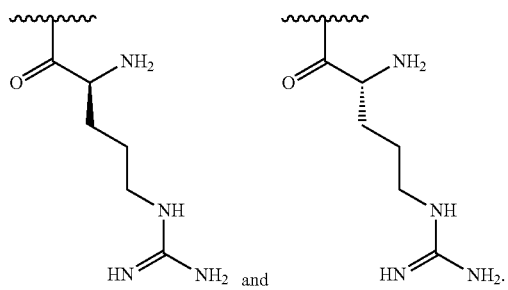 [SMILES: *C(=O)[C@@H](N)CCCNC(=N)N ; *C(=O)[C@H](N)CCCNC(=N)N]

In one embodiment, $R^2$ is amino and $R^3$ is a lysine side chain.

In one embodiment, $R^1$ is selected from one of the following:

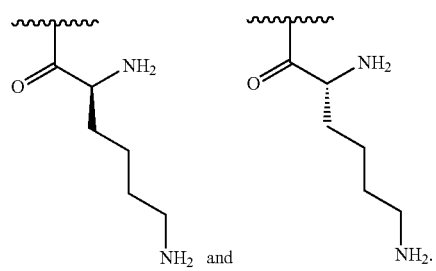 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

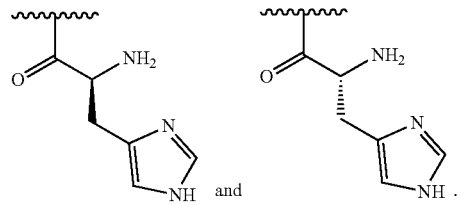 [SMILES: *C(=O)[C@@H](N)Cc1c[nH]cn1 ; *C(=O)[C@H](N)Cc1c[nH]cn1]

In one embodiment, at least 1% of $R^1$ substituents are selected from one of the following:

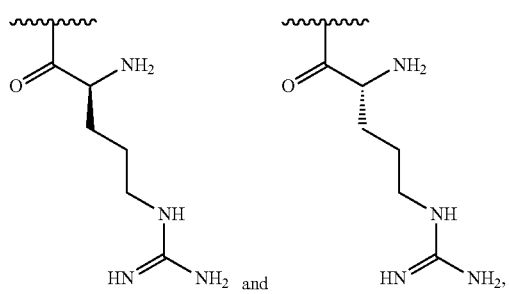 [SMILES: *C(=O)[C@@H](N)CCCNC(=N)N ; *C(=O)[C@H](N)CCCNC(=N)N]

and at least 1% of $R^1$ substituents are selected from the following:

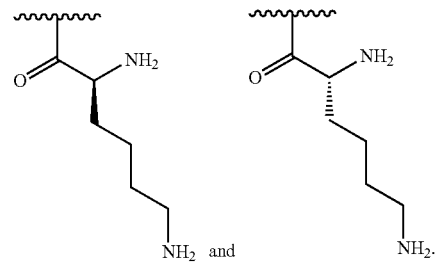 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

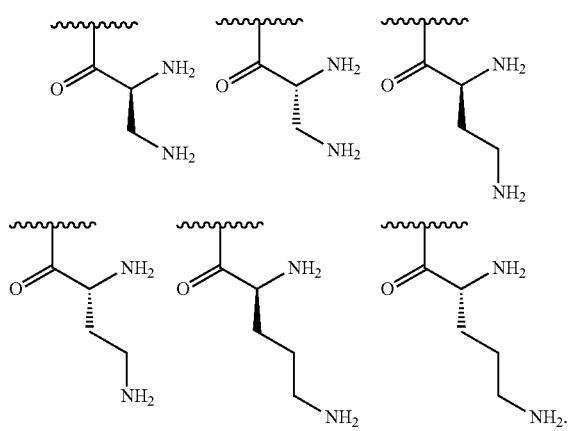
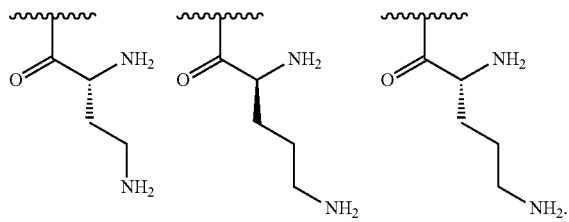

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

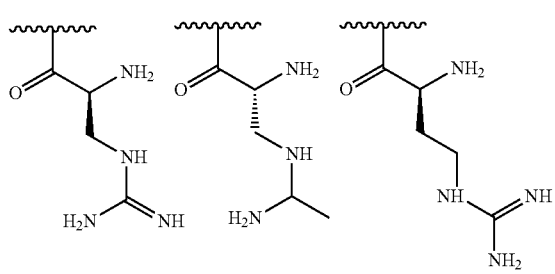

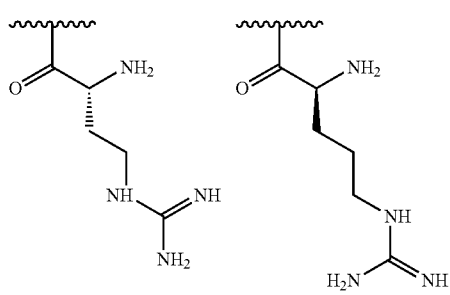

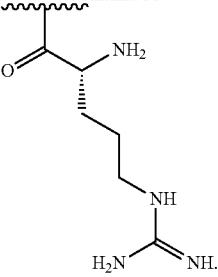

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

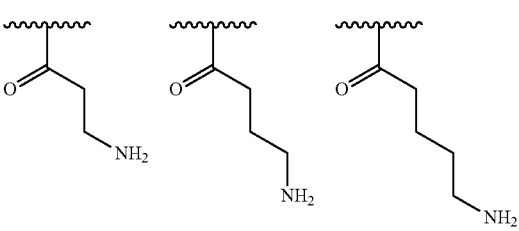

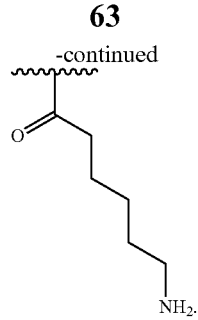

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

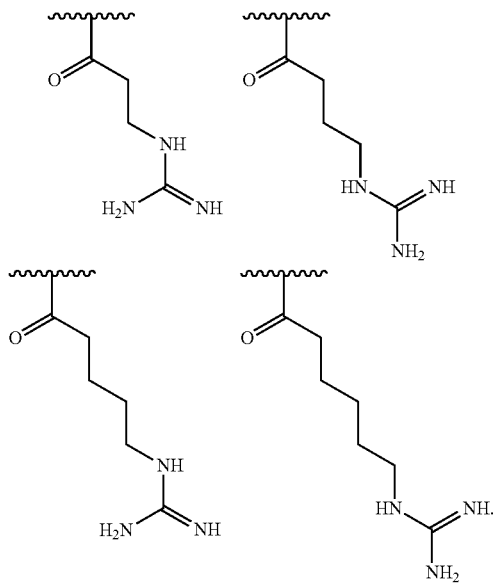

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in wounds.

In one embodiment, the dressing or ointment further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the derivatized chitosan is substantially free of other impurities, e.g., salt, e.g., NaCl.

In one embodiment, the dressing or ointment has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a kit comprising: a soluble derivatized chitosan described herein; and instructions to disrupt a performed biofilm in a subject.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the kit further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the kit further comprises an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the respiratory system (e.g., airways, lung, throat, nose), ear, eyes, mouth (e.g., tooth, tongue, mucosal surface), digestive system (e.g., stomach, small intestine, large intestine, colon, bowel), skin, or wound.

In one embodiment, the subject has a complication of cystic fibrosis (e.g., lung infection or respiratory congestion), pneumonia, dental plaque, oral disease (e.g., gingivitis, dental caries, or halitosis), ear infection, throat infection, eye infection (e.g., conjunctivitis), a complication in immunocompromised patient (e.g., lung infection or respiratory congestion), gastrointestinal infection, enteritis, or a symptom thereof.

In one embodiment, the subject is infected with bacteria listed in Table 1, 2, 3, or 4.

In one embodiment, the derivatized chitosan is administered topically, orally, or enterally.

In one embodiment, the derivatized chitosan is administered by inhalation (e.g., nebulizer, nasal spray, nasal swab, or sinus spray).

In one embodiment, the effective amount is therapeutically effective amount.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in wounds or duodenum.

In one embodiment, the derivatized chitosan is soluble in aqueous solution from about pH 2.0 to about pH 4.0, e.g., in stomach.

In one embodiment, the derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

formula (I)

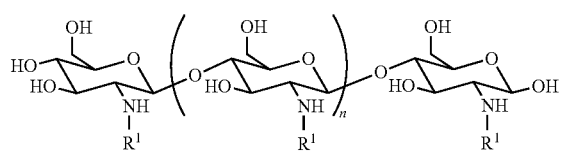

wherein:
n is an integer between 20 and 6000; and
each $R^1$ is independently selected for each occurrence from hydrogen, acetyl, and a group of formula (II):

formula (II)

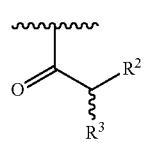

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

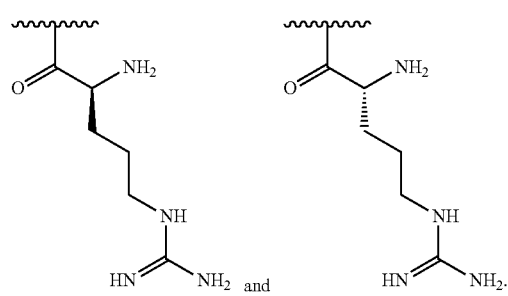 [SMILES: *C(=O)[C@@H](N)CCCNC(=N)N ; *C(=O)[C@H](N)CCCNC(=N)N]

In one embodiment, $R^2$ is amino and $R^3$ is a lysine side chain.

In one embodiment, $R^1$ is selected from one of the following:

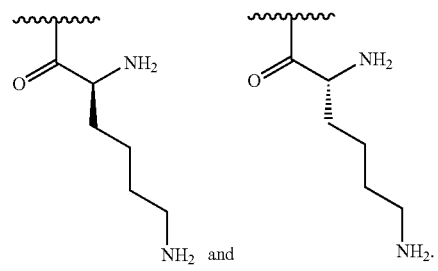 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

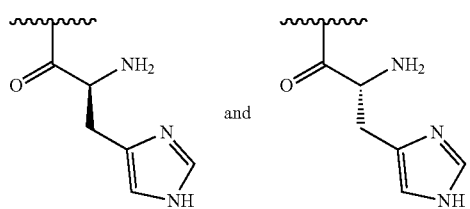

In one embodiment, at least 1% of $R^1$ substituents are selected from one of the following:

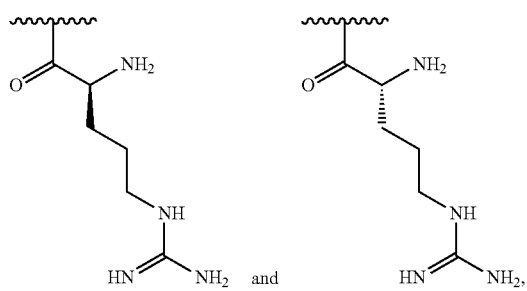 [SMILES: *C(=O)[C@@H](N)CCCNC(=N)N ; *C(=O)[C@H](N)CCCNC(=N)N]

and at least 1% of $R^1$ substituents are selected from the following:

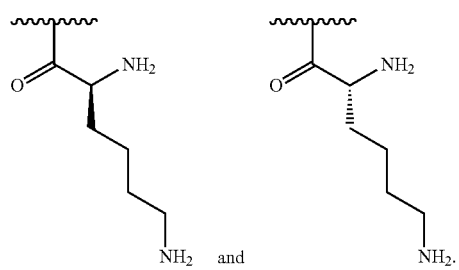 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

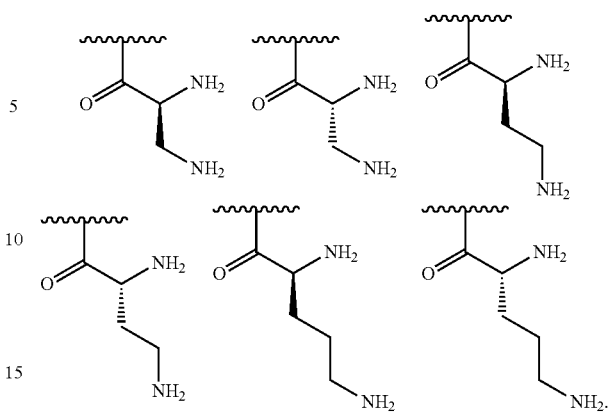

In one embodiment $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

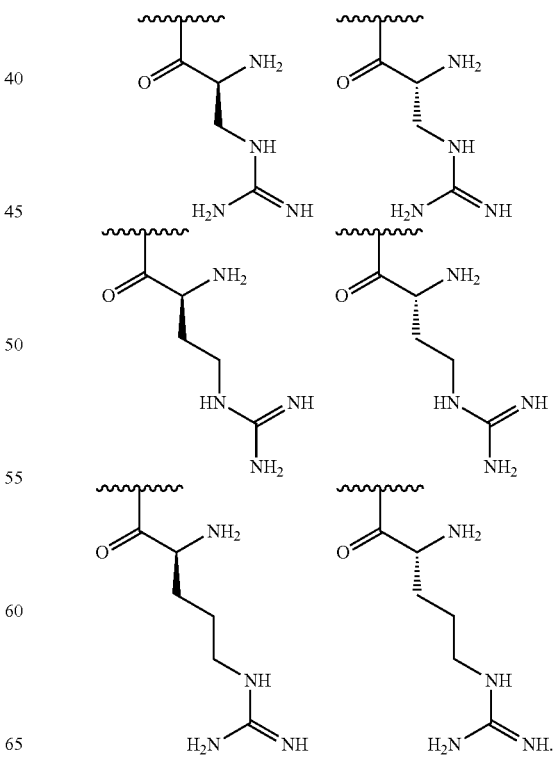

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

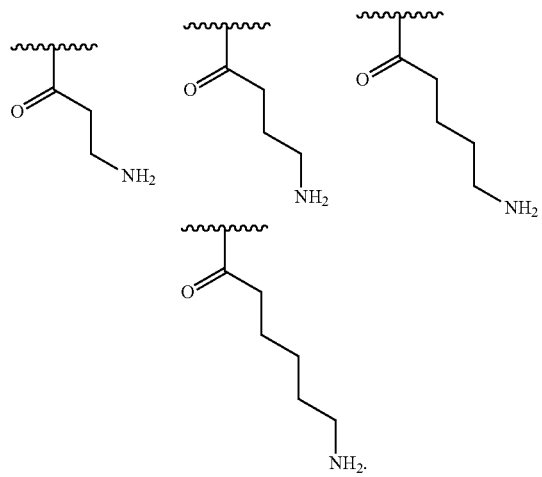

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

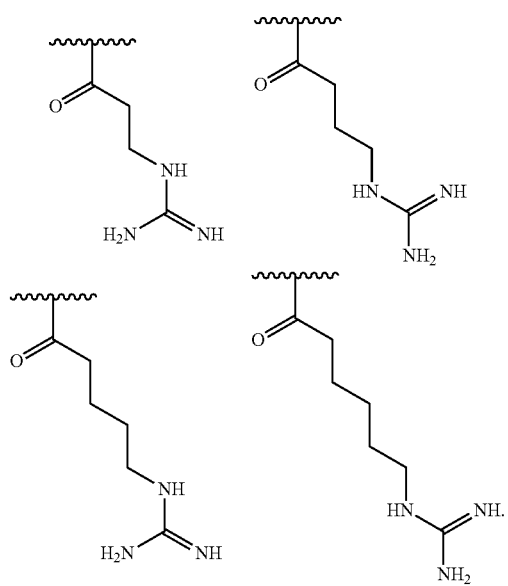

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the functionalized chitosan is substantially free of other impurities, e.g., salt, e.g., NaCl.

In one embodiment, the kit has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the kit has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a kit comprising:
a soluble derivatized chitosan described herein; and
instructions to prevent (e.g., reduce the degree of) the formation of a biofilm in the respiratory system of a subject.

In one embodiment, the kit further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the kit further comprises an antibiotic, anti-inflammatory, or mucolytic (expectorant) compound to a subject in conjunction with or subsequent to the administration of the derivatized chitosan.

In one embodiment, the kit further comprises an antibiotic, anti-inflammatory, or mucolytic (expectorant) compound to a subject in conjunction with, prior to or subsequent to the administration of the derivatized chitosan.

In one embodiment, the subject is infected with planktonic bacteria or infected with bacteria listed in Table 3.

In one embodiment, the subject is diagnosed with bacterial pneumonia.

In one embodiment, the derivatized chitosan reduces the viability of planktonic bacteria.

In one embodiment, the derivatized chitosan reduces colonization of the planktonic bacteria.

In one embodiment, the derivatized chitosan is administered by inhalation (e.g., nebulizer, nasal spray, or sinus spray).

In one embodiment, the kit comprises an effective amount (e.g., therapeutically effective amount) of derivatized chitosan.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan comprises a chitosan of the following formula (I):

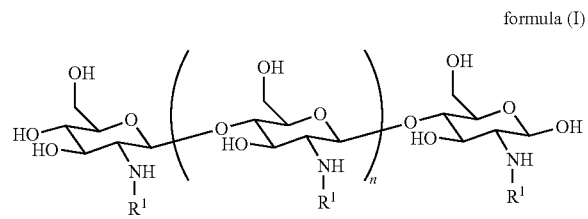

formula (I)

wherein:
n is an integer between 20 and 6000; and
each $R^1$ is independently selected for each occurrence from hydrogen, acetyl, and a group of formula (II):

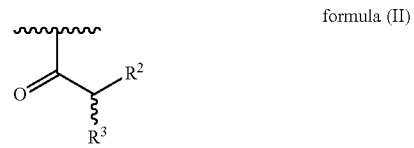

formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

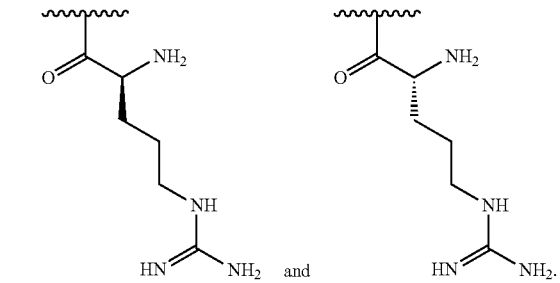 [SMILES: *C(=O)[C@@H](N)CCCNC(=N)N ; *C(=O)[C@H](N)CCCNC(=N)N]

In one embodiment, $R^2$ is amino and $R^3$ is a lysine side chain.

In one embodiment, $R^1$ is selected from one of the following:

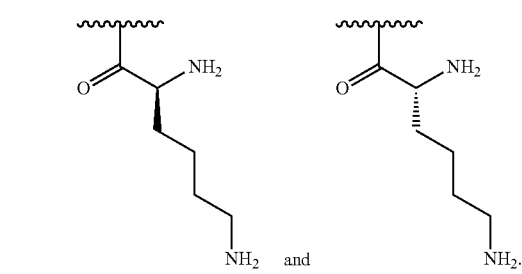 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

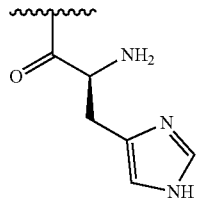 and 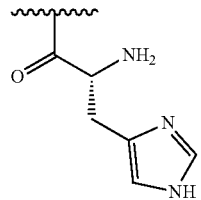.

In one embodiment, at least 1% of $R^1$ substituents are selected from one of the following:

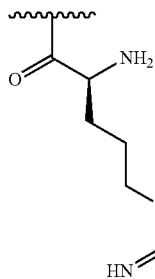 and 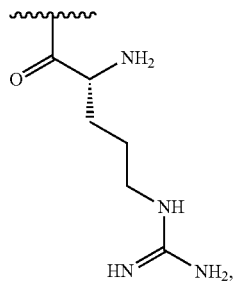, and at least 1% of $R^1$ substituents are selected from the following:

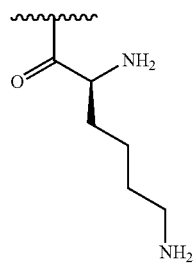 and 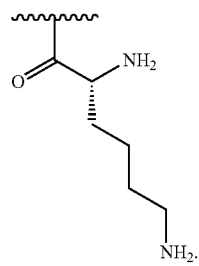.

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

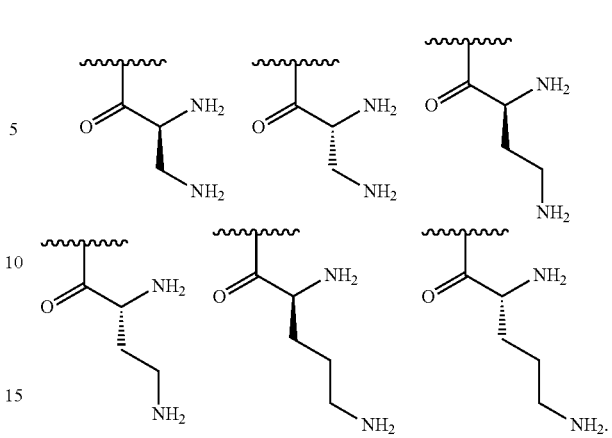

In one embodiment, R is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

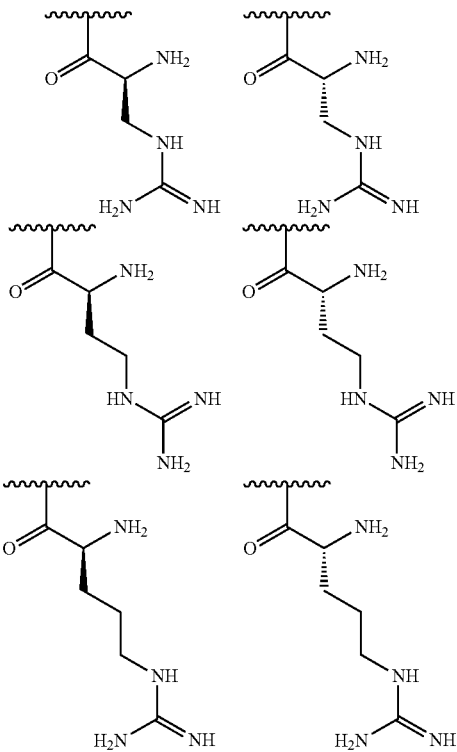

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is C alkyl substituted with an amino group.

In one embodiment, $R^3$ is $C_6$ alkyl substituted with an amino group.

In one embodiment, $R^1$ is selected from one of the following:

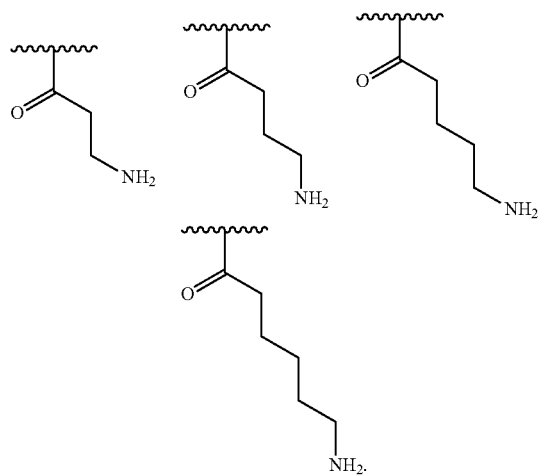

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

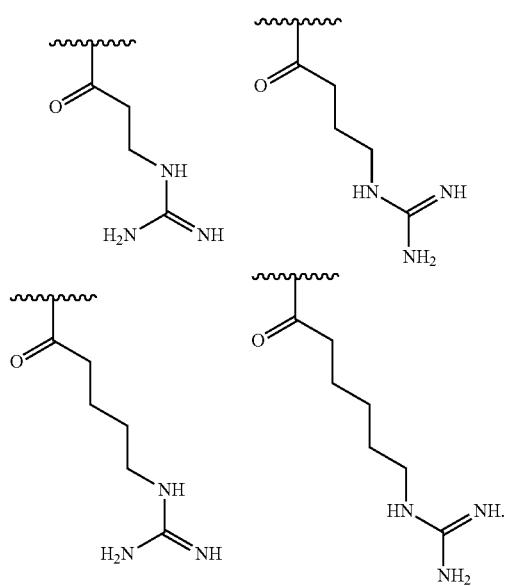

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the kit has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the kit has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a kit comprising:
a soluble derivatized chitosan described herein; and
instructions to prevent or treat a complication of cystic fibrosis in a subject.

In one embodiment, the complication of cystic fibrosis is lung infection or respiratory congestion.

In one embodiment, the subject has a bacterial infection, e.g., bacteria list in Table 3, e.g., *Pseudomonas aeruginosa.*

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea,* or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the kit further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the kit further comprises administering an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the respiratory system (e.g., airways, lung, throat, nose).

In one embodiment, the subject is infected with planktonic bacteria.

In one embodiment, the derivatized chitosan reduces the viability of planktonic bacteria.

In one embodiment, the derivatized chitosan reduces colonization of the planktonic bacteria.

In one embodiment, the planktonic bacteria are clumped, e.g., to facilitate removal by expectoration, lavage, or chest percussion.

In one embodiment, the derivatized chitosan is administered by inhalation (e.g., nebulizer, nasal spray, nasal swab, or sinus spray).

In one embodiment, the kit comprises an effective amount (e.g., therapeutically effective amount) of derivatized chitosan.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan comprises a chitosan of the following formula (I):

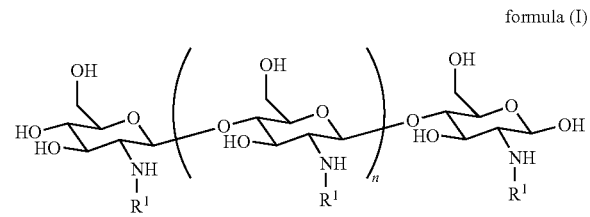

formula (I)

wherein:
n is an integer between 20 and 6000; and
each $R^1$ is independently selected for each occurrence from hydrogen, acetyl, and a group of formula (II):

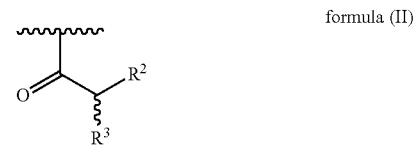

formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, R² is amino and R³ is an arginine side chain.

In one embodiment, R¹ is selected from one of the following:

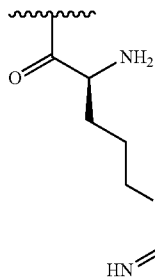 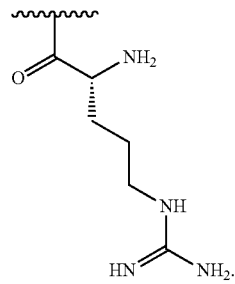

In one embodiment, R² is amino and R³ is a lysine side chain.

In one embodiment, R¹ is selected from one of the following:

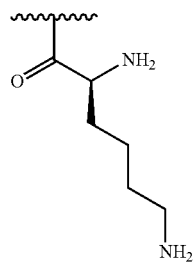 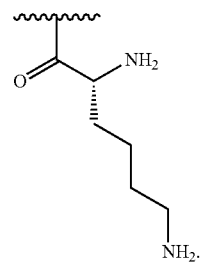

In one embodiment, R² is amino and R³ is a histidine side chain.

In one embodiment, R¹ is selected from one of the following:

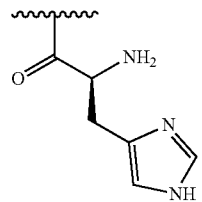 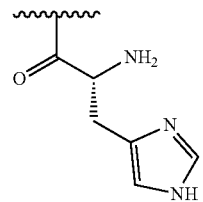

In one embodiment, at least 1% of R¹ substituents are selected from one of the following:

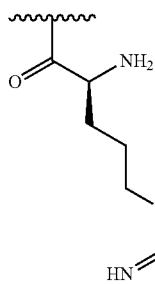 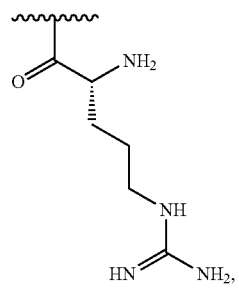

and at least 1% of R¹ substituents are selected from the following:

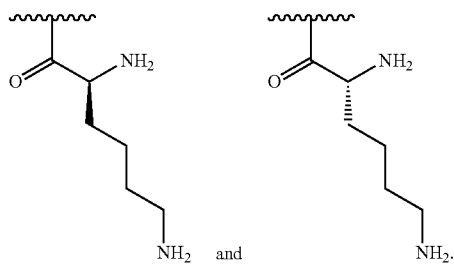 [SMILES: *C(=O)[C@@H](N)CCCCN ; *C(=O)[C@H](N)CCCCN]

In one embodiment, R² is amino and R³ is a substituted $C_1$-$C_6$ alkyl.

In one embodiment, R³ is $C_1$-$C_6$ alkyl substituted with an amino group.

In one embodiment, R³ is $C_1$ alkyl substituted with an amino group.

In one embodiment, R³ is $C_2$ alkyl substituted with an amino group.

In one embodiment, R³ is $C_3$ alkyl substituted with an amino group.

In one embodiment, R³ is $C_4$ alkyl substituted with an amino group.

In one embodiment, R³ is $C_5$ alkyl substituted with an amino group.

In one embodiment, R³ is $C_6$ alkyl substituted with an amino group.

In one embodiment, R¹ is selected from one of the following:

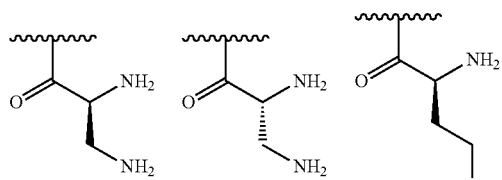

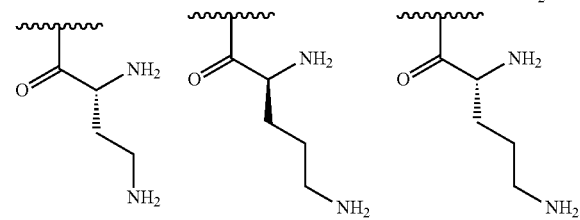

In one embodiment, R³ is $C_1$-$C_6$ alkyl substituted with a guanidino group.

In one embodiment, R³ is $C_1$ alkyl substituted with a guanidino group.

In one embodiment, R³ is $C_2$ alkyl substituted with a guanidino group.

In one embodiment, R³ is $C_3$ alkyl substituted with a guanidino group.

In one embodiment, R³ is $C_4$ alkyl substituted with a guanidino group.

In one embodiment, R³ is $C_5$ alkyl substituted with a guanidino group.

In one embodiment, R³ is $C_6$ alkyl substituted with a guanidino group.

In one embodiment, R¹ is selected from one of the following:

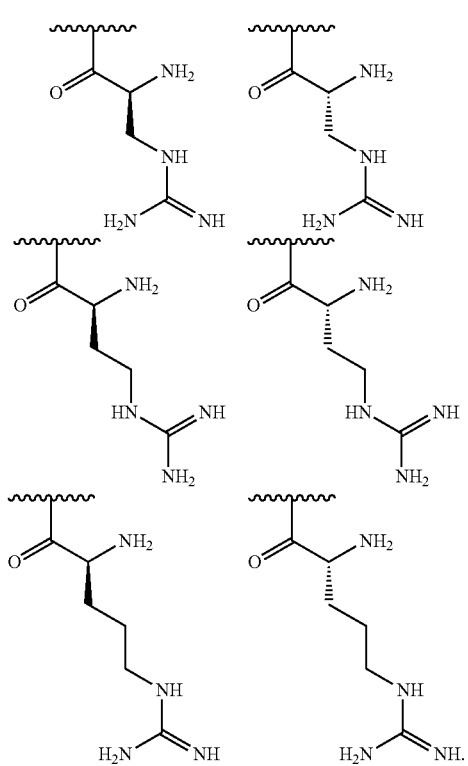

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

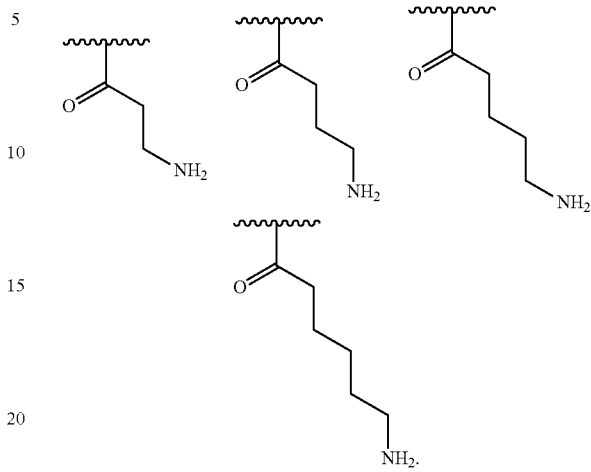

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

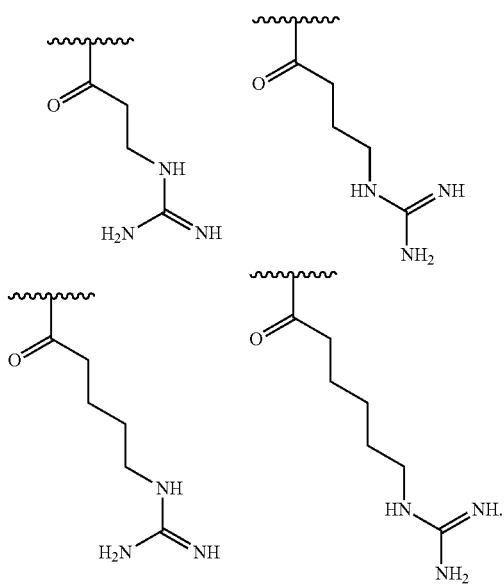

In one embodiment, at least 25% of $R^1$ substituents are H, at least 1% of $R^1$ substituents are acetyl, and at least 2% of R¹ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the kit has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the kit has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a kit comprising:
a soluble derivatized chitosan described herein; and
instructions to prevent or treat a gastrointestinal tract infection in a subject.

In one embodiment, the gastrointestinal tract infection is noninflammatory gastroenteritis, inflammatory gastroenteritis, invasive gastroenteritis, or nectrotic or necrotizing enteritis.

In one embodiment, the subject is infected with *Staphylococcus aureus, Bacillus cereus, Clostridium perfringens, Clostridium botulinum, Vibrio cholerae, Escherichia coli, Clostridium difficile, Vibrio parahemolyticus, Bacillus anthracis, Shigella* sp., *Salmonella* sp., *Campylobacter jejuni, Vibrion vulnificus, Yersinia* sp., *Francisella tularensis,* or *Helicobacter pylori.*

In one embodiment, the subject is infected with bacteria listed in Table 2.

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea,* or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the kit further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the kit further comprises an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the gastrointestinal tract.

In one embodiment, the subject is infected with planktonic bacteria.

In one embodiment, the derivatized chitosan reduces the viability of planktonic bacteria.

In one embodiment, the derivatized chitosan reduces colonization of the planktonic bacteria.

In one embodiment, the planktonic bacteria are clumped.

In one embodiment, the derivatized chitosan is administered orally, or enterally.

In one embodiment, the kit comprises an effective amount (e.g., therapeutically effective amount) of derivatized chitosan.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in duodenum.

In one embodiment, the derivatized chitosan is soluble in aqueous solution from about pH 2.0 to about pH 4.0, e.g., in stomach.

In one embodiment, the derivatized chitosan is soluble in aqueous solution from about pH 8.0 to about pH 8.5, e.g., in lower part of the gastrointestinal tract.

In one embodiment, the derivatized chitosan is active below pH 6 (e.g., in stomach and duodenum) or near or above pH 8 (e.g., in colon).

In one embodiment, the derivatized chitosan is active between pH 6 and pH 8.

In one embodiment, the derivatized chitosan is delivered e.g., by capsule, time release capsule, pH release capsule, as a powder dissolved in the digestive tract, or lozenge.

In one embodiment, the derivatized chitosan is delivered by mixing in food, or dissolved in any liquid, e.g., in a liquid formulation, e.g., daily or multiple times daily.

In one embodiment, the derivatized chitosan comprises a chitosan of the following formula (I):

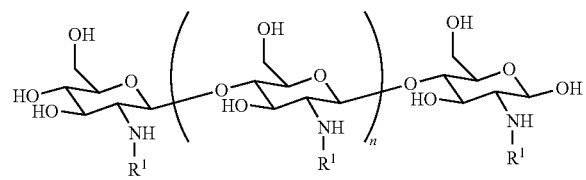

formula (I)

wherein:

n is an integer between 20 and 6000; and each $R^1$ is independently selected for each occurrence from hydrogen, acetyl, and a group of formula (II):

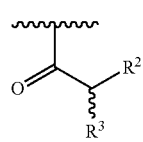

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

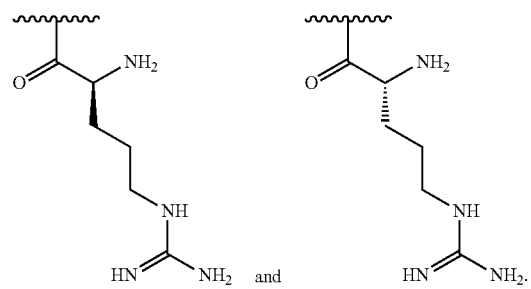 [SMILES: *C(=O)[C@@H](N)CCCNC(=N)N ; *C(=O)[C@H](N)CCCNC(=N)N]

In one embodiment, $R^2$ is amino and $R^3$ is a lysine side chain.

In one embodiment, $R^1$ is selected from one of the following:

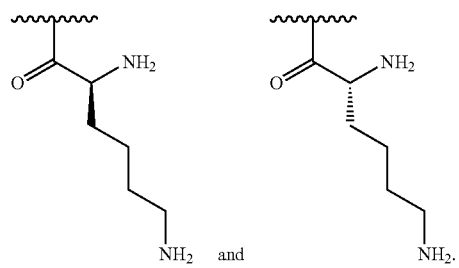 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

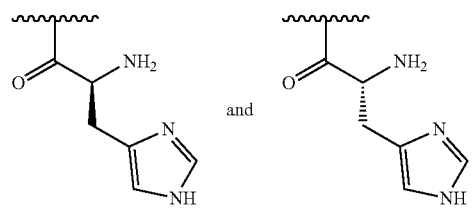

In one embodiment, at least 1% of $R^1$ substituents are selected from one of the following:

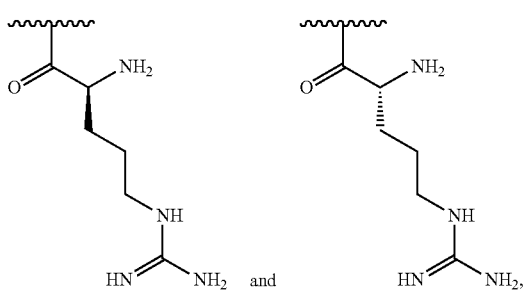 [SMILES: *C(=O)[C@@H](N)CCCNC(=N)N ; *C(=O)[C@H](N)CCCNC(=N)N]

and at least 1% of $R^1$ substituents are selected from the following:

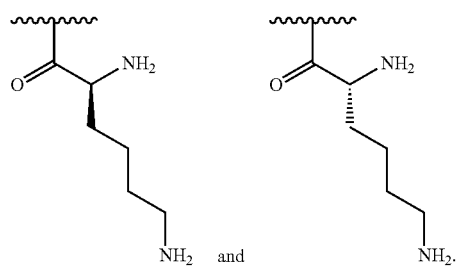 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

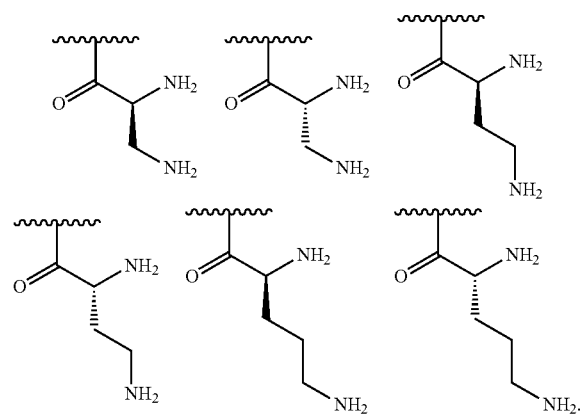

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

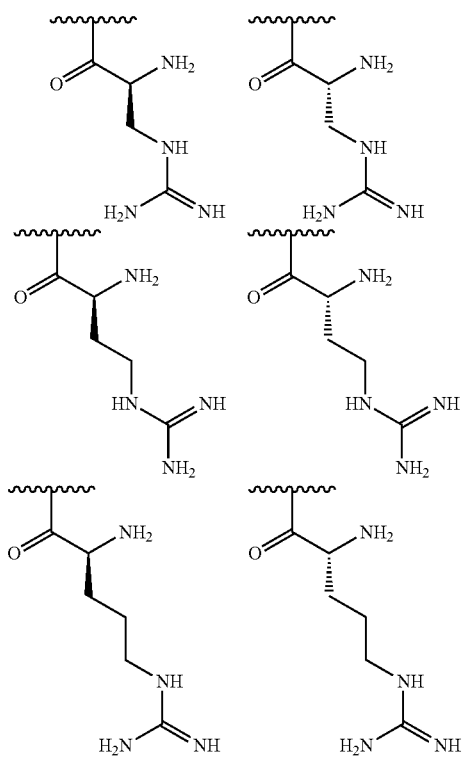

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is C alkyl substituted with an amino group.

In one embodiment, $R^3$ is $C_6$ alkyl substituted with an amino group.

In one embodiment, R¹ is selected from one of the following:

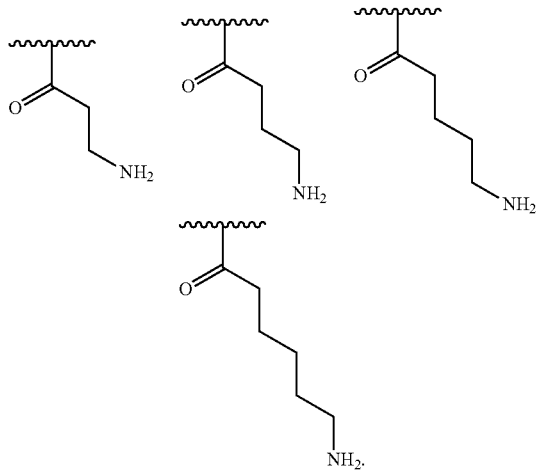

In one embodiment, R³ is $C_1$-$C_6$ alkyl substituted with a guanidino group.

In one embodiment, R³ is $C_1$ alkyl substituted with a guanidino group.

In one embodiment, R³ is $C_2$ alkyl substituted with a guanidino group.

In one embodiment, R³ is $C_3$ alkyl substituted with a guanidino group.

In one embodiment, R³ is $C_4$ alkyl substituted with a guanidino group.

In one embodiment, R³ is $C_6$ alkyl substituted with a guanidino group.

In one embodiment, R¹ is selected from one of the following:

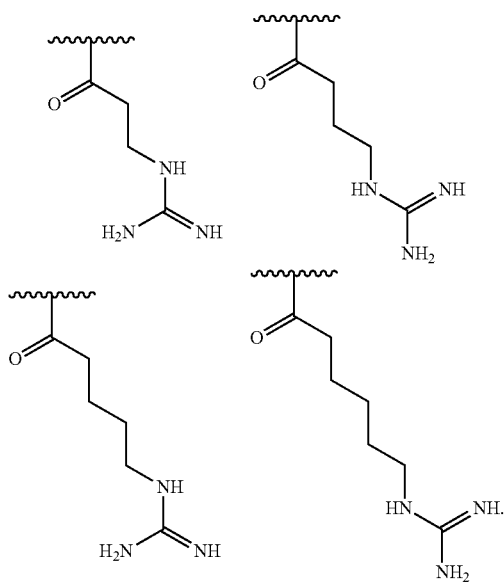

In one embodiment, at least 25% of R¹ substituents are H, at least 1% of R¹ substituents are acetyl, and at least 2% of R¹ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the kit has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the kit has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a medical device constructed to fit into the respiratory system of a subject, e.g., to contact nose or throat, the medical device comprising a soluble derivatized chitosan described herein. In one embodiment, the surface of the device is coated with a soluble derivatized chitosan.

In one embodiment, the subject has a bacterial infection, e.g., bacteria list in Table 3, e.g., *Pseudomonas aeruginosa*.

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea*, or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the medical device further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the medical device further comprises an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the respiratory system (e.g., airways, lung, throat, nose).

In one embodiment, the subject is infected with planktonic bacteria.

In one embodiment, the derivatized chitosan reduces the viability of planktonic bacteria.

In one embodiment, the derivatized chitosan reduces colonization of the planktonic bacteria.

In one embodiment, the planktonic bacteria are clumped, e.g., to facilitate removal by expectoration, lavage, or chest percussion.

In one embodiment, the derivatized chitosan is administered by inhalation (e.g., nebulizer, nasal spray, nasal swab, or sinus spray).

In one embodiment, the medical device comprises an effective amount (e.g., therapeutically effective amount) of derivatized chitosan.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan comprises a chitosan of the following formula (I):

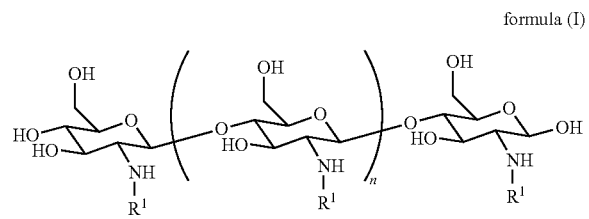

formula (I)

wherein:
n is an integer between 20 and 6000; and
each $R^1$ is independently selected for each occurrence from hydrogen, acetyl, and a group of formula (II):

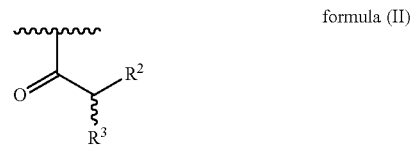

formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

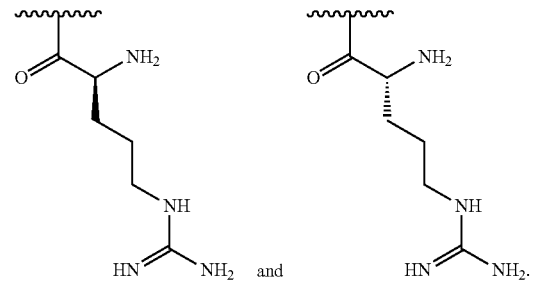 [SMILES: *C(=O)[C@@H](N)CCCNC(=N)N ; *C(=O)[C@H](N)CCCNC(=N)N]

In one embodiment, $R^2$ is amino and $R^3$ is a lysine side chain.

In one embodiment, $R^1$ is selected from one of the following:

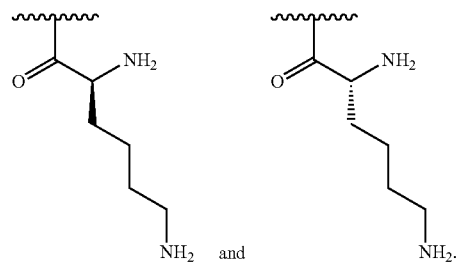 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

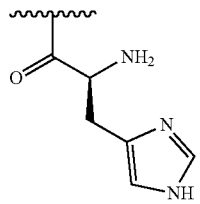 and 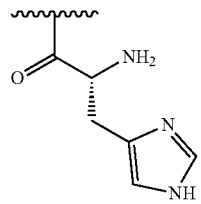.

In one embodiment, at least 1% of $R^1$ substituents are selected from one of the following:

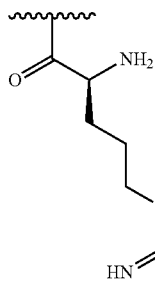 and 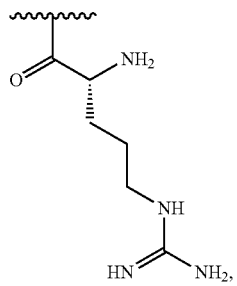, and at least 1% of $R^1$ substituents are selected from the following:

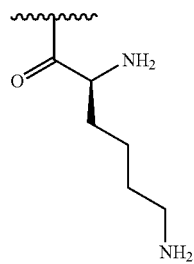 and 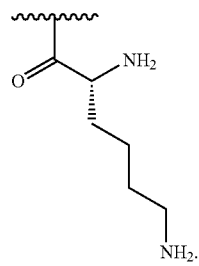.

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

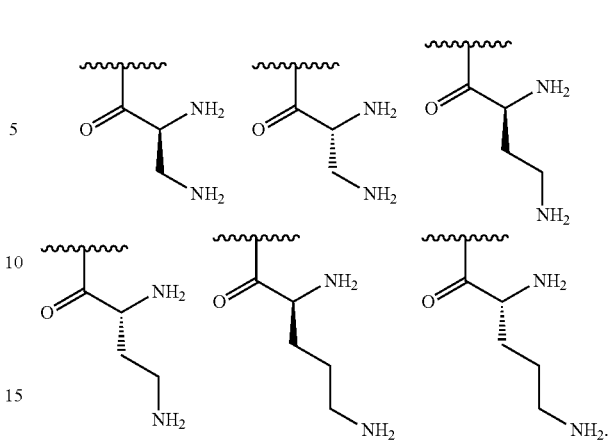

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

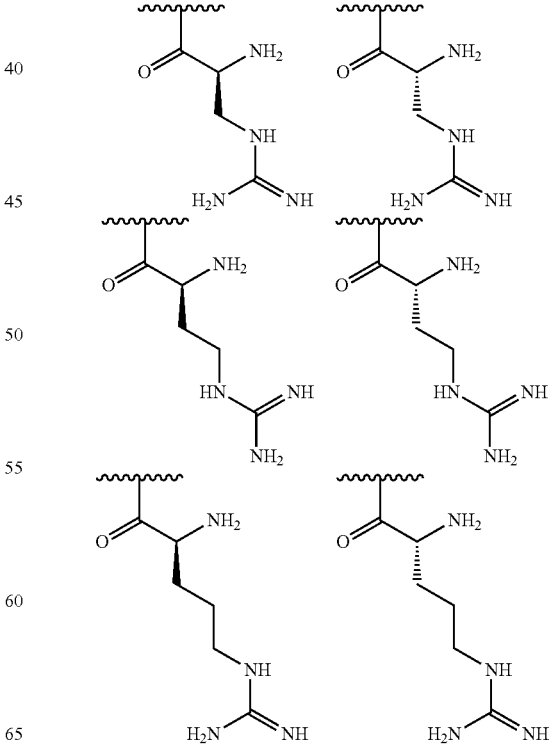

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

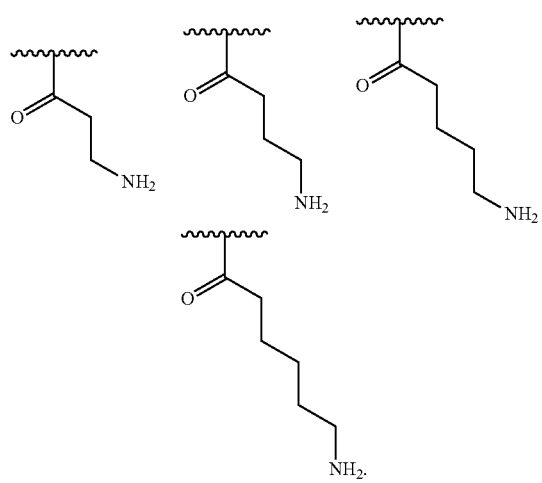

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

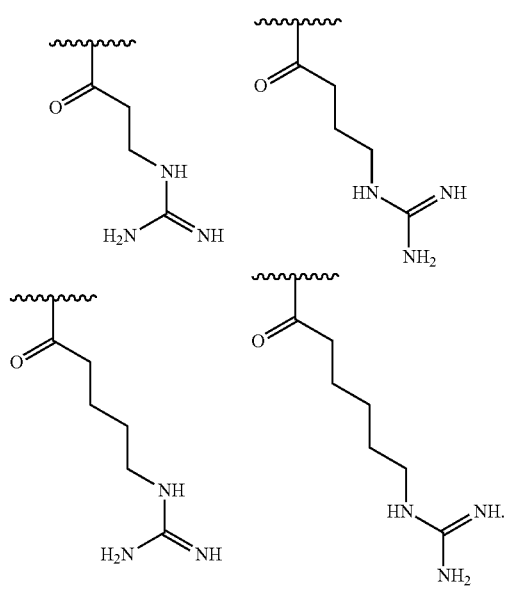

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment claim, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the medical device has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the medical device has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a nebulizer comprising a solution or powder of soluble derivatized chitosan described herein.

In one embodiment, the subject has a bacterial infection, e.g., bacteria list in Table 3, e.g., *Pseudomonas aeruginosa*.

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea*, or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the nebulizer further comprises an additional agent, e.g., a pharmaceutical agent, or a non-pharmaceutical agent (e.g., a non-toxic surfactant).

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the nebulizer further comprises an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the respiratory system (e.g., airways, lung, throat, nose).

In one embodiment, the subject is infected with planktonic bacteria.

In one embodiment, the derivatized chitosan reduces the viability of planktonic bacteria.

In one embodiment, the derivatized chitosan reduces colonization of the planktonic bacteria.

In one embodiment, the planktonic bacteria are clumped, e.g., to facilitate removal by expectoration, lavage, or chest percussion.

In one embodiment, the derivatized chitosan is administered by inhalation (e.g., nebulizer, nasal spray, nasal swab, or sinus spray).

In one embodiment, the nebulizer comprises an effective amount (e.g., therapeutically effective amount) of derivatized chitosan.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan comprises a chitosan of the following formula (I):

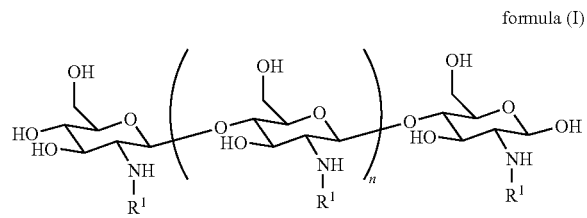

formula (I)

wherein:
n is an integer between 20 and 6000; and
each $R^1$ is independently selected for each occurrence from hydrogen, acetyl, and a group of formula (II):

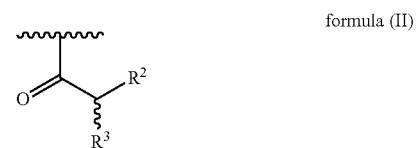

formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

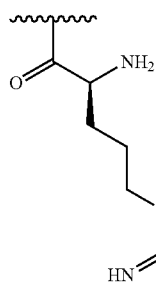 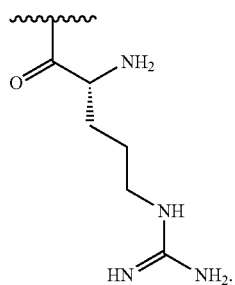

In one embodiment, $R^2$ is amino and $R^3$ is a lysine side chain.

In one embodiment, $R^1$ is selected from one of the following:

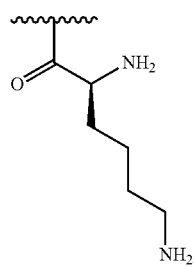 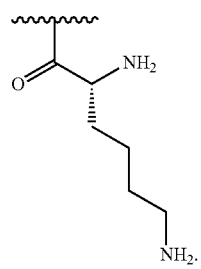

In one embodiment, $R^2$ is amino and $R^3$ is a histidine side chain.

In one embodiment, $R^1$ is selected from one of the following:

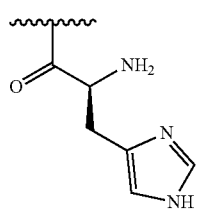 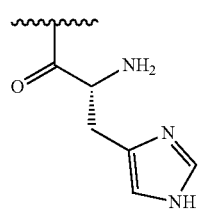

In one embodiment, at least 1% of $R^1$ substituents are selected from one of the following:

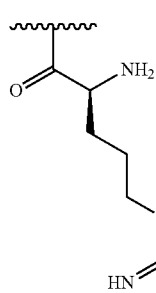 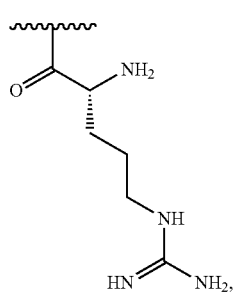

and at least 1% of $R^1$ substituents are selected from the following:

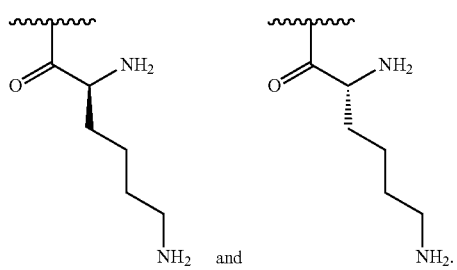 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

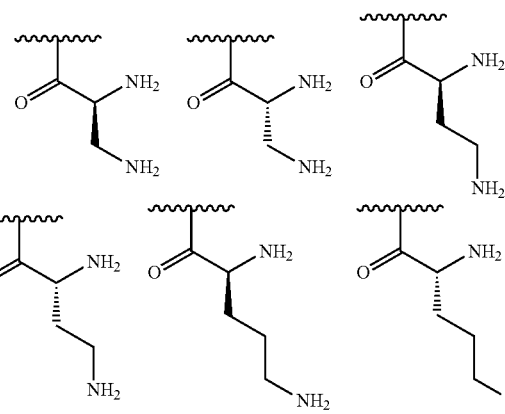

In one embodiment, $R^1$ is selected from one of the following:

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

101

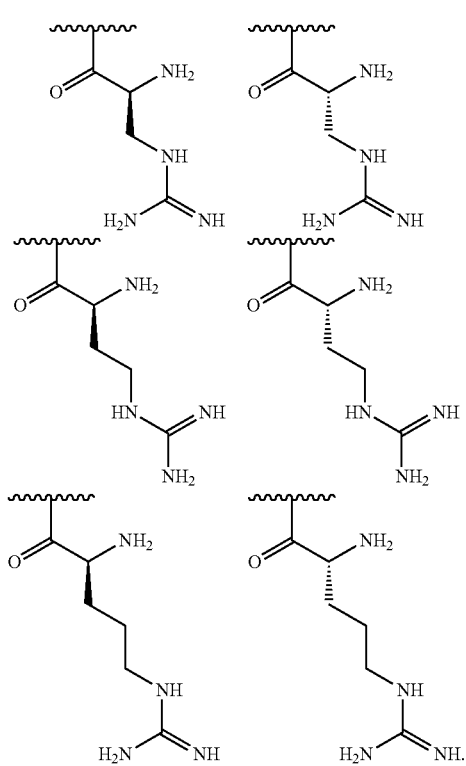

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

102

In one embodiment, $R^1$ is selected from one of the following:

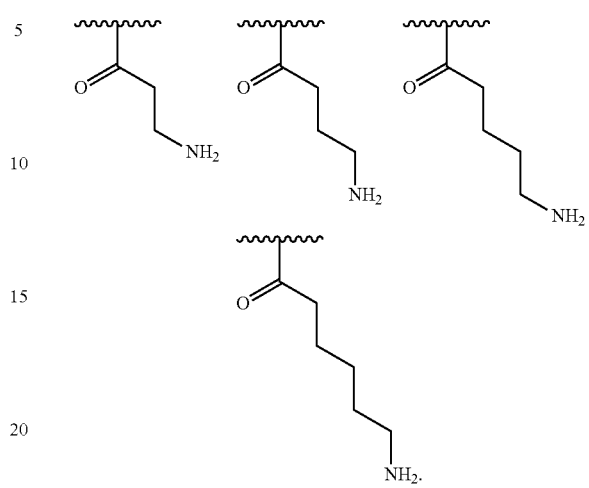

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

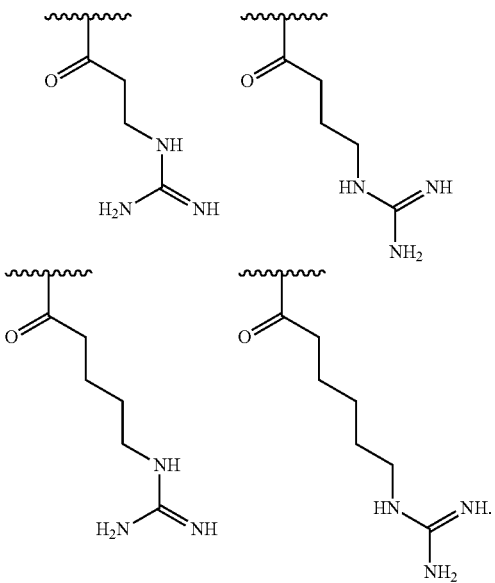

In one embodiment, at least 25% of $R^1$ substituents are H, at least 1% of $R^1$ substituents are acetyl, and at least 2% of R¹ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the nebulizer has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the nebulizer has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a medical device constructed to contact a wound of a subject, the medical device comprising a soluble derivatized chitosan described herein. In one embodiment, the surface of the device is coated with a soluble derivatized chitosan. Exemplary wounds include wounds on the skin of a subject, such as a wound that damages and/or penetrates the skin of a subject.

In one embodiment, the subject has a bacterial infection, e.g., bacteria list in Table 4.

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea*, or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the medical device further comprises an additional agent, e.g., a pharmaceutical agent, or a non-pharmaceutical agent (e.g., a non-toxic surfactant).

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the medical device further comprises an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the wound.

In one embodiment, the subject is infected with planktonic bacteria.

In one embodiment, the derivatized chitosan reduces the viability of planktonic bacteria.

In one embodiment, the derivatized chitosan reduces colonization of the planktonic bacteria.

In one embodiment, the derivatized chitosan is administered topically.

In one embodiment, the medical device comprises an effective amount (e.g., therapeutically effective amount) of derivatized chitosan.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in the wound.

In one embodiment, the derivatized chitosan comprises a chitosan of the following formula (I):

formula (I)

<chemical structure> wherein:

n is an integer between 20 and 6000; and each R¹ is independently selected for each occurrence from hydrogen, acetyl, and a group of formula (II):

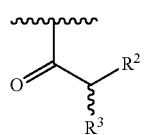

formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

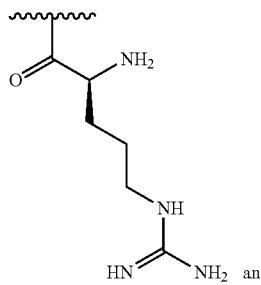 and 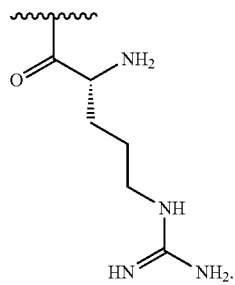

In one embodiment, $R^2$ is amino and $R^3$ is a lysine side chain.

In one embodiment, $R^1$ is selected from one of the following:

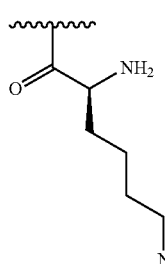 and 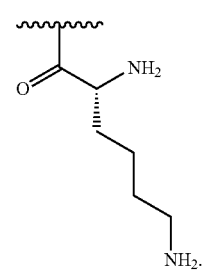

In one embodiment, $R^2$ is amino and $R^3$ is a histidine side chain.

In one embodiment, $R^1$ is selected from one of the following:

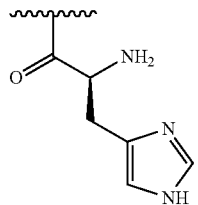 and 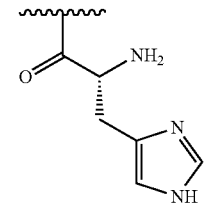

In one embodiment, at least 1% of $R^1$ substituents are selected from one of the following:

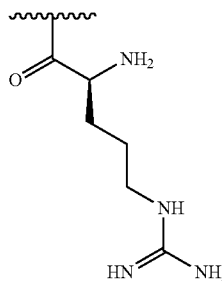 and 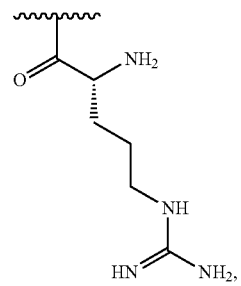

and at least 1% of $R^1$ substituents are selected from the following:

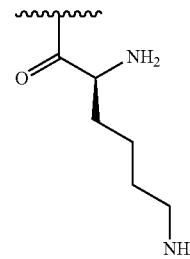 and 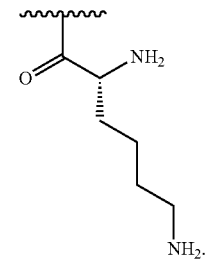

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^1$ is selected from one of the following:

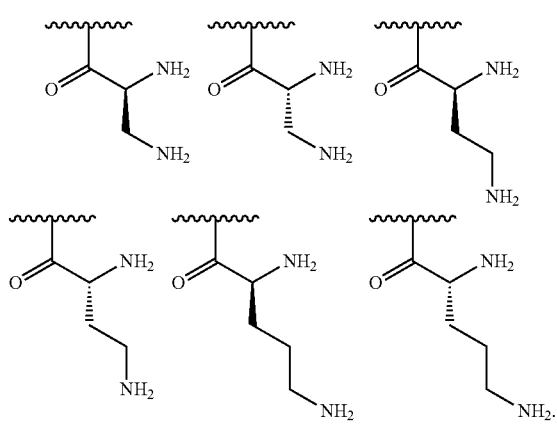

In one embodiment, $R^3$ is $C_1$-$C_6$ alkyl substituted with a guanidino group.
In one embodiment, $R^3$ is $C_1$ alkyl substituted with a guanidino group.
In one embodiment, $R^3$ is $C_2$ alkyl substituted with a guanidino group.
In one embodiment, $R^3$ is $C_3$ alkyl substituted with a guanidino group.
In one embodiment, $R^1$ is selected from one of the following:

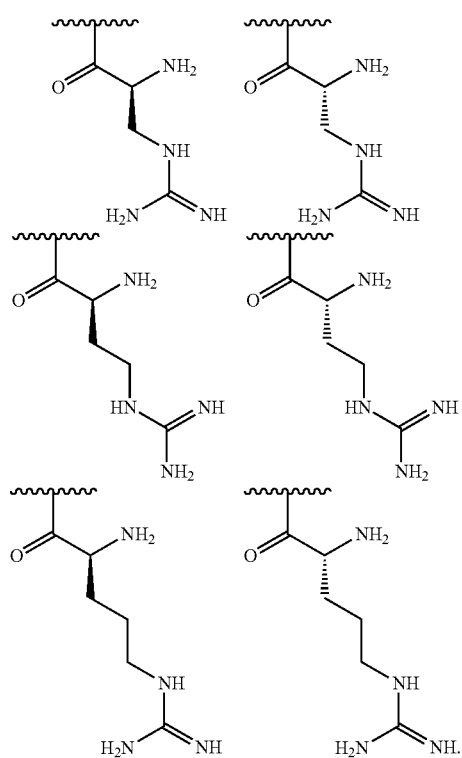

In one embodiment, $R^2$ is amino that is substituted with a nitrogen protecting group prior to substitution on chitosan and removed subsequent to substitution on chitosan.
In one embodiment, the nitrogen protecting group is tert-butyloxycarbonyl (Boc).
In one embodiment, in the synthetic process a nitrogen protecting group is used, which can provide an intermediate polymer having a nitrogen protecting group such as Boc.

In one embodiment, $R^2$ is amino.
In one embodiment, $R^2$ is hydrogen and $R^3$ is amino.
In one embodiment, $R^2$ is hydrogen and $R^3$ is guanidino.
In one embodiment, $R^2$ is hydrogen and $R^3$ is a substituted $C_1$-$C_6$ alkyl.
In one embodiment, $R^3$ is $C_1$-$C_6$ alkyl substituted with an amino group.
In one embodiment, $R^3$ is $C_1$ alkyl substituted with an amino group.
In one embodiment, $R^3$ is $C_2$ alkyl substituted with an amino group.
In one embodiment, $R^3$ is $C_3$ alkyl substituted with an amino group.
In one embodiment, $R^3$ is $C_4$ alkyl substituted with an amino group.
In one embodiment, $R^3$ is $C_5$ alkyl substituted with an amino group.
In one embodiment, $R^1$ is selected from one of the following:

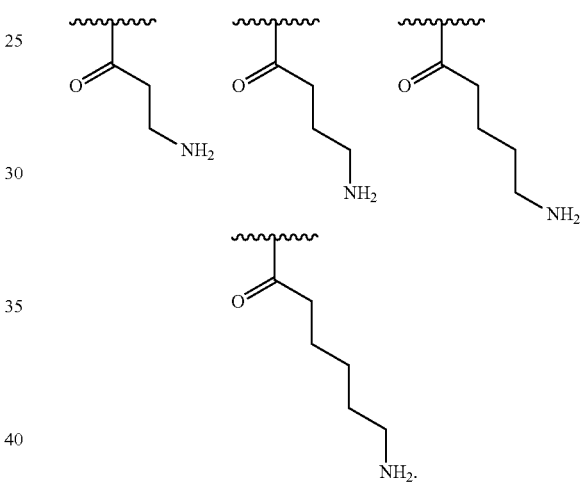

In one embodiment, $R^3$ is $C_1$-$C_6$ alkyl substituted with a guanidino group.
In one embodiment, $R^3$ is $C_1$ alkyl substituted with a guanidino group.
In one embodiment, $R^3$ is $C_2$ alkyl substituted with a guanidino group.
In one embodiment, $R^3$ is $C_3$ alkyl substituted with a guanidino group.
In one embodiment, $R^1$ is selected from one of the following:

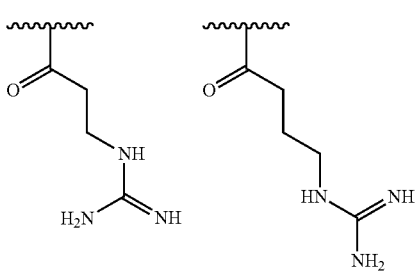

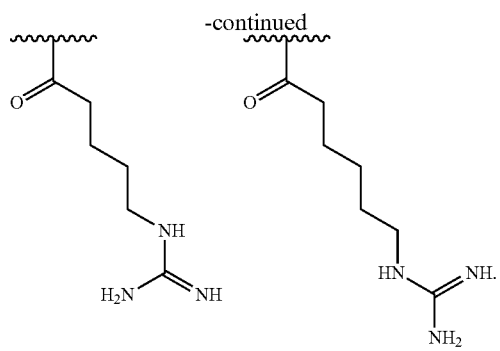

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In another aspect, the invention features a surface skin decontaminant comprising a derivatized chitosan described herein, e.g., used prior to surgery in a subject.

In one embodiment, the subject has a bacterial infection, e.g., bacteria list in Table 4.

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea*, or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the decontaminant further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the decontaminant further comprises an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the wound.

In one embodiment, the subject is infected with planktonic bacteria.

In one embodiment, the derivatized chitosan reduces the viability of planktonic bacteria.

In one embodiment, the derivatized chitosan reduces colonization of the planktonic bacteria.

In one embodiment, the derivatized chitosan is administered topically.

In one embodiment, the decontaminant comprises an effective amount (e.g., therapeutically effective amount) of derivatized chitosan.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in the wound.

In one embodiment, the derivatized chitosan comprises a chitosan of the following formula (I):

formula (I)

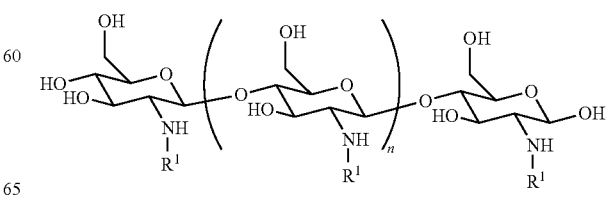

wherein:

n is an integer between 20 and 6000; and each $R^1$ is independently selected for each occurrence from hydrogen, acetyl, and a group of formula (II):

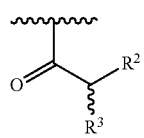

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

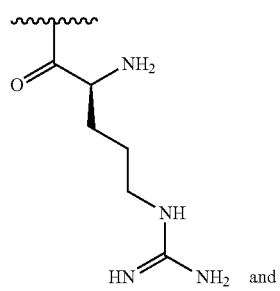 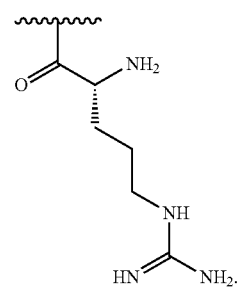

In one embodiment, $R^2$ is amino and $R^3$ is a lysine side chain.

In one embodiment, $R^1$ is selected from one of the following:

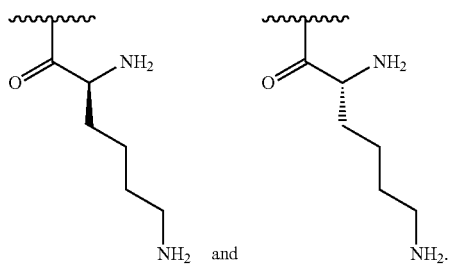

In one embodiment, $R^2$ is amino and $R^3$ is a histidine side chain.

In one embodiment, $R^1$ is selected from one of the following:

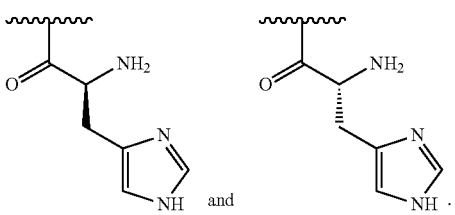 [SMILES: *C(=O)[C@@H](N)Cc1c[nH]cn1 ; *C(=O)[C@H](N)Cc1c[nH]cn1]

In one embodiment, at least 1% of $R^1$ substituents are selected from one of the following:

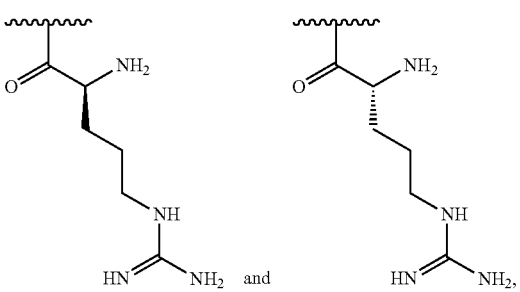 [SMILES: *C(=O)[C@@H](N)CCCNC(=N)N ; *C(=O)[C@H](N)CCCNC(=N)N]

and at least 1% of $R^1$ substituents are selected from the following:

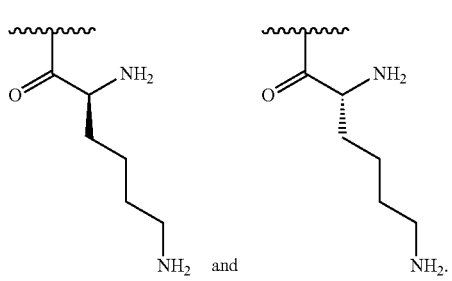 [SMILES: *C(=O)[C@@H](N)CCCCN ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

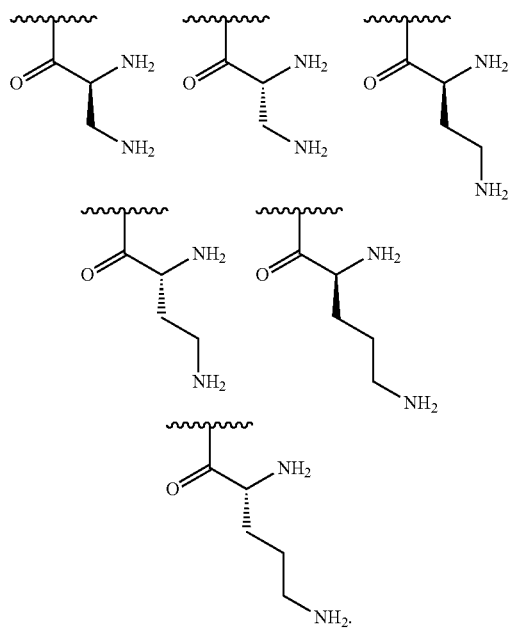

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

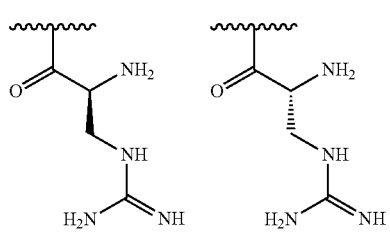

-continued

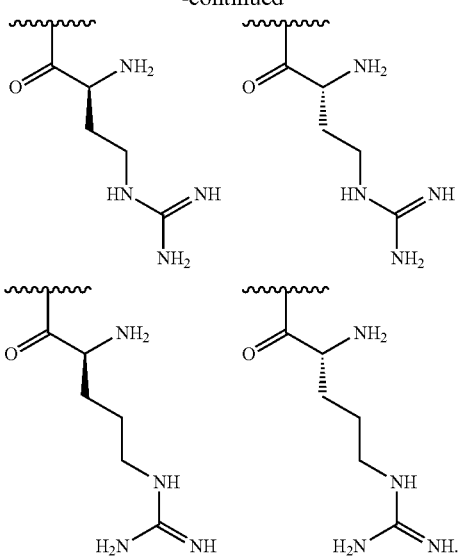

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is C alkyl substituted with an amino group.

In one embodiment, $R^3$ is $C_6$ alkyl substituted with an amino group.

In one embodiment, $R^1$ is selected from one of the following:

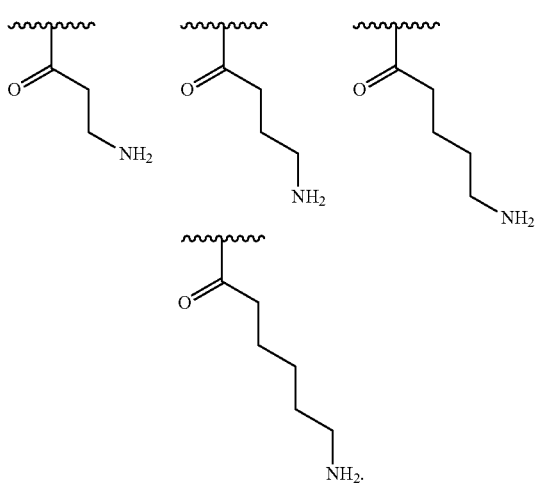

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

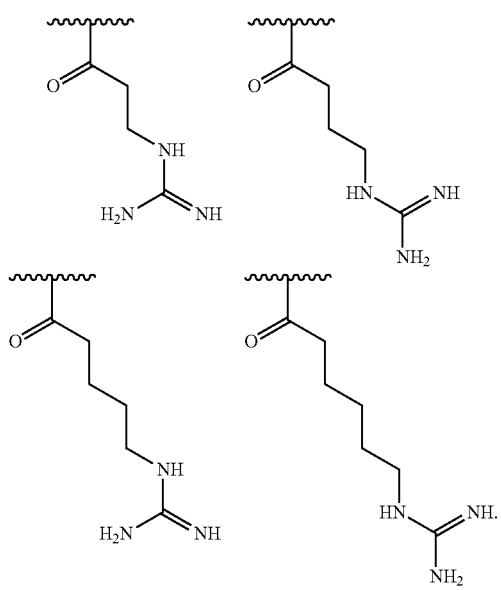

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the decontaminant has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the decontaminant has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a residual surface skin decontaminant comprising a derivatized chitosan described herein, e.g., used post surgery in a subject.

In one embodiment, the subject has a bacterial infection, e.g., bacteria list in Table 4.

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea,* or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the decontaminant further comprises an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the decontaminant further comprises an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the wound.

In one embodiment, the subject is infected with planktonic bacteria.

In one embodiment, the derivatized chitosan reduces the viability of planktonic bacteria.

In one embodiment, the derivatized chitosan reduces colonization of the planktonic bacteria.

In one embodiment, the derivatized chitosan is administered topically.

In one embodiment, the decontaminant comprises an effective amount (e.g., therapeutically effective amount) of derivatized chitosan.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in the wound.

In one embodiment, the derivatized chitosan comprises a chitosan of the following formula (I):

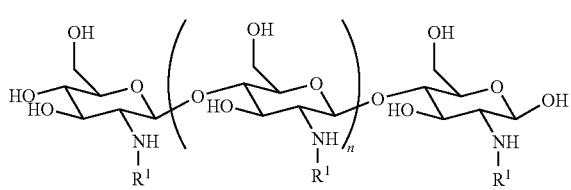

formula (I)

wherein:
n is an integer between 20 and 6000; and
each $R^1$ is independently selected for each occurrence from hydrogen, acetyl, and a group of formula (II):

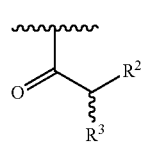

formula (II)

or $R^1$, when taken together with the nitrogen to which it is attached, forms a guanidine moiety, wherein $R^2$ is hydrogen or amino; and $R^3$ is amino, guanidino, $C_1$-$C_6$ alkyl substituted with an amino or guanidino moiety, or a natural or unnatural amino acid side chain, wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

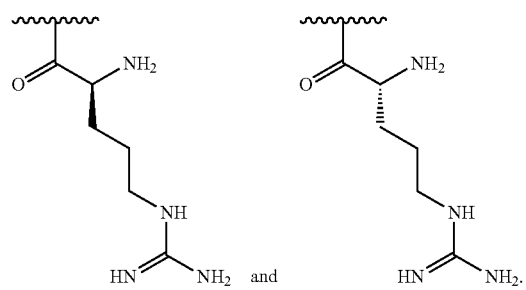

In one embodiment, $R^2$ is amino and $R^3$ is a lysine side chain.

In one embodiment, $R^1$ is selected from one of the following:

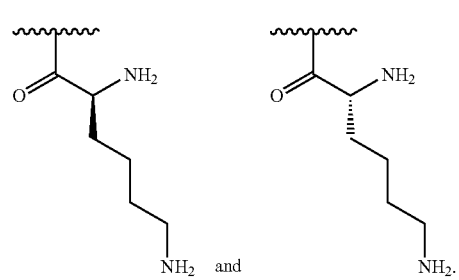 [SMILES: *C(=O)[C@@H](N)CCCCN ; *C(=O)[C@H](N)CCCCN]

In one embodiment, $R^2$ is amino and $R^3$ is a histidine side chain.

In one embodiment, $R^1$ is selected from one of the following:

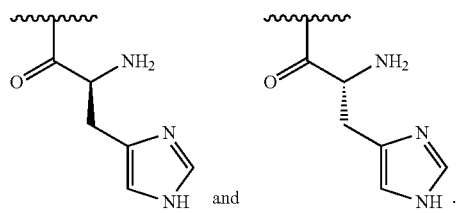 [SMILES: *C(=O)[C@@H](N)Cc1c[nH]cn1 ; *C(=O)[C@H](N)Cc1c[nH]cn1]

In one embodiment, at least 1% of $R^1$ substituents are selected from one of the following:

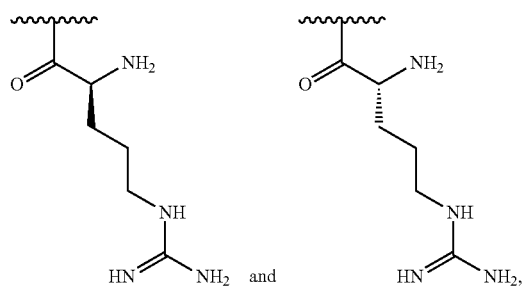 [SMILES: *C(=O)[C@@H](N)CCCNC(=N)N ; *C(=O)[C@H](N)CCCNC(=N)N]

and at least 1% of $R^1$ substituents are selected from the following:

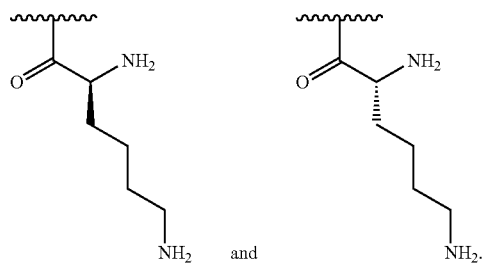 [SMILES: *C(=O)[C@@H](N)CCCCN ; "and" ; *C(=O)[C@H](N)CCCCN]

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

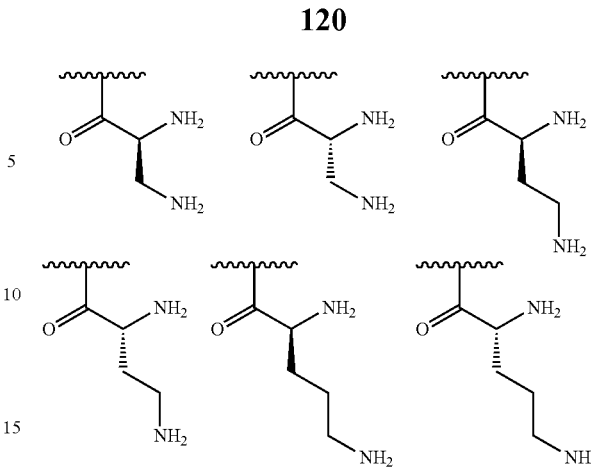

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

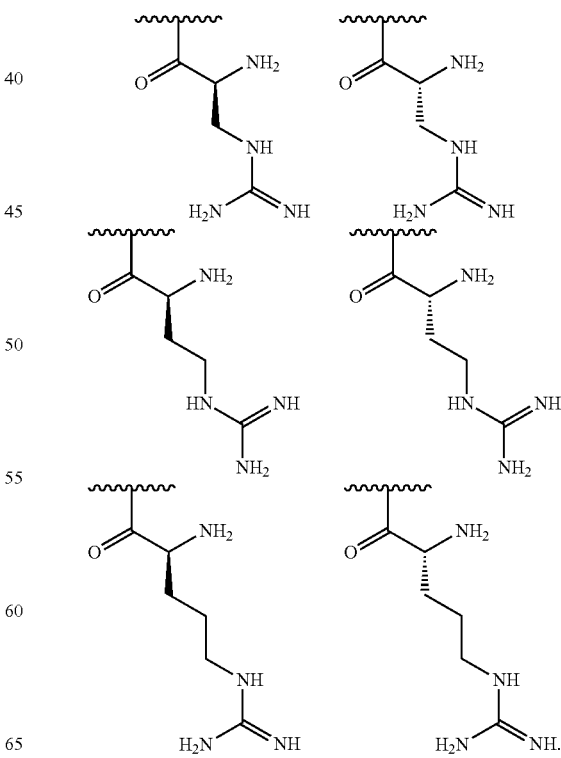

In one embodiment, $R^2$ is amino that is substituted with a nitrogen protecting group prior to substitution on chitosan and removed subsequent to substitution on chitosan.

In one embodiment, the nitrogen protecting group is tert-butyloxycarbonyl (Boc).

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

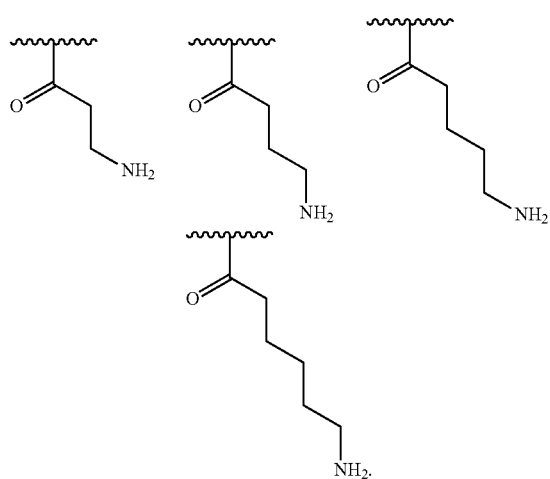

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

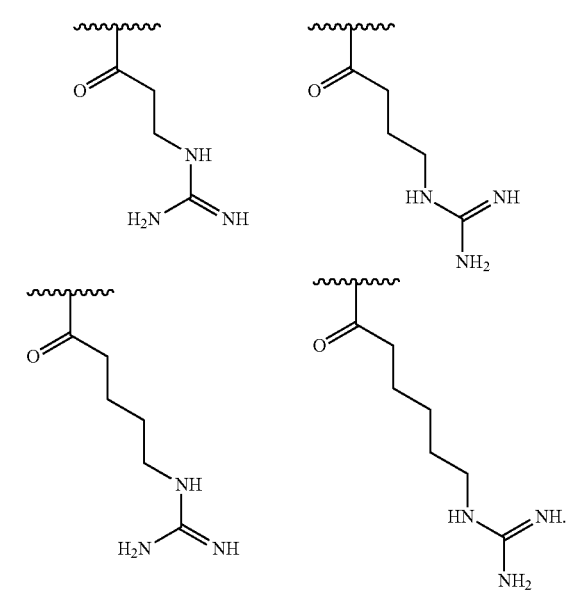

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the decontaminant has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the decontaminant has less than about 20%, 15%, 10%, 5%, 2%, or 1%, or is substantially free, of a chitosan polymer having a molecular weight of less than 15,000 Da, 10,000 Da, or 5,000 Da.

In another aspect, the invention features a method of treating a surface skin in a subject, the method comprising:
administering to the subject an effective amount of a composition comprising a soluble derivatized chitosan, thereby treating the surface skin.

In one embodiment, the skin is treated before a surgery.

In one embodiment, the skin is treated after a surgery.

In one embodiment, the subject has a bacterial infection, e.g., bacteria list in Table 4.

In one embodiment, the subject comprises at least one biofilm.

In one embodiment, exopolysaccharides (EPS) of the biolim comprises alginate and/or polysaccharide synthesis locus (Psl) (e.g., in *Pseudomonas aeruginosa*); acidic polysaccharide (e.g., in *Burkholderia cepacia*); collanic acid, poly-β-1,6-GlcNAc (PGA) or cellulose (e.g., in *Escherichia coli*); cellulose (e.g., in *Salmonella*); N-acetylglucosamine (GlcNAc), D-mannose, 6-deoxy-D-galactose and D-galactose (e.g., in *Vibrio cholerae*); polysaccharide intercellular adhesion (PIA) (e.g., in *Staphylococcus*); glucose and mannose rich component (e.g., in *Bacillus subtilis*); mannose polysaccharide (e.g., in *Prevotella intermedia, Capnocytophaga ochracea,* or *Prevotella nigrescens*).

In one embodiment, the biofilm is associated with actin and/or DNA released from bacteria or cells such as neutrophils.

In one embodiment, the viscosity (e.g., apparent viscosity) of the biofilm is reduced by at least 10, 20, 30, 40, 50, 60, 70, 80, 90, 95, or 99%, compared to the biofilm that has not been contacted with the derivatized chitosan.

In one embodiment, the viscosity (e.g., apparent viscosity) of the biofilm is reduced by at least 1, 2, 5, 10, 50, 100, 200, 500, or 1000 fold, compared to the biofilm that has not been contacted with the derivatized chitosan.

In one embodiment, the biofilm is partially dissolved, e.g., at least 10, 20, 30, 40, 50, 60, 70, 80, 90, 95, 99, 99.9, or 99.999% of the biofilm is dissolved, compared to the biofilm that has not been contacted with the derivatized chitosan.

In one embodiment, the method further comprises administering an additional agent, e.g., a pharmaceutical agent, or a non-pharmaceutical agent (e.g., a non-toxic surfactant). In one embodiment, the second agent comprises another chitosan derivative, e.g., another chitosan derivative described herein.

In one embodiment, the second agent is administered in a dosage to achieve a synergistic effect.

In one embodiment, the second agent is administered together with the soluble derivatized chitosan (e.g., in the same derivatized chitosan or dosage form).

In one embodiment, the method further comprises administering an antibiotic, anti-inflammatory, or mucolytic (expectorant) compound to a subject in conjunction with, prior to or subsequent to the administration of the derivatized chitosan.

In one embodiment, the antibiotic, anti-inflammatory, or mucolytic (expectorant) compound is administered in a dosage to achieve a synergistic effect.

In one embodiment, the biofilm is in the wound.

In one embodiment, the subject is infected with planktonic bacteria.

In one embodiment, the derivatized chitosan reduces the viability of planktonic bacteria.

In one embodiment, the derivatized chitosan reduces colonization of the planktonic bacteria.

In one embodiment, the derivatized chitosan is administered topically.

In one embodiment, the effective amount is therapeutically effective amount.

In one embodiment, the derivatized chitosan is soluble in aqueous solution from about pH 6.8 to about pH 7.4.

In one embodiment, the derivatized chitosan is soluble in aqueous solution from about pH 3 to about pH 9.

In one embodiment, the derivatized chitosan is soluble in aqueous solution from about pH 5.0 to about pH 6.0, e.g., in the wound.

In one embodiment, the derivatized chitosan comprises a chitosan of the following formula (I):

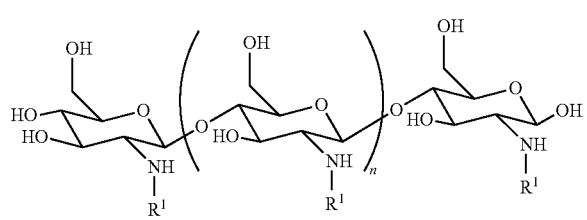

formula (I)

wherein:
n is an integer between 20 and 6000; and
each $R^1$ is independently selected for each occurrence from hydrogen, acetyl, and a group of formula (II):

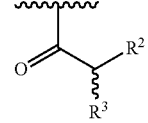

formula (II)

or $R^1$, when taken together with the nitrogen to which it is attached, forms a guanidine moiety,
wherein $R^2$ is hydrogen or amino; and
$R^3$ is amino, guanidino, $C_1$-$C_6$ alkyl substituted with an amino or guanidino moiety, or a natural or unnatural amino acid side chain,
wherein at least 25% of $R^1$ substituents are H, at least 1% of $R^1$ substituents are acetyl, and at least 2% of $R^1$ substituents are a group of formula (II).

In one embodiment, between 25-95% of $R^1$ substituents are hydrogen.

In one embodiment, between 55-90% of $R^1$ substituents are hydrogen.

In one embodiment, between 1-50% of $R^1$ substituents are acetyl.

In one embodiment, between 4-20% of $R^1$ substituents are acetyl.

In one embodiment, between 2-50% of $R^1$ substituents are a group of formula (II).

In one embodiment, between 4-30% of $R^1$ substituents are a group of formula (II).

In one embodiment, 55-90% of $R^1$ substituents are hydrogen, 4-20% of $R^1$ substituents are acetyl, 4-30% of $R^1$ substituents are a group of formula (II).

In one embodiment, $R^2$ is amino and $R^3$ is an arginine side chain.

In one embodiment, $R^1$ is selected from one of the following:

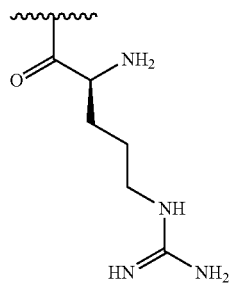 and 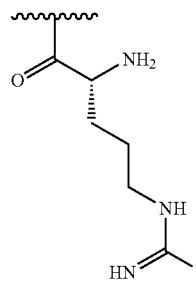

In one embodiment, $R^2$ is amino and $R^3$ is a lysine side chain.

In one embodiment, $R^1$ is selected from one of the following:

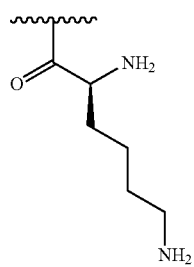 and 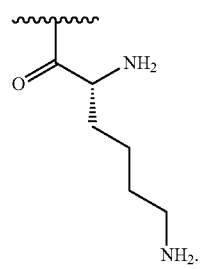

In one embodiment, $R^2$ is amino and $R^3$ is a histidine side chain.

In one embodiment, $R^1$ is selected from one of the following:

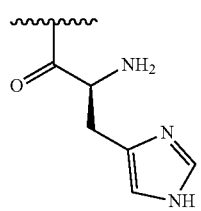 and 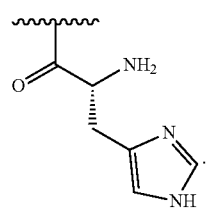

In one embodiment, at least 1% of $R^1$ substituents are selected from one of the following:

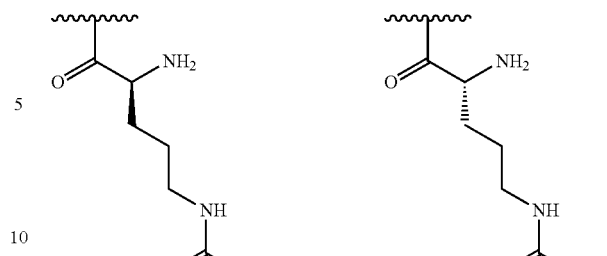 and and at least 1% of $R^1$ substituents are selected from the following:

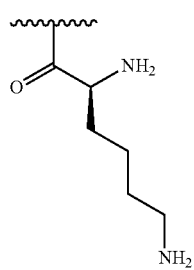 and 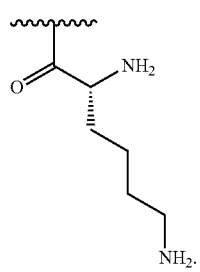

In one embodiment, $R^2$ is amino and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

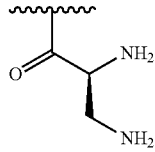 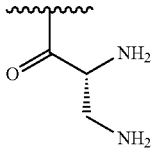 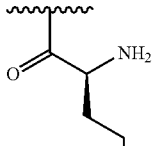

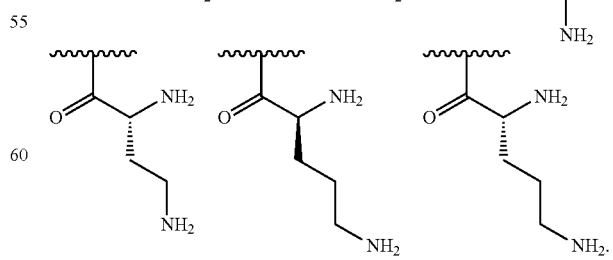

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

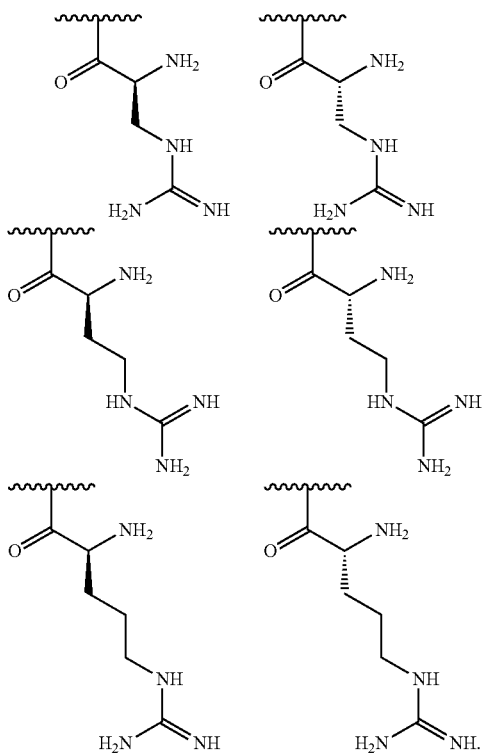

In one embodiment, $R^2$ is amino that is substituted with a nitrogen protecting group prior to substitution on chitosan and removed subsequent to substitution on chitosan.

In one embodiment, the derivatized chitosan is made by reacting a chitosan (e.g., a free amino group of one or more of glucosamine monomers of the chitosan) with an amino acid (e.g., a carboxylic acid moiety of the amino acid) wherein the amino group of the amino acid is protected by a protecting group (e.g., Boc). The protecting group can be removed, e.g., by exposure to acid of pH<3, after the synthesis.

In one embodiment, the nitrogen protecting group is tert-butyloxycarbonyl (Boc).

In one embodiment, in the synthetic process a nitrogen protecting group is used, which can provide an intermediate polymer having a nitrogen protecting group such as Boc.

In one embodiment, $R^2$ is amino.

In one embodiment, $R^2$ is hydrogen and $R^3$ is amino.

In one embodiment, $R^2$ is hydrogen and $R^3$ is guanidino.

In one embodiment, $R^2$ is hydrogen and $R^3$ is a substituted $C_1$-$C_6$ alkyl.

In one embodiment, $R^3$ is $C_1$-$C_6$ alkyl substituted with an amino group.

In one embodiment, $R^3$ is $C_1$ alkyl substituted with an amino group.

In one embodiment, $R^3$ is $C_2$ alkyl substituted with an amino group.

In one embodiment, $R^3$ is $C_3$ alkyl substituted with an amino group.

In one embodiment, $R^3$ is $C_4$ alkyl substituted with an amino group.

In one embodiment, $R^3$ is $C_5$ alkyl substituted with an amino group.

In one embodiment, $R^3$ is $C_6$ alkyl substituted with an amino group.

In one embodiment, $R^1$ is selected from one of the following:

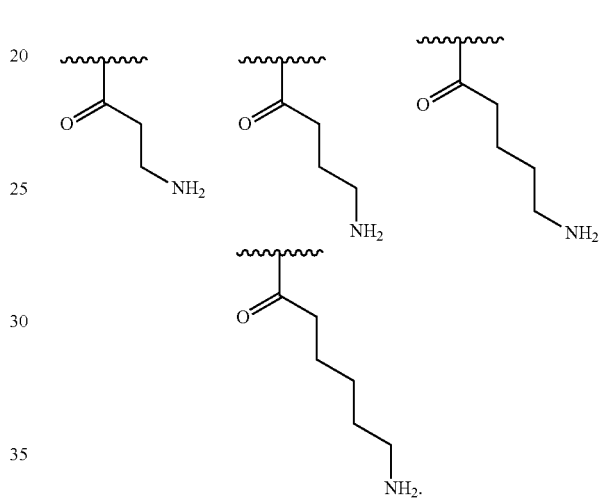

In one embodiment, $R^3$ is $C_1$-$C_6$ alkyl substituted with a guanidino group.

In one embodiment, $R^3$ is $C_1$ alkyl substituted with a guanidino group.

In one embodiment, $R^3$ is $C_2$ alkyl substituted with a guanidino group.

In one embodiment, $R^3$ is $C_3$ alkyl substituted with a guanidino group.

In one embodiment, $R^3$ is $C_4$ alkyl substituted with a guanidino group.

In one embodiment, $R^3$ is $C_5$ alkyl substituted with a guanidino group.

In one embodiment, $R^3$ is $C_6$ alkyl substituted with a guanidino group.

In one embodiment, $R^1$ is selected from one of the following:

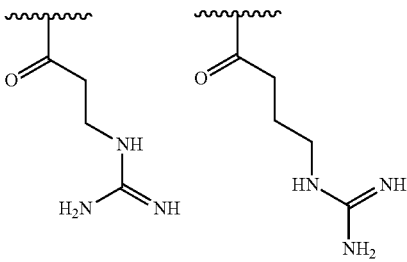

-continued

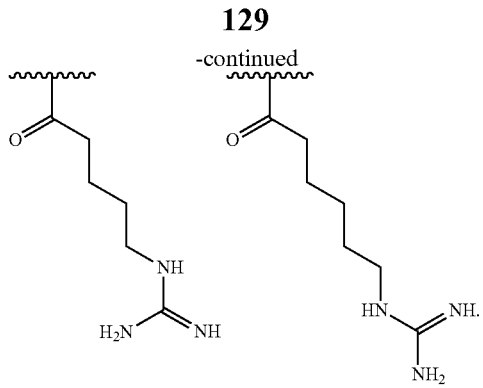

In one embodiment, at least 25% of $R^1$ substituents are H, at least 1% of $R^1$ substituents are acetyl, and at least 2% of $R^1$ substituents independently selected from any of the formulae specifically shown above.

In one embodiment, the chitosan of formula (I) may be further derivatized on the free hydroxyl moieties.

In one embodiment, the molecular weight of the derivatized chitosan is between 5,000 and 1,000,000 Da.

In one embodiment, the molecular weight of the derivatized chitosan is between 5,000 and 350,000 Da.

In one embodiment, the molecular weight of the derivatized chitosan is between 10,000 and 150,000 Da.

In one embodiment, the molecular weight of the derivatized chitosan is between 15,000 and 100,000 Da.

In one embodiment, the molecular weight of the derivatized chitosan is between 15,000 and 50,000 Da.

In one embodiment, the molecular weight of the derivatized chitosan is between 20,000 and 40,000 Da.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.5 and 2.0.

In one embodiment, the derivatized chitosan is substantially free of other impurities, e.g., salt, e.g., NaCl.

In one embodiment, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In one embodiment, the composition has less than about 20%, 15%, 10%, 5%, 2%, or 1%, or is substantially free, of a chitosan polymer having a molecular weight of less than 15,000 Da, 10,000 Da, or 5,000 Da.

DETAILED DESCRIPTION

Figure 1B:
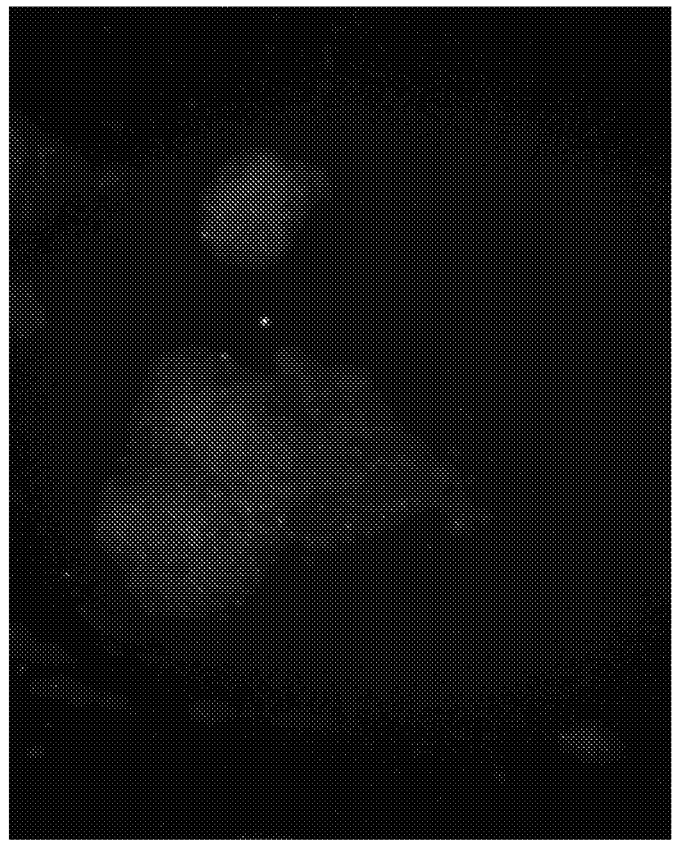
FIG. 1B shows the clumping of Gram negative *Pseudomonas aeruginosa* strain PA01 after 1 minute of exposure to chitosan-arginine (24 kDa, 28% functionalized, 83% DDA, 1.54 PDI) at 200× magnification.

Described herein are methods and compositions that contain a soluble chitosan or chitosan derivative. The compositions can be used, for example, for reducing preformed biofilms, preventing formation of biofilms, treating or preventing complications of cystic fibrosis, or treating or preventing gastrointestinal infections. In some embodiments, a composition described herein can result in the clumping of bacteria, for example, to a soluble chitosan or chitosan derivative. The clumped bacteria can be discarded, for example, expirated by a subject, or can be ingested.

In some embodiments, the soluble chitosans or derivatized chitosans exhibit one or more of the following characteristics: for example, long shelf lives, ability to be stored as a dry powder, or ability to dissolve in water, saline, or other neutral solution (e.g., in the human body) and to be dispersed as needed (e.g., as a solid, semisolid, or liquid composition). Exemplary compounds include, but are not limited to soluble chitosan compounds, chitosan-arginine compounds, chitosan-guanidine compounds, chitosan-unnatural amino acid compounds, chitosan-acid-amine compounds, chitosan-natural amino acid compounds, and co-derivatives of the just described compounds and the salts thereof. These compounds and their antimicrobial activity are disclosed in U.S. patent application Ser. Nos. 11/657,382 and 11/985,057, which is herein incorporated by reference. Exemplary compounds also include neutral chitosan compounds (e.g., monosaccharide-containing chitosan compounds, chitosan-lactobionic acid compounds, and chitosan-glycolic acid compounds), and co-derivatives of these compounds and the salts thereof.

Biofilm

Methods and compositions described herein can be used to disrupt (e.g., reduce the viscosity of, or dissolve) a preformed biofilm in a subject. As used herein, the term "dissolve" or "dissolving" means breaking up cohesion in a preformed biofilm such that some or all can be rinsed, flushed or washed away.

A biofilm is a structured community of microorganisms encapsulated within a self-developed polymeric matrix and adherent to a living or inert surface. Biofilms are also often characterized by surface attachment, structural heterogeneity, genetic diversity, complex community interactions, and an extracellular matrix of polymeric substances.

Formation of a biofilm begins with the attachment of free-floating microorganisms to a surface. Colonization begins with adherence to the surface initially through weak, reversible van der Waals forces. If the colonizing bacteria are not immediately separated from the surface, they can anchor themselves more permanently using cell adhesion structures such as pili. The first colonizing bacteria facilitate the arrival of other cells by providing more diverse adhesion sites and beginning to build the matrix that holds the biofilm together. Once colonization has begun, the biofilm grows through a combination of cell division and recruitment. The final stage of biofilm formation is known as development, and is the stage in which the biofilm is established and may only change in shape and size. This development of biofilm environment and communication pathway allows for the cells to become more antibiotic resistant.

Biofilms can contain many different types of microorganisms, e.g. bacteria, archaea, protozoa, fungi and algae; each group performing specialized metabolic functions. Microorganisms can also form monospecies films.

The biofilm is held together and protected by a matrix of excreted polymeric compounds called Extracellular polymeric substance (EPS). This matrix protects the cells within it and facilitates communication among them through biochemical signals.

Bacteria living in a biofilm have different properties from free-floating bacteria of the same species, as the dense and protected environment of the film allows them to cooperate and interact in various ways. One benefit of this environment to the bacteria is increased resistance to detergents and antibiotics, as the dense extracellular matrix and the outer layer of cells protect the interior of the community.

Exemplary bacteria associated with biofilm include Gram-positive (e.g., *Staphylococcus aureus* (e.g., strain MW-2), *Streptococcus mutans, Clostridium perfringens, Streptococcus pyogenes* (GAS), *Clostridium difficile* and *Streptococcus sanguis*) and Gram-negative bacteria (*E. coli* (e.g., strain O:157H:7), *Shigella flexneri, Salmonella typhimurium, Acinetobacter baumannii, Pseudomonas aeruginosa* and *Legionella* bacteria (e.g., *L. pneumophila*)).

Exemplary oral, gastro and pulmonary bacteria are listed in Tables 1-3, respectively.

TABLE 1

Exemplary oral bacteria strains

| Strain (oral) | Description |
| --- | --- |
| Streptococcus mutans | Causes cavities |
| Streptococcus sanguinis | Causes cavities |
| Lactobacillus acidophilus | Causes cavities |
| Actinomyces viscosus | Causes actinomysis/oral infection |

TABLE 2

Exemplary gastro bacteria strains

| Strain (gastro) | Description |
| --- | --- |
| Escherichia coli | Shiga-like toxin producer, such as O157:H7 |
| Shigella flexneri | Shiga toxin producer |
| Salmonella typhimurium | Causes gastroenteritis, food poisoning |
| Clostridium difficile | Causes food poisoning, forms spores |
| Enterococcus faecalis | Vancomycin resistant, gastrointestinal |
| Helicobacter pylori | Gastrointestinal ulcers |
| Bacillus subtilis | Spore former |
| Listeria monocytogenes | Intracellular pathogen |
| Campylobacter jejuni | Causes food poisoning, non-spore former |
| Staphylococcus aureus | Gastroenteritis |
| Klebsiella pneumoniae | Causes pneumonia, many drug resistant strains |

TABLE 3

Exemplary pulmonary bacteria strains

| Strain (Pulmonary) | Characteristics |
| --- | --- |
| Staphylococcus aureus | Broadly infective, wounds, body fluids, tissue, pulmonary, highly multi-durg resistant strains including MRSA and mupirocin resistant MRSA |
| Pseudomonas aeruginosa | Causes pneumonia, primary pathogen in patients with cystic fibrosis, many MDR strains, forms thick biofilms |
| Burkholdaria cepacia genomvar cenocepatia | Virulent pathogen in lungs of patients with cystic fibrosis |
| Acinetobacter baumannii | Slow-growing, colonization, causes penumonia |
| Streptococcus pneumoniae | Aquatic bacterium, colonizes breathing and feeding tubes |
| Stenotrophomonas maltophilia | Similar to *pseudomonas*, pulmonary infections |
| Burkholdaria cepacia genomvar dolsa | Virulent pathogen in lungs of patients with cystic fibrosis |
| Klebsiella pneumoniae | Causes pneumonia and wound infections, many MDR strains |
| Burkholdaria cepacia complex | Virulent pathogen in lungs of patients with cystic fibrosis |

TABLE 4

Exemplary wound strains

| Strain (wound) | Description |
| --- | --- |
| Staphylococcus aureus | Senisitive and MDR strains, can produce toxin, found on skin, in wounds, in tissue |
| Escherichia coli | Many resistant strains, found in wounds |
| Acinetobacter baumannii | Wound and tissue infections, slow growing, many MDR strains (including calcoaceticus complex) |
| Klebsiella pneumoniae | Nosocomical and independent wound infections, many MDR strains |
| Vancomycin resistant enterococcus | Higly resistant, thrives in wounds |
| Pseudomonas aeruginosa | Causes wound infections, colonizes medical devices, many MDR strains |

In some embodiments, bacteria associated with biofilm can include antibiotic resistant bacteria such as Methicillin resistant *Staphylococcus aureus*, Mupirocin resistant *Staphylococcus aureus*, Mupirocin and Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*. Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*. Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant coagulase negative Staphylococci, Fluoroquinolone resistant coagulase negative Staphylococci, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, Vancomycin resistant *Staphylococcus epidermidis*, multidrug resistant *Clostridium difficile*, multidrug resistant *Acinetibacter baumannii*, multidrug resistant *Kelbsiella pneumoniae*, or multidrug resistant *Escherichia coli*.

As used herein resistant microorganism or bacterium means, an organism which has become resistant to an antibacterial agent. Also, resistant microorganism or bacterium means its effective MIC has exceeded the effective dosage according to Clinical Laboratory Standards Institute (CLSI) resistance breaktpoints, predefined national or internationally accepted limits, at or above which administration of an effective dose of antibiotic produces undesirable side effects. In some embodiments, the minimum inhibitory concentration of an antibacterial agent for a resistant bacterium will be at least, 2, 5, 10, or 100 fold greater than that seen with a sensitive bacterium for a selected antibacterial agent.

In an embodiment, bacteria associated with biofilm can include, e.g., *Salmonella choleraesuis, Staphylococcus aureus, Klebsiella pneumoniae, Enterobacter aerogenes, Pseudomonas aeruginosa*, MRSA, *E. coli*, vancomycin resistant *Enterococcus faecalis, Acinetobacter baumannii*, MDR *Acinetobacter baumannii*, or MDR *Klebsiella pneumoniae*.

Biofilms can be associated with a variety of diseases or conditions, e.g., urinary tract infections, catheter infections, middle-ear infections, throat infection, formation of dental plaque, gingivitis, dental caries, halitosis, gastrointestinal tract infections, respiratory tract infections (e.g., airway infections, lung infections, pneumonia and chronic sinusitis), complications of contact lenses, eye infections, conjunctivitis, endocarditis, complications (e.g., infections) of cystic fibrosis, complications (e.g., infections) in immunocompromised patient, impairing cutaneous wound healing, chronic wounds, infections due to burns, reducing topical antibacterial efficacy in infected skin wounds, or infections of permanent indwelling devices such as joint prostheses, intrauterine devices or heart valves.

Exemplary bacteria associated with biofilm also include bacteria causing urinary tract infections, catheter infections, middle-ear infections, throat infection, formation of dental plaque, gingivitis, dental caries, halitosis, gastrointestinal tract infections, respiratory tract infections (e.g., airway infections, lung infections, pneumonia and chronic sinusitis), complications of contact lenses, endocarditis, complications (e.g., infections) of cystic fibrosis, complications (e.g., infections) in immunocompromised patient, impairing cutaneous wound healing, infections due to burns, reducing topical antibacterial efficacy in infected skin wounds, or infections of permanent indwelling devices such as joint prostheses, intrauterine devices or heart valves.

Exemplary diseases and conditions associated with biofilm can also include diseases characterized by the presence of one or more of the bacteria that cause resistant bacterial infections as described herein.

Bacterial Clumping

Bacterial population, e.g., in a body cavity or epithelial/mucosal surfaces in a subject, can be reduced (e.g., to a level closer to the normal microbial level) by clumping using compounds and compositions described herein. Described herein are also methods of treatment for the colonization of e.g., the ear, nose, throat, sinus, respiratory system, skin, wounds, or gastrointestinal tract by harmful bacteria. This clumping can, in some embodiments, act as a "barrier," for example, when a composition described herein is used to contact a bacterial population so as to result in clumping of the bacteria onto the soluble chitosan derivative, and the resulting composition is discarded by the subject (e.g., spit out, for example, as an oral rinse).

The method of clumping (e.g., barrier clumping) includes the step of contacting compositions or compounds described herein (e.g., soluble chitosans or derivatized chitosans) with bacteria, e.g., in a body cavity or epithelial/mucosal surfaces. The soluble chitosan or chitosan derivatives described herein can interact with more than one bacterium simultaneously, linking them via contact with a part of the polymer chain. Thus, the contact causes the bacteria to aggregate with one another. These bacterial clumps are limited in their ability to bind to other surfaces, thereby creating a barrier to colonization by the bacteria. This barrier is also a result of the decreased bacterial surface area available for colonization, the bacterial trapping within the aggregate as well as limitation of the exposure of bacterial surface receptors that are often used by bacteria to associate with biological or inert surfaces, thereby preventing the colonizing of pathogenic bacteria. In some preferred embodiments, the derivatized chitosan has a molecular weight of at least about 15 kDa.

The positively charged characteristic of chitosan derivatives, e.g., chitosan-arginine, can allow the composition described herein to be effective in clumping and aggregating bacteria. The positively charged polymer can interact with the negatively charged cell wall of the bacteria electrostatically. This, in turn, can allow the long polymer chains of chitosan derivatives, e.g., chitosan-arginine, to interact with the bacterial cell surface and bridge between bacteria cells. This interaction can allow for clumping and aggregation of the bacteria cells and prevents them from adhering to mucosal or tissue surfaces. This mechanical action can allow for easy removal of the bacteria from the surface of a body orifice, wound, gastrointestinal tract or pulmonary surface.

The neutral soluble chitosan derivatives, e.g. chitosan lactobionic acid, can allow the composition described herein to be effective in clumping and aggregating bacteria. The long polymer chains of chitosan derivatives, e.g., chitosan-arginine, interact with the bacterial cell surface and bridge between bacteria cells. This interaction can allow for clumping and aggregation of the bacteria cells and prevents them from adhering to mucosal or tissue surfaces. This mechanical action can allow for easy removal of the bacteria from the surface of a body orifice, wound, gastrointestinal tract or pulmonary surface.

Treatment

The compositions and compounds described herein (e.g., a soluble chitosan or a derivatized chitosan) can be administered to planktonic cells in culture or in biofilms, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a composition or compound (e.g., a compound described herein (e.g., a soluble derivatized chitosan) to a subject, e.g., a patient, or application or administration of the composition or compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, the term "prevent" or "prevention" is defined as the application or administration of a composition or compound (e.g., a compound described herein (e.g., a soluble derivatized chitosan)) to a subject, e.g., a subject who is at risk for a disorder (e.g., a disorder described herein), or has a disposition toward a disorder, or application or administration of the compound to an isolated tissue or cell, e.g., cell line, from a subject, e.g., a subject who is at risk for a disorder (e.g., a disorder as described herein), or has a predisposition toward a disorder, with the purpose to avoid or preclude the disorder, or affect the predisposition toward the disorder (e.g., to prevent at least one symptom of the disorder or to delay onset of at least one symptom of the disorder).

As used herein, an amount of a composition or compound effective to treat a disorder, or a "therapeutically effective amount" refers to an amount of the composition or compound which is effective, upon single or multiple dose administration to a subject, in treating a cell, or in curing, alleviating, relieving or improving a subject with a disorder beyond that expected in the absence of such treatment.

As used herein, an amount of a composition or compound effective to prevent a disorder, or "a prophylactically effective amount" of the composition or compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

As used herein, "administered in combination" or a combined administration of two agents means that two or more agents (e.g., compounds described herein) are administered to a subject at the same time or within an interval such that there is overlap of an effect of each agent on the patient. Preferably they are administered within 15, 10, 5, or 1 minute of one another. Preferably the administrations of the agents are spaced sufficiently close together such that a combinatorial (e.g., a synergistic) effect is achieved. Exemplary combinations of a derivatized chitosan described herein and one or more of anti-microbial agent(s) such as an antibiotic are described, e.g., in U.S. Patent Application 61/113,904, which is incorporated by reference herein by its entirety. The combinations can have synergistic effect when used to treat a subject having a bacterial infection. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject.

In a preferred embodiment, the agents are administered essentially simultaneously, for example two unit dosages administered at the same time, or a combined unit dosage of the two agents. In another preferred embodiment, the agents are delivered in separate unit dosages. The agents can be administered in any order, or as one or more preparations that includes two or more agents. In a preferred embodiment, at least one administration of one of the agents, e.g., the first agent, is made within minutes, one, two, three, or four hours, or even within one or two days of the other agent, e.g., the second agent. In some cases, combinations can achieve synergistic results, e.g., greater than additive results, e.g., at least 1.25, 1.5, 2, 4, 10, 20, 40, or 100 times greater than additive.

Subject

The subject can be a human or an animal. Suitable animal subjects include: but are not limited to, pet, wild, zoo, laboratory, and farm animals. Suitable animal subjects include primates, mammals, rodents, and birds. Examples of said animals include, but not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, fowl, e.g., pheasant, quail (or other gamebirds), a waterfowl, ostriches, chickens, turkeys, ducks, and geese or free flying bird.

In some embodiments, the subject has urinary tract infections, catheter infections, middle-ear infections, throat infections, eye infections, dental plaque, gingivitis, dental caries, halitosis, gastrointestinal tract infections, oral infections, respiratory tract infections (e.g., airway infections, lung infections, pneumonia, and chronic sinusitis), complications of contact lenses, endocarditis, complications (e.g., infections or increased pulmonary mucosal viscosity) of cystic fibrosis, gastrointestinal infections (e.g. gastroenteritis), complications (e.g., infections) in immunocompromised patient creating impaired cutaneous wound healing, infections due to burns, acute wounds, sub-acute wounds, post-surgical sites, chronic wounds or reduced topical antibacterial efficacy in infected skin wounds, or infections of permanent or temporary indwelling devices such as joint prostheses, ET tubes, catheters, intrauterine devices or heart valves.

In some embodiments, the subject has diseases or conditions characterized by the presence of one or more of the bacteria that cause resistant bacterial infection as described herein.

Cystic Fibrosis

The compositions described herein can be used to treat or prevent complications of cystic fibrosis in a subject. For example, liquid or solid particulate compositions comprising soluble chitosans or derivatized chitosans described herein can be used to treat or prevent complications of cystic fibrosis, e.g., lung infections or respiratory tract congestion, in a subject. Treatment or prevention includes administration of soluble chitosans or derivatized chitosans alone or in combination with drugs or treatments described below.

Cystic Fibrosis (also known as CF, mucovoidosis, or mucoviscidosis) is a hereditary disease affecting the exocrine (mucous) glands of the lungs, liver, pancreas, and intestines, causing progressive disability due to multisystem failure. CF is caused by a mutation in the gene cystic fibrosis transmembrane conductance regulator (CFTR). The product of this gene is a chloride ion channel important in creating sweat, digestive juices and mucus. CF is considered an autosomal recessive disease.

Symptomatic diseases and complications associated with CF include, e.g., lung and sinus diseases; gastrointestinal, liver and pancreatic diseases; endocrine diseases; and infertility. For example, lung disease results from clogging the airways due to mucosa buildup and resulting inflammation. Some of these symptoms occur when bacteria that normally inhabit the thick mucus grow out of control and cause pneumonia. In later stages of CF, changes in the architecture of the lung further exacerbate chronic difficulties in breathing. Other symptoms include coughing up blood (hemoptysis), changes in the major airways in the lungs (bronchiectasis), high blood pressure in the lung (pulmonary hypertension), heart failure, difficulties getting enough oxygen to the body (hypoxia), respiratory failure requiring support with breathing masks such as bilevel positive airway pressure machines or ventilators, allergic bronchopulmonary aspergillosis, and infection with *Mycobacterium avium* complex (MAC). Mucus in the paranasal sinuses is equally thick and may also cause blockage of the sinus passages, leading to infection. This may cause facial pain, fever, nasal drainage, and headaches. Individuals with CF may develop overgrowth of the nasal tissue (nasal polyps) due to inflammation from chronic sinus infections. These polyps can block the nasal passages and increase breathing difficulties.

Complications of CF, e.g., lung diseases, can be treated or prevented using soluble chitosans or derivatized chitosans described herein, in combination with one or more of agents or therapeutics. Exemplary agents to treat complications of CF, e.g., lung diseases include antibiotics such as xylitol, vancomycin, tobramycin, meropenem, ciprofloxacin, or piperacillin, administered e.g., intravenously. Inhaled therapy with antibiotics such as tobramycin, colistin or aztreonam can also be given to improve lung function by impeding the growth of colonized bacteria. Oral antibiotics such as ciprofloxacin or azithromycin can be given to help prevent infection or to control ongoing infection. Other methods to treat lung disease include, e.g., chest physiotherapy (CPT), Biphasic Cuirass Ventilation, or aerosolized medications (e.g., DNase (e.g., dornase (Pulmozyme®)), hypertonic saline, N-acetylcysteine, albuterol, or ipratropium). In some embodiments, the administrations of a combination of agents and therapeutics are spaced sufficiently close together such that a synergistic effect is achieved.

In one embodiment, a soluble chitosan or derivatized chitosan (e.g., a soluble chitosan or derivatized chitosan described herein) is used in combination with a DNase (e.g., Pulmozyme®) to treat a complication of cystic fibrosis, e.g., a lung disease. For example, the DNase (e.g., Pulmozyme®) can be administered at a dosage of less than about 2.5 mg twice a day, 2.0 mg twice a day, 1.5 mg twice a day, 1.0 mg twice a day, 0.5 mg twice a day, 2.5 mg once daily, 2.0 mg once daily, 1.5 mg once daily, 1.0 mg once daily, or 0.5 mg once daily.

Respiratory Tract Infections

The compositions described herein can be used to treat or prevent respiratory tract infections in a subject. For example, liquid or solid particulate compositions comprising soluble chitosans or derivatized chitosans described herein can be used to treat or prevent respiratory tract infections, e.g., respiratory tract bacterial infections, in a subject. Treatment or prevention includes administration of soluble chitosans or derivatized chitosans alone or incombination with drugs or treatments described below.

Respiratory tract infections can be caused by e.g., bacteria, viruses, parasites or fungi. Exemplary respiratory tract bacterial infections include upper respiratory tract infections such as sinusitis, pharygitis, epiglotittis, laryngitis, tracheitis, and rhinitis; and lower respiratory tract infections such as bronchitis and pneumonia.

Symptoms of respiratory tract infections include, e.g., pain, inflammation, fever, fatigue, lack of breath, nausea, diarrhea, cough, and death.

Respiratory tract infections can be treated or prevented using soluble chitosans or derivatized chitosans described herein, in combination with one or more of agents or therapeutics. Exemplary agents and therapeutics to treat respiratory tract infections includes systemic antibiotics, inhaled antibiotics, anti-inflammatory agents and steroids, mucolytic agents, and supplemental oxygen. In some embodiments, the administrations of a combination of agents and therapeutics are spaced sufficiently close together such that a synergistic effect is achieved.

Gastrointestinal Tract Infections

The compositions described herein can be used to treat or prevent gastrointestinal tract infections in a subject. For example, liquid or solid particulate compositions comprising soluble chitosans or derivatized chitosans described herein can be used to treat or prevent gastrointestinal tract infections, e.g., gastrointestinal tract bacterial infections, in a subject. Treatment or prevention includes administration of soluble chitosans or derivatized chitosans alone or incombination with drugs or treatments described below.

Gastrointestinal tract infections can be caused by e.g., bacteria (e.g., enteric bacteria), viruses, parasites or fungi. Exemplary gastrointestinal tract bacterial infections include noninflammatory gastroenteritis caused by e.g., *Staphylococcus aureus, Bacillus cereus, Clostridium perfringens, Clostridium difficile* or *Clostridium botulinum*; inflammatory gastroenteritis caused by e.g., *Vibrio cholerae*, Enterotoxigenic (ETEC) *Escherichia coli*, Enteropathogenic (EPEC) *Escherichia coli*, Enteroaggregative (EAggEC) *Escherichia coli, Clostridium dificile, Vibrio parahemolyticus*, or *Bacillus anthracis*; or invasive gastroenteritis caused by e.g., *Shigella* sp., *Salmonella* sp., *Campylobacter jejuni*, Enteroinvasive (EIEC) *Escherichia coli*, Enterohemorrhagic (EHEC) *Escherichia coli, Vibrion vulnificus, Yersinia* sp., *Francisella tularensis*, or *Helicobacter pylori*.

Symptoms of gastrointestinal tract infections include, e.g., diarrhea, vomiting, abdominal pain, cramps, fecal leukocytes, fever, dysentery, and/or blood in stool.

Gastrointestinal tract infections can be treated or prevented using soluble chitosans or derivatized chitosans described herein, in combination with one or more of agents or therapeutics. Exemplary agents and therapeutics to treat gastrointestinal tract infections includes rehydration, dietary therapy, probiotics, zinc, pharmacologic therapy (e.g., antibiotics (e.g., fluoroquinolone, metronidazole or vancomycin), antidiarrheal agents (e.g., loperamide or bismuth subsalicylate (BSS)), or antiemetic drugs (e.g., ondansetron or metoclopramide)). In some embodiments, the administrations of a combination of agents and therapeutics are spaced sufficiently close together such that a synergistic effect is achieved.

Antibacterials

The compositions and compounds described herein (e.g., soluble chitosans or derivatized chitosans) can be used in combination of one or more of antibiotics, to treat one or more diseases and conditions described herein. General classes of antibiotics include, e.g., aminoglycosides, bacitracin, beta-lactam antibiotics, cephalosporins, chloramphenicol, glycopeptides, macrolides, lincosamides, penicillins, quinolones, rifampin, glycopeptide, tetracyclines, trimethoprim and sulfonamides. In some embodiments, the administrations of a combination of agents and therapeutics are spaced sufficiently close together such that a synergistic effect is achieved.

Exemplary antibiotics within the classes recited above are provided as follows. Exemplary aminoglycosides include Streptomycin, Neomycin, Framycetin, Parpmycin, Ribostamycin, Kanamycin, Amikacin, Dibekacin, Tobramycin, Hygromycin B, Spectinomycin, Gentamicin, Netilmicin, Sisomicin, Isepamicin, Verdamicin, Amikin, Garamycin, Kantrex, Netromycin, Nebcin, and Humatin. Exemplary carbacephems include Loracarbef (Lorabid). Exemplary carbapenems include Ertapenem, Invanz, Doripenem, Finibax, Imipenem/Cilastatin, Primaxin, Meropenem, and Merrem. Exemplary cephalosporins include Cefadroxil, Durisef, Cefazolin, Ancef, Cefalotin, Cefalothin, Keflin, Cefalexin, Keflex, Cefaclor, Ceclor, Cefamandole, Mandole, Cefoxitin, Mefoxin, Cefprozill, Cefzil, Cefuroxime, Ceftin, Zinnat, Cefixime, Suprax, Cefdinir, Omnicef, Cefditoren, Spectracef, Cefoperazone, Cefobid, Cefotaxime, Claforan, Cefpodoxime, Fortaz, Ceftibuten, Cedax, Ceftizoxime, Ceftriaxone, Rocephin, Cefepime, Maxipime, and Ceftrobriprole. Exemplary glycopeptides include Dalbavancin, Oritavancin, Teicoplanin, Vancomycin, and Vancocin. Exemplary macrolides include Azithromycin, Sithromax, Surnamed, Zitrocin, Clarithromycin, Biaxin, Dirithromycin, Erythromycin, Erythocin, Erythroped, Roxithromycin, Troleandomycin, Telithromycin, Ketek, and Spectinomycin. Exemplary monobactams include Aztreonam. Exemplary penicillins include Amoxicillin, Novamox, Aoxil, Ampicillin, Alocillin, Carbenicillin, Coxacillin, Diloxacillin, Flucloxacillin Floxapen, Mezlocillin, Methicillin, Nafcillin, Oxacillin, Penicillin, and Ticarcillin. Exemplary polypeptides include Bacitracin, Colistin, and Polymyxin B. Exemplary quiniolones include Ciproflaxin, Cipro, Ciproxin, Ciprobay, Enoxacin, Gatifloxacin, Tequin, Levofloxacin, Levaquin, Lomefloxacin, Moxifloxacin, Avelox, Norfloxacin, Noroxin, Ofloxacin, Ocuflox, Trovafloxacin, and Trovan. Exemplary sulfonamides include Mefenide, Prontosil (archaic), Sulfacetamide, Sulfamethizole, Sulfanilamide (archaic), Sulfasalazine, Sulfisoxazole, Trimethoprim, Trimethoprim-Sulfamethoxazole (co-trimoxazole), and Bactrim. Exemplary tetracyclines include Demeclocyline, Doxycycline, Vibramycin, Minocycline, Minocin, Oxytetracycline, Terracin, Tetracycline, and Sumycin. Other exemplary antibiotics include Salvarsan, Chloamphenicol, Chloromycetin, Clindamycin, Cleocin, Linomycin, Ethambutol, Fosfomycin, Fusidic Acid, Fucidin, Furazolidone, Isoniazid, Linezolid, Zyvox, Metronidazole, Flagyl, Mupirocin, Bactroban, Nitrofurantion, Macrodantin, Macrobid, Platensimycin, Pyrazinamide, Quinupristin/Dalfopristin (Syncerid), Rifampin (Rifampicin), and Tinidazole. Exemplary antibiotics also include xylitol.

Anti-Inflammatory

The compositions and compounds described herein (e.g., soluble chitosans and derivatized chitosans) can be used in combination with one or more anti-inflammatory drugs, e.g., steroidal anti-inflammatory drugs and non-steroidal anti-inflammatory drugs (NSAIDs), to treat one or more diseases or conditions described herein. In some embodiments, the administrations of a combination of agents and therapeutics are spaced sufficiently close together such that a synergistic effect is achieved.

Exemplary steroidal anti-inflammatory drugs include glucocorticoids (corticosteroids), e.g., Hydrocortisone (Cortisol), Cortisone acetate, Prednisone, Prednisolone, Methylprednisolone, Dexamethasone, Betamethasone, Triamcinolone, Beclometasone, Fludrocortisone acetate, Deoxycorticosterone acetate (DOCA), and Aldosterone. Exemplary non-steroidal anti-inflammatory drugs include Aspirin, Choline and magnesium salicylates, Choline salicylate, Celecoxib, Diclofenac potassium, Diclofenac sodium, Diclofenac sodium with Isoprostol, Diflunisal, Etodolac, Fenoprofen calcium, Flurbiprofen, Ibuprofen, Indomethacin, Ketoprofen, Magnesium salicylate, Meclofenamate sodium, Mefenamic acid, Meloxicam, Nabumetone, Naproxen, Naproxen sodium, Oxaprozin, Piroxicam, Rofecoxib, Salsalate, Sodium salicylate, Sulindac, Tolmetin sodium, and Valdecoxib. Exemplary non-steroidal anti-inflammatory agents (e.g., peptides) include regulatory cytokines, such as interleukins, e.g., IL-1, IL-4, IL-6, IL-10, IL-11, and IL-13.

Mucolytic Agent (Expectorant)

The compositions and compounds described herein (e.g., soluble chitosans and derivatized chitosans) can be used in combination with one or more mucolytic agents, to treat one or more diseases and conditions described herein. A mucolytic agent or expectorant is an agent which dissolves thick mucus and is used to help relieve respiratory difficulties. It does so by hydrolyzing glycosaminoglycans, tending to break down/lower the viscosity of mucin-containing body secretions/components. The viscosity of mucous secretions in the lungs is dependent upon the concentrations of mucoprotein, the presence of disulfide bonds between these macromolecules and DNA.

An expectorant can reduce the thickness or viscosity of bronchial secretions and help bring up mucus and other material from the lungs, bronchi, and trachea. An example of as expectorant is guaifenesin which promotes drainage of mucus from the lungs by thinning the mucus and also lubricates the irritated respiratory tract. Other exemplary mucolytic agents or expectorants include Althea root, Antimony pentasulfide, Creosote, Guaiacolsulfonate, Guaifenesin, Ipecacuanha (Syrup of ipecac), Levoverbenone, Potassium iodide, Senega, Tyloxapol, Acetylcysteine, Ambroxol, Bromhexine, Carbocisteine, Domiodol, Dornase alfa, Eprazinone, Erdosteine, Letosteine, Mesna, Neltenexine, Sobrerol, Stepronin, and Tiopronin.

Soluble Chitosans and Chitosan Derivatives

The compositions described herein include a soluble chitosan or a functionalized chitosan derivative.

Chitosan is an insoluble polymer derived from chitin, which is a polymer of N-acetylglucosamine that is the main component of the exoskeletons of crustaceans (e.g. shrimp, crab, lobster). Chitosan is formed from chitin by deacetylation, and as such is not a single polymeric molecule, but a class of molecules having various molecular weights and various degrees of deacetylation. The percent deacetylation in commercial chitosans is typically between 50-100%. The chitosan derivatives described herein are generated by functionalizing the resulting free amino groups with positively charged or neutral moieties, as described herein. The degrees of deacetylation and functionalization impart a specific charge density to the functionalized chitosan derivative. The resulting charge density affects solubility, and the strength of interaction with bacterial cell walls and membranes. The molecular weight is also an important factor in the tenacity of bacterial wall interaction and thus bactericidal activity. Thus, in accordance with the present invention, the degree of deacetylation, the functionalization and the molecular weight must be optimized for optimal efficacy. The derivatized chitosans described herein have a number of properties which are advantageous including solubility at physiologic pH and antimicrobial activity when in solution or dry at any pH less than about 9.

A soluble chitosan as described herein, refers to a water soluble chitosan that is not derivatized on the hydroxyl or amine moieties. A soluble chitosan is comprised of glucosamine and acetylglucosamine monomers. Generally a water soluble chitosan has a molecular weight of less than or equal to about 10 kDa and a degree of deactylation equal or greater than 80%. Water soluble is defined as being fully dissolvable in water at pH 7.

The chitosan derivatives described herein are generated by functionalizing the resulting free amino groups with positively charged or neutral moieties, as described herein.

Chitosans with any degree of deacetylation (DDA) greater than 50% are used in the present invention, with functionalization between 2% and 50% of the available amines. The degree of deacetylation determines the relative content of free amino groups to total monomers in the chitosan polymer. Methods that can be used for determination of the degree of deacetylation of chitosan include, e.g. ninhydrin test, linear potentiometric titration, near-infrared spectroscopy, nuclear magnetic resonance spectroscopy, hydrogen bromide titrimetry, infrared spectroscopy, and first derivative UV-spectrophotometry. Preferably, the degree of deacetylation of a soluble chitosan or a derivatized chitosan described herein is determined by quantitative infrared spectroscopy. Percent functionalization is determined as the % of derivatized amines relative to the total number of available amino moieties prior to reaction on the chitosan polymer. Preferably, the percent functionalization of a derivatized chitosan described herein is determined by H-NMR or quantitative elemental analysis. The degrees of deacetylation and functionalization impart a specific charge density to the functionalized chitosan derivative. The resulting charge density affects solubility, and strength of interaction with bacterial cell walls and membranes. The molecular weight is important in controlling the size of the bacterial clumps. Thus, in accordance with the present invention, these properties must be optimized for optimal efficacy. Exemplary chitosan derivatives are described in Baker et al; Ser. No. 11/657,382 filed on Jan. 24, 2007, which is incorporated herein by reference.

The chitosan derivatives described herein have a range of polydispersity index (PDI) between about 1.0 to about 2.5. As used herein, the polydispersity index (PDI), is a measure of the distribution of molecular weights in a given polymer sample. The PDI calculated is the weight averaged molecular weight divided by the number averaged molecular weight. This calculation indicates the distribution of individual molecular weights in a batch of polymers. The PDI has a value always greater than 1, but as the polymer chains approach uniform chain length, the PDI approaches unity (1). The PDI of a polymer derived from a natural source depends on the natural source (e.g. chitin or chitosan from crab vs. shrimp vs. fungi) and can be affected by a variety of reaction, production, processing, handling, storage and purifying conditions.

Methods to determine the polydispersity include, e.g., gel permeation chromatography (also known as size exclusion chromatography); light scattering measurements; and direct calculation from MALDI or from electrospray mass spectrometry. Preferably, the PDI of a soluble chitosan or a derivatized chitosan described herein is determined by HPLC and multi angle light scattering methods.

The chitosan derivatives described herein have a variety of selected molecular weights that are soluble at neutral and physiological pH, and include for the purposes of this invention molecular weights ranging from 5-1,000 kDa. Embodiments described herein are feature medium range molecular weight of derivatized chitosans (25 kDa, e.g., from about 15 to about 300 kDa) which can have clumping, diffusible and biofilm disruption properties.

The functionalized chitosan derivatives described herein include the following:

(A) Chitosan-arginine compounds;

(B) Chitosan-natural amino acid derivative compounds;

(C) Chitosan-unnatural amino acid compounds;

(D) Chitosan-acid amine compounds;

(E) Chitosan-guanidine compounds; and (F) Neutral chitosan derivative compounds.

(A) Chitosan-Arginine Compounds

In some embodiments, the present invention is directed to chitosan-arginine compounds, where the arginine is bound through a peptide (amide) bond via its carbonyl to the primary amine on the glucosamines of chitosan:

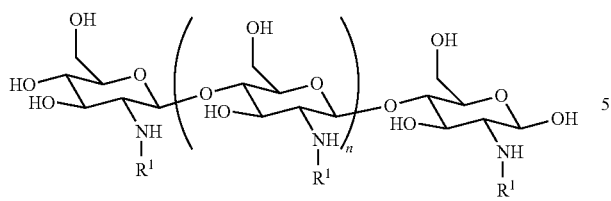

wherein each $R^1$ is independently selected from hydrogen, acetyl, and a group of the following formula:

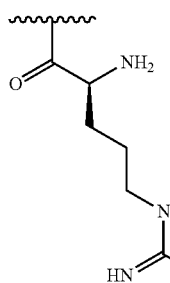 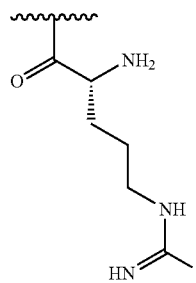

or a racemic mixture thereof,
wherein at least 25% of $R^1$ substituents are H, at least 1% are acetyl, and at least 2% are a group of the formula shown above.

(B) Chitosan-Natural Amino Acid Derivative Compounds

In some embodiments, the present invention is directed to chitosan-natural amino acid derivative compounds, wherein the natural amino acid may be histidine or lysine. The amino is bound through a peptide (amide) bond via its carbonyl to the primary amine on the glucosamines of chitosan:

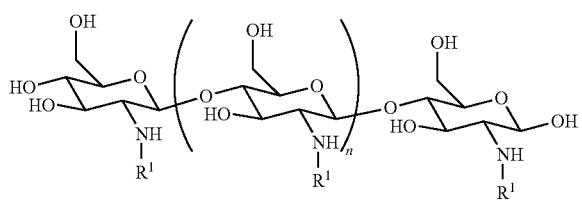

wherein each $R^1$ is independently selected from hydrogen, acetyl, and a group of the following formula:

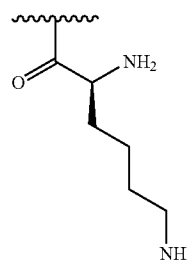 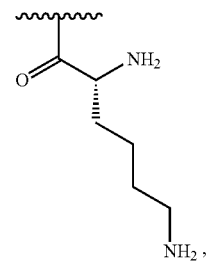

or a racemic mixture thereof, wherein at least 25% of $R^1$ substituents are H, at least 1% are acetyl, and at least 2% are a group of the formula shown above; OR a group of the following formula:

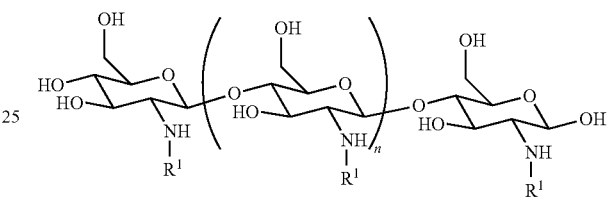

or a racemic mixture thereof, wherein at least 25% of $R^1$ substituents are H, at least 1% are acetyl, and at least 2% are a group of the formula shown above.

(C) Chitosan-Unnatural Amino Acid Compounds

In some embodiments, the present invention is directed to chitosan-unnatural amino acid compounds, where the unnatural amino acid is bound through a peptide (amide) bond via its carbonyl to the primary amine on the glucosamines of chitosan:

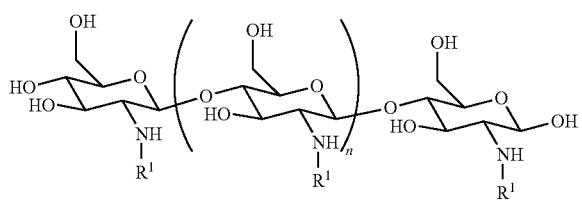

wherein each $R^1$ is independently selected from hydrogen, acetyl, and a group of the following formula:

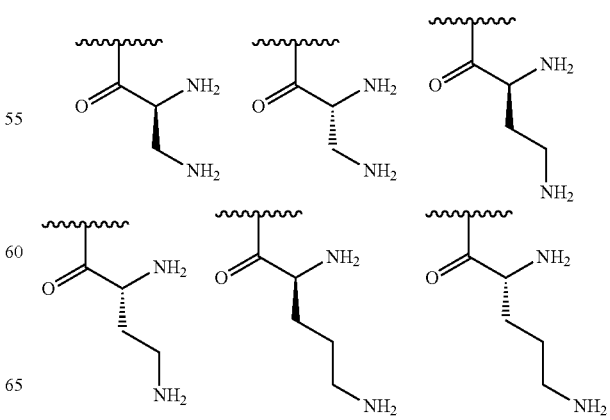

wherein $R^3$ is an unnatural amino acid side chain, and wherein at least 25% of $R^1$ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to chitosan have the following formulae:

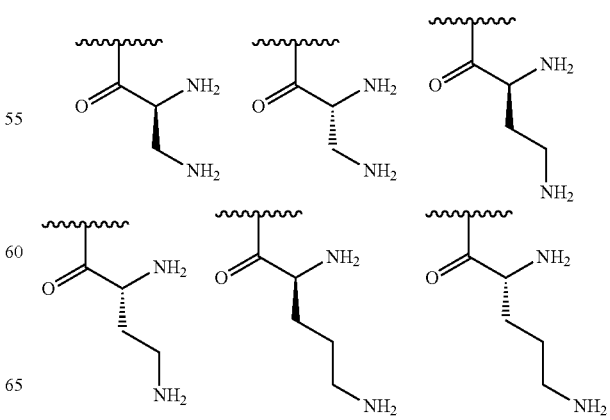

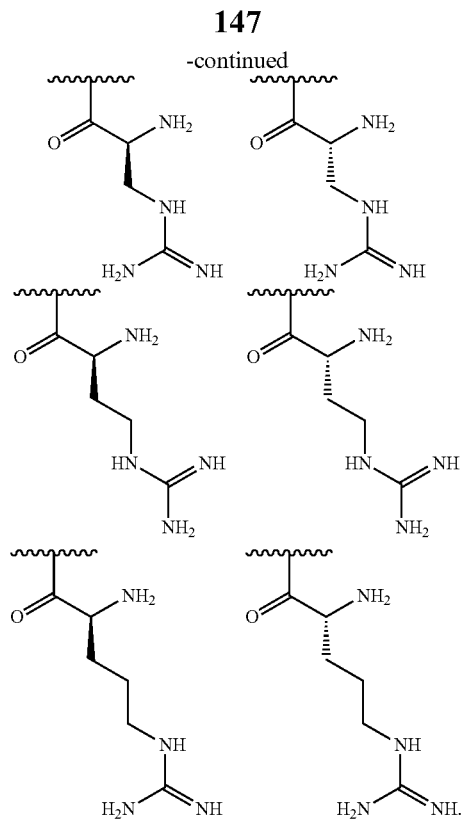

(D) Chitosan-Acid Amine and Guanidine Compounds

In some embodiments, the present invention is directed to chitosan-acid amine compounds, or their guanidylated counterparts. The acid amine is bound through a peptide (amide) bond via its carbonyl to the primary amine on the glucosamines of chitosan:

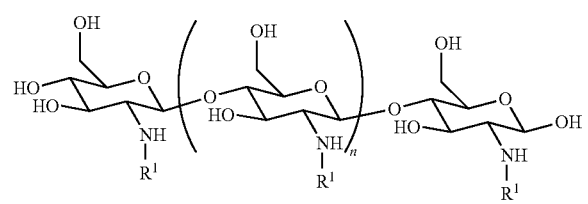

wherein each $R^1$ is independently selected from hydrogen, acetyl, and a group of the following formula:

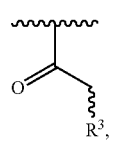

wherein $R^3$ is selected from amino, guanidino, and $C_1$-$C_6$ alkyl substituted with an amino or a guanidino group, wherein at least 25% of $R^1$ substituents are H, at least 1% are acetyl, and at least 2% are a group of the formula shown above.

In some embodiments, $R^1$ is selected from one of the following:

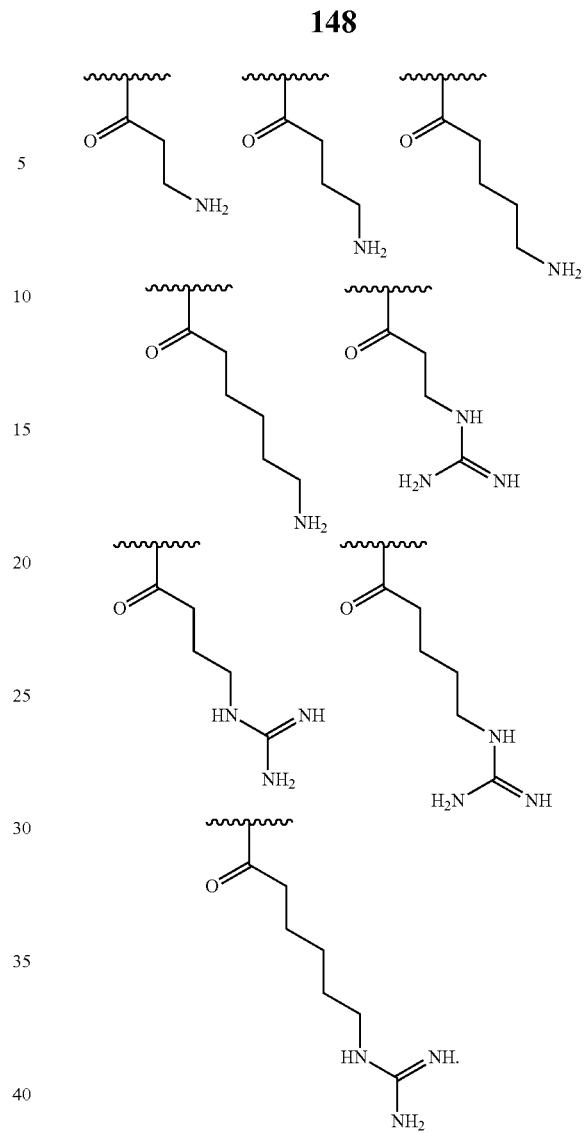

(F) Chitosan-Guanidine Compounds

In some embodiments, the present invention is directed to chitosan-guanidine compounds.

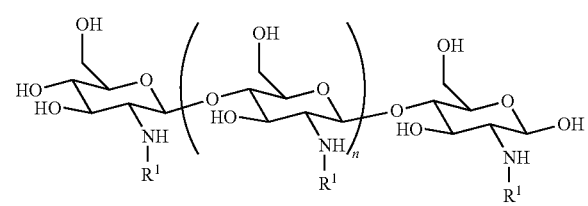

wherein each R is independently selected from hydrogen, acetyl, and or together with the nitrogen to which it is attached, forms a guanidine moiety; wherein at least 25% of R substituents are H, at least 1% are acetyl, and at least 2% are a group of the formula shown above.

(F) Neutral Chitosan Derivative Compounds

In some embodiments, the present invention is directed to neutral chitosan derivative compounds. Exemplary neutral chitosan derivative compounds include those where one or more amine nitrogens of the chitosan has been covalently attached to a neutral moiety such as a sugar:

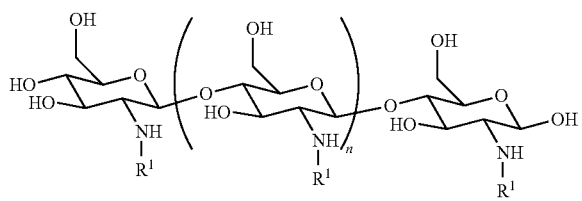

wherein each $R^1$ is independently selected from hydrogen, acetyl, and a sugar (e.g., a naturally occurring or modified sugar) or an α-hydroxy acid. Sugars can be monosaccharides, disaccharides or polysaccharides such as glucose, mannose, lactose, maltose, cellobiose, sucrose, amylose, glycogen, cellulose, gluconate, or pyruvate. Sugars can be covalently attached via a apacer or via the carboxylic acid, ketone or aldehyde group of the terminal sugar. Examples of α-hydroxy acids include glycolic acid, lactic acid, and citric acid. In some preferred embodiments, the neutral chitosan derivative is chitosan-lactobionic acid compound or chitosan-glycolic acid compound. Exemplary salts and coderivatives include those known in the art, for example, those described in US 20070281904, the contents of which is incorporated by reference in its entirety.

Compositions

Described herein are also compositions comprising a soluble chitosan or a functionalized chitosan derivative, e.g., a soluble or derivatized chitosan described herein. In some embodiments, the composition is a liquid, solid, or semisolid composition. In some embodiments, the composition is a pharmaceutical composition. In some embodiments, the composition is a reaction mixture.

In some embodiments, the composition further comprises one or more additional compound or agent. In some embodiments, the second compound or agent is another chitosan derivative, e.g., a soluble or derivatized chitosan described herein.

In some embodiments, the composition has less than about 20%, 15%, 10%, 5%, 2%, or 1%, or is substantially free, of a chitosan polymer wherein one or more of the nitrogen-containing groups of the glucosamine monomer is substituted with a polymerized amino acid, e.g., polyarginine (e.g., diargine, triargine, etc.).

In some embodiments, the composition has less than about 20%, 15%, 10%, 5%, 2%, or 1%, or is substantially free, of a chitosan polymer having a molecular weight of less than 15,000 Da, 10,000 Da, or 5,000 Da.

The composition described herein can be used to disrupt a preformed biofilm or prevent the formation of a biofilm in a subject. The composition described herein can also be used to treat or prevent a disease or a symptom of a disease described herein.

Formulations and Routes of Administration

The compounds described herein can be formulated in a variety of manners, including for oral or topical delivery (e.g., administered orally (e.g., oral rinse, throat gargle), by inhalation spray (e.g., nasal spray, nasal mists, or sinus spray), nebulizer, topically, rectally, nasally, buccally. In some embodiments, inhalation sprays (e.g., nasal spray, nasal mists, or sinus spray), are used for the nasal delivery of a compound descried herein, to locally treat or prevent an infection or disorder described herein, e.g., a nosocomial infection or MRSA infection. Inclusion in feed, water or an inhaled formulation is particularly desirable for use with animals. In some embodiments, a compound is formulated so as to allow the soluble chitosan or soluble chitosan derivative thereof to diffuse into a subject (e.g., into the wound, body cavities, or skin of a subject) upon administration to the subject or to be ingested, inhaled or swabbed while incorporated into a time release formulation.

The compound described herein (e.g., a soluble chitosan or a derivatized chitosan) can be administered before or after the onset of the disorder described herein. The methods herein contemplate administration of an effective amount of compound or compound composition to achieve the desired or stated effect. Typically, the compositions of this invention will be administered from about 1 to about 6 times per day. Alternatively, the compounds can be administered as a continuous time-release. Such administration can be used as a chronic or acute therapy. The amount of active ingredient that may be combined with the carrier materials to produce a single dosage form will vary depending upon the host treated and the particular mode of administration. A typical solution preparation will contain from about 1 µg/mL to 1000 µg/mL, about 5 µg/mL to 500 µg/mL, about 10 µg/mL to about 250 µg/mL, about 20 µg/mL to about 100 µg/mL, or about 40 µg/mL to about 60 µg/mL. A typical solid diffusible preparation will contain from about 1% to about 20%, about 2% to about 15%, or about 5% to about 10% by weight. A typical solid dissolvable preparation will contain from about 2% to about 95% by weight.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the type and nature of the bacteria, the patient's disposition to the disease, condition or symptoms, and the judgment of the treating physician.

In an embodiment, the compounds described herein (e.g., a soluble chitosan or a derivatized chitosan) can be formulated, e.g., as a solution, gel, or dressing, e.g., for treating a wound. In an embodiment, the dosage (e.g., solution dosage) is from about g/mL to about 1000 µg/mL, about 100 µg/mL to about 750 µg/mL, or about 250 g/mL to about 500 µg/mL, applied e.g., sufficiently to rinse a wound area. In an embodiment, the dosage (e.g., solution dosage) is about 10 to about 1000 g/mL, about 100 µg/mL to about 750 µg/mL, or about 250 µg/mL to about 500 µg/mL, applied to coat the wound at least 1, 2, 3, or 4 times daily. In an embodiment, the solid diffusible composition (dressing) is from about 1% to about 10%, about 3% to about 8%, or about 5% to about 6%, by weight applied to cover the wound at least 1, 2, 3, or 4 times daily. In an embodiment, the composition is applied to a thickness of at least about 1/128, 1/64, 1/32, or 1/16 inch.

In an embodiment, the compounds described herein (e.g., a soluble chitosan or a derivatized chitosan) can be formulated, e.g., as a solution, encapsulated time release, gel, or enema, e.g., for treating gastrointestinal disorder or condition. In an embodiment, the dosage is from about 10 µg/mL to about 5000 µg/mL, about 20 µg/mL to about 4000 µg/mL, about 100 µg/mL to about 3000 µg/mL, about 200 µg/mL to about 2000 µg/mL, or about 500 to about 1000 µg/mL in solution, e.g., ad libitum, e.g., in water or fluid. In an embodiment, the composition is administered at least 1, 2, 3, or 4 times daily. In an embodiment, the dosage is from about 1 mg/kg to about 100 mg/kg, about 2 mg/kg to about 75 mg/kg, about 5 mg/kg to about 50 mg/kg, or about 10 mg/kg to about 25 mg/kg body weight in an encapsulated time release, gel, capsule or enema. In an embodiment, the composition is administered at least 1, 2, 3, or 4 times daily.

In an embodiment, the compounds described herein (e.g., a soluble chitosan or a derivatized chitosan) can be formulated as a nebulized solution or powder, or lavage, e.g., for treating a pulmonary disorder or condition. In a preferred embodiment, the dosage is from about 500 µg to about 50000 µg, about 1000 µg to about 25000 µg, about 2000 µg to about 10000 µg, or about 4000 µg to about 6000 g, every 2, 4, 6, 8, 10, 12, or 24 hours. In an embodiment, the composition is administered at least 1, 2, 3, or 4 times daily.

In an embodiment, the compounds described herein (e.g., a soluble chitosan or a derivatized chitosan) can be formulated, e.g., as a spray, ointment, gel or inhalant, e.g., for treating a disorder or condition or ear, nose or throat. In a preferred embodiment, the dosage is from about 10 to 1000 µg/mL, about 100 µg/mL to about 750 µg/mL, or about 250 µg/mL to about 500 µg/mL in solution, or from about 0.1% to about 10%, about 0.5% to about 5%, or about 1% to about 2% by weight in an ointment or gel. In an embodiment, the composition is administered at least 1, 2, 3, or 4 times daily.

In an embodiment, the compounds described herein (e.g., a soluble chitosan or a derivatized chitosan) can be formulated as an ointment, solution, gel, or dressing, e.g., for skin decontamination or treating a skin condition. The dosage (e.g., solution dosage) is from about 10 µg/mL to about 1000 µg/mL, about 100 µg/mL to about 750 µg/mL, or about 250 µg/mL to about 500 µg/mL, applied e.g., sufficiently to rinse a skin area. In an embodiment, the dosage (e.g., solution dosage) is from about 10 to about 1000 µg/mL, about 100 µg/mL to about 750 µg/mL, or about 250 µg/mL to about 500 µg/mL applied to coat the skin at least 1, 2, 3, or 4 times daily. In an embodiment, the solid diffusible composition (dressing) is from about 1% to about 10%, about 3% to about 8%, or about 5% to about 6% by weight applied to coat the skin at least 1, 2, 3, or 4 times daily. In an embodiment, the composition is applied to a thickness of at least about 1/128, 1/64, 1/32, or 1/16 inch.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional compound including for example, a steroid or an analgesic; and any pharmaceutically acceptable carrier, adjuvant or vehicle. Alternate compositions of this invention comprise a compound described herein or a pharmaceutically acceptable salt thereof; and a pharmaceutically acceptable carrier, adjuvant or vehicle. The compositions delineated herein include the compounds described herein, as well as additional therapeutic compounds if present, in amounts effective for achieving a modulation of disease or disease symptoms.

The compositions are generally made by methods including the steps of combining a compound described herein with one or more carriers and, optionally, one or more additional therapeutic compounds delineated herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch.

Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The compounds of this invention may be administered by aerosol, nebulizer, or inhalation. In some embodiments, the composition is in the form of a dry powder, a suspension, or a solution. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Exemplary methods and devices for aerosol or inhalation include those described in U.S. Pat. No. 6,962,151, which is incorporated herein by reference in its entirety.

Compositions formulated for inhaled delivery generally include particles having a mean diameter of from about 0.1 am to about 50 am (e.g., from about 0.1 m to about 10 am, or from about 0.2 m to about 5 am. In some embodiments, the composition includes a dispersion of suitably-sized dry particles, for example, precipitants or crystals) or a dispersion of a solution (e.g., droplets) of a suitable size.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

In some cases, the pH of the formulation may be adjusted with pharmaceutically acceptable acids, bases or buffers to enhance the stability of the formulated compound or its delivery form for delivery in particular regions of the body, such as the colon.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of compounds described herein, both the compounds are generally present at dosage levels of between about 1 to 100%, and more preferably between about 5 to 95% of the dosage normally administered in a monotherapy regimen. Additionally, combinations of a plurality of compounds described herein are also envisioned. The compounds may be administered separately, as part of a multiple dose regimen, from the compounds of this invention. The compounds may be administered in a manner and dose where they act synergistically as describe e.g., in U.S. Patent Application 61/113,904, which is incorporated herein by reference in its entirety. Alternatively, those compounds may be part of a single dosage form, mixed together with the compounds of this invention in a single composition.

In some embodiments, the pharmaceutical compositions described herein can be administered topically, e.g., via liquid, semi-sold, gel, or time release, by irrigation, or by incorporation into a dressing.

Kits

A compound described herein (e.g., a soluble chitosan or a derivatized chitosan) can be provided in a kit. The kit includes (a) a composition that includes a compound described herein, and, optionally (b) informational material. The informational material can be descriptive, instructional, marketing or other material that relates to the methods described herein and/or the use of the compound described herein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to use of the compound described herein to treat a disorder described herein.

In one embodiment, the informational material can include instructions to administer the compound described herein in a suitable manner to perform the methods described herein, e.g., in a suitable dose, dosage form, or mode of administration (e.g., a dose, dosage form, or mode of administration described herein). In another embodiment, the informational material can include instructions to administer the compound described herein to a suitable subject, e.g., a human, e.g., a human having or at risk for a disorder described herein. For example, the material can include instructions to administer the compound described herein to such a subject.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using a compound described herein together with the other ingredients.

The compound described herein can be provided in any form, e.g., liquid, dried or lyophilized form. It is preferred that the compound described herein be substantially pure and/or sterile. When the compound described herein is provided in a liquid solution, the liquid solution preferably is an aqueous solution, with a sterile aqueous solution being preferred. When the compound described herein is provided as a dried form, reconstitution generally is by the addition of a suitable solvent. The solvent, e.g., sterile water or buffer, can optionally be provided in the kit.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is an implantable delivery device.

EXAMPLES

Figure 1A:
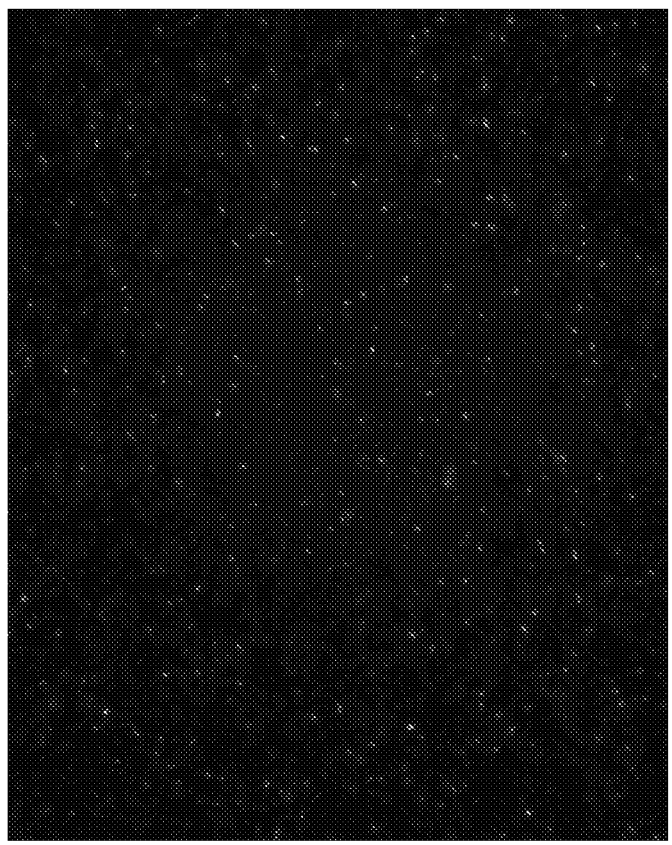
FIG. 1A shows Gram negative *Pseudomonas aeruginosa* strain PA01 in ultra-pure water at 200× magnification.

Example 1. Chitosan-Arginine Clumps Both Gram Positive and Gram Negative Bacteria Under Planktonic Conditions Planktonic conditions are defined for bacteria that are in solution, as opposed to conditions where bacteria are already attached to a surface. Clumping of the bacteria by chitosan-arginine occurs very rapidly in solution as shown in the SYTOX green/propidium iodide stained fluorescent images at 200× magnification. FIG. 1A shows a solution of Gram negative *Pseudomonas aeruginosa* strain PA01 (ATCC BAA-47) in ultra-pure water. Note that the bacteria in the images are very small as they are independent cells. FIG. 1B shows clumped *Pseudomonas aeruginosa* after 1 minute of exposure to 100 g/ml of chitosan-arginine (24 kDa, 28% functionalized, 83% DDA, 1.54 PDI). Note that this Gram negative bacteria clumps dramatically into very large agglomerates in a very short time.

Figure 2B:
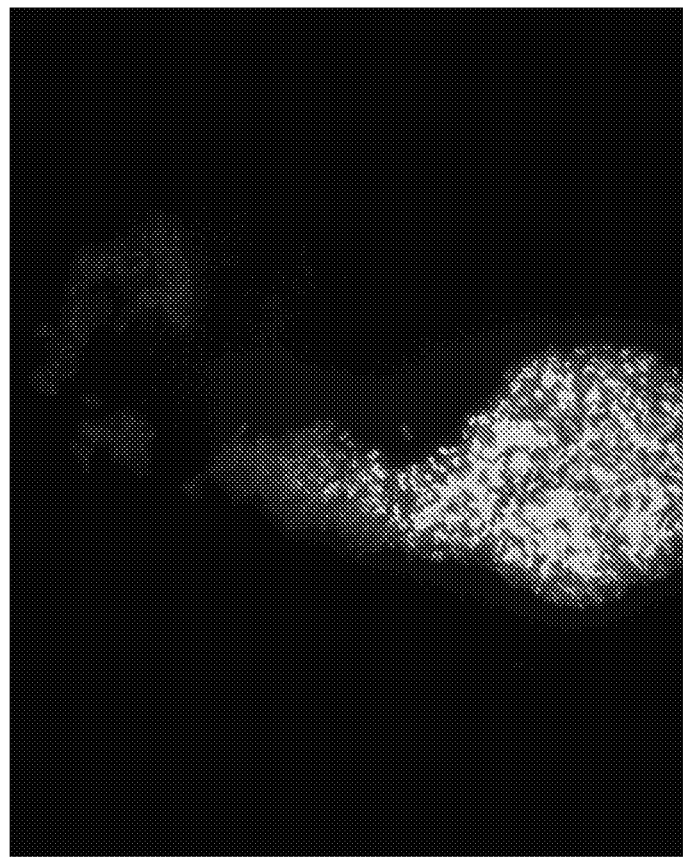
FIG. 2B shows the clumping of Gram positive *Streptococcus mutans* (ATCC 35668) after 1 minute of exposure to chitosan-arginine (24 kDa, 28% functionalized, 83% DDA, 1.54 PDI) at 200× magnification.
Figure 2A:
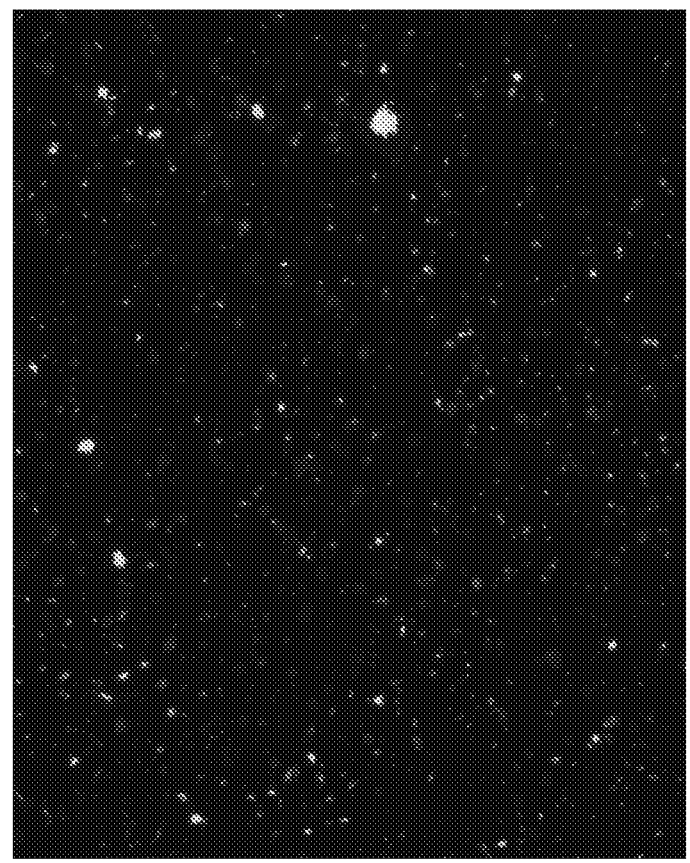
FIG. 2A shows Gram positive *Streptococcus mutans* (ATCC 35668) in ultra-pure water at 200× magnification.

Chitosan derivatives also clump Gram positive bacteria. FIG. 2A shows a solution of Gram positive *Streptococcus mutans* (strain) in ultra-pure water. Note that by their nature, Streptococci grow in chains or pairs. As seen in FIG. 2A, the bacteria exist as very small clumps. However, the dramatic clumping of *S. mutans* after 1 minute of exposure to 100 g/ml of chitosan-arginine (24 kDa, 28% functionalized, 83% DDA, 1.54 PDI) is seen in FIG. 2B. The chitosan-arginine provides a mechanism for very tight clumping of the bacteria.

Figure 3:
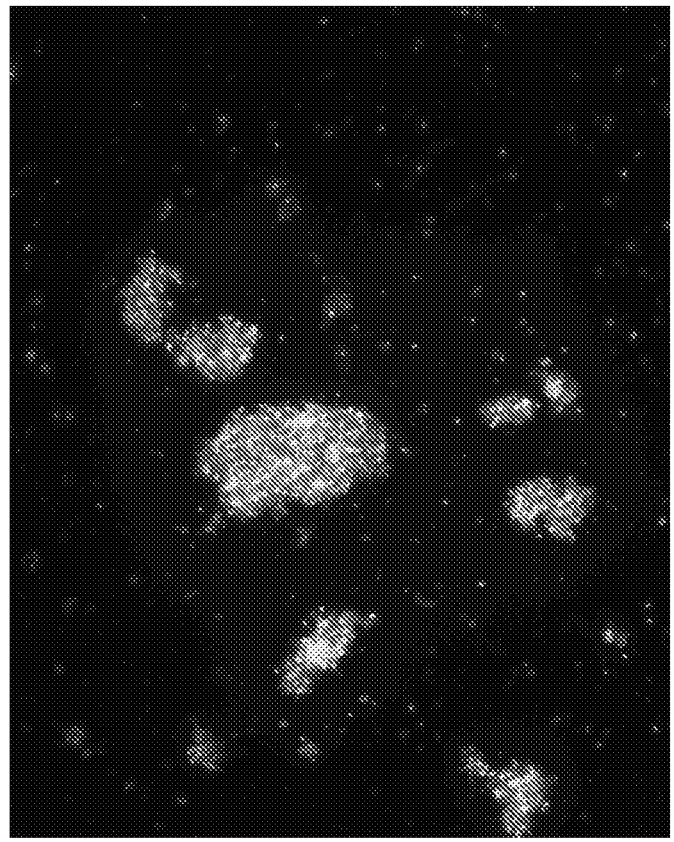
FIG. 3 shows the clumping of Gram negative *Pseudomonas aeruginosa* strain PA01 with chitosan-acid amine (29 kDa, 39% functionalization) in ultra-pure water at 200× magnification.
Figure 4B:
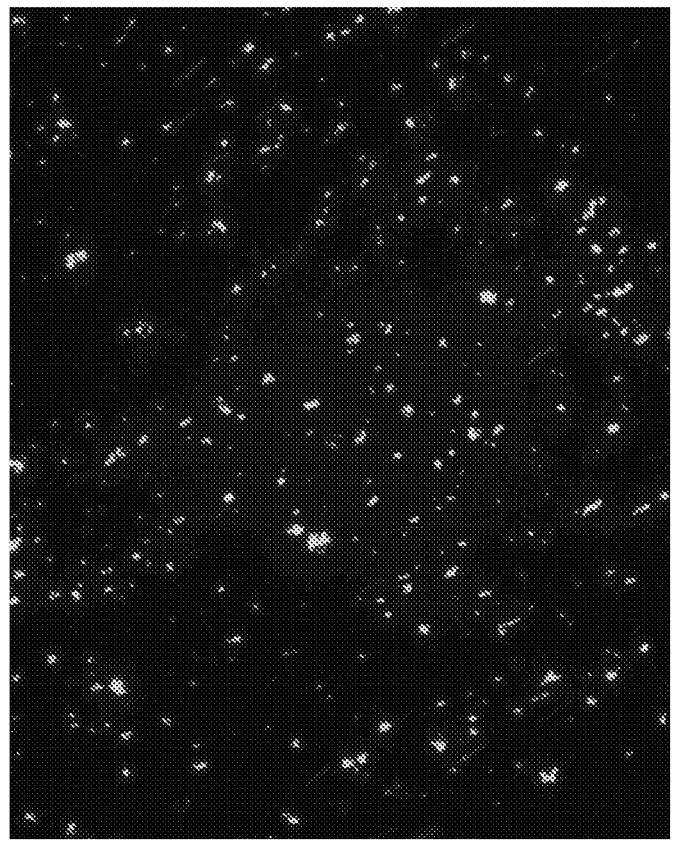
FIG. 4B shows Gram positive methicillin resistant *Staphylococcus aureus* strain MW-2 (clinical isolate from blood/CSF of community acquired disseminating infection) after 1 minute of exposure to chitosan-acid amine (29 kDa, 38% functionalized) at 200× magnification.
Figure 4A:
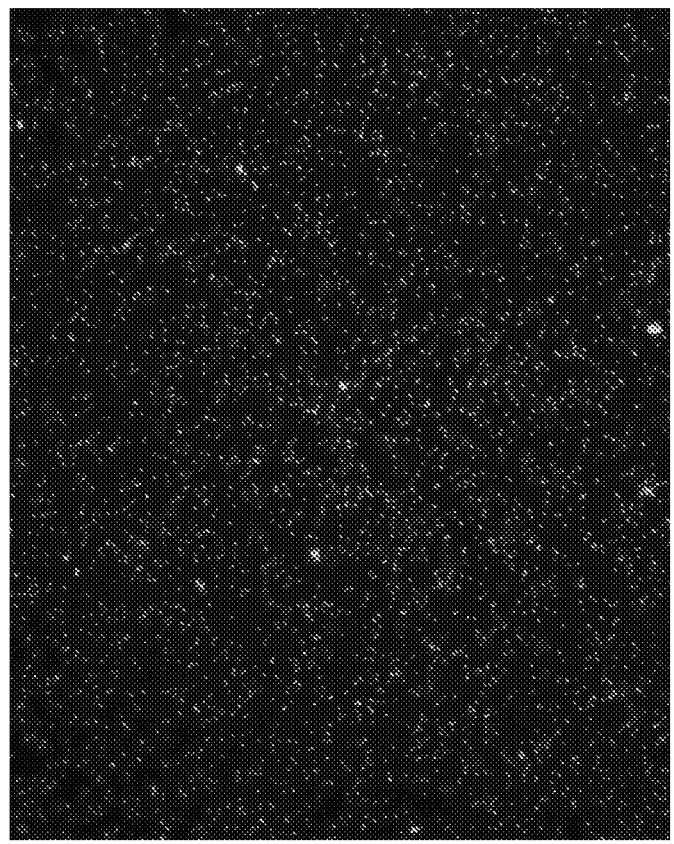
FIG. 4A shows Gram positive methicillin resistant *Staphylococcus aureus* strain MW-2 (clinical isolate from blood/CSF of community acquired disseminating infection) in ultra-pure water at 200× magnification.

Example 2. Chitosan-Acid Amines Clump Both Gram Positive and Gram Negative Bacteria Under Planktonic Conditions Chitosan derivatives known as chitosan-acid amines, derived from 6-amino-hexanoic acid were observed to clump both Gram positive and Gram negative bacteria under planktonic conditions. Clumping occurs very rapidly, in solution, as shown in the SYTOX green/propidium iodide stained fluorescent images at 200× magnification. FIG. 3 shows the clumping of the *Pseudomonas aeruginosa* strain PAO1 (ATCC BAA-47) after 1 minute of exposure to 100 μg/ml of chitosan-acid amine (29 kDa, 39% functionalized with 6-amino-hexanoic acid) compare to the untreated control (See FIG. 1A). FIG. 4A shows Gram positive methicillin resistant *Staphylococcus aureus* strain MW-2 in ultra-pure water. Note that *Staphylococcus* can make very small clusters by their natural growth cycle. FIG. 4B shows the same *Staphylococcus aureus* strain MW-2 being clumped after 1 minute of exposure to 100 μg/ml of chitosan-acid amine (29 kDa, 39% functionalized with 6-amino-hexanoic acid). Note that the morphology of the clumping is different than with *Pseudomonas aeruginosa*, but that clumping nonetheless occurs. The morphology of the clumping is dependent on the strain of the bacteria, the molecular weight and chain length of the derivative and the nature of the chitosan derivative moiety.

Figure 5:
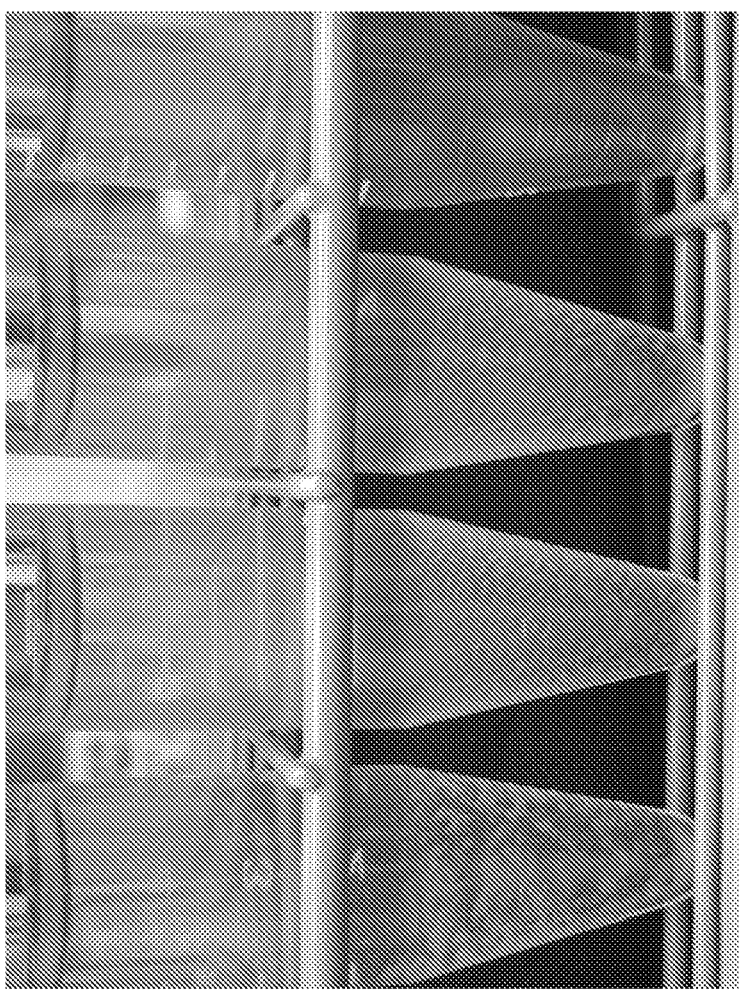
FIG. 5 shows Gram negative *Pseudomonas aeruginosa* strain PA01, after 24 hours exposure to (A) 100 µg/ml chitosan-lactobionic acid (125 kDa), (B) 100 µg/ml chitosan-arginine (28 kDa, 37% functionalization, 89% DDA, 1.95 PDI), (C) 100 µg/ml chitosan-arginine (40 kDa, 37% functionalization, 89% DDA, 2.454 PDI), and (D) water.
Figure 6:
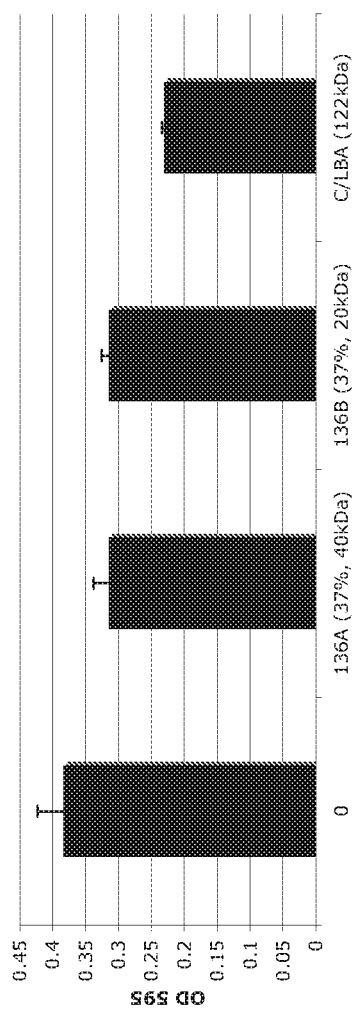
FIG. 6 shows quantification of the reduction of Gram negative *Pseudomonas aeruginosa* strain PA01 in solution after 24 hours exposure to 100 µg/ml chitosan-arginine (40 kDa, 37% functionalization, 89% DDA, 2.454 PDI), 100 g/ml chitosan-arginine (28 kDa, 37% functionalization, 89% DDA, 1.95 PDI), and 100 µg/ml chitosan-lactobionic acid (125 kDa) shown visually in FIG. 5.

Example 3. Higher Molecular Weight Chitosan Derivatives Aggregate Bacteria into Larger Clumps than Lower Molecular Weight Chitosan Derivatives While chitosan derivatives can clump a broad spectrum of bacteria, the molecular weight of the derivative is an important parameter because different molecular weights provide different clumping morphologies, regardless of the nature of the chitosan derivative. As shown in FIGS. 5 and 6, higher molecular weight chitosan derivatives aggregate bacteria into larger clumps than lower molecular weight chitosan derivatives. Specifically in FIG. 5, Gram negative *Pseudomonas aeruginosa* strain PA01 shows visible evidence of clumping after 24 hours treatment with 100 μg/ml chitosan-lactobionic acid the neutral chitosan derivative (125 kDa) (Tube A), 100 μg/ml chitosan-arginine (28 kDa, 37% functionalization, 83% DDA, 1.95 PDI) (Tube B), 100 g/ml chitosan-arginine (40 kDa, 37% functionalization, 83% DDA, 2.454 PDI) (Tube C), and compared to water alone (Tube D). The difference between the 28 kDa chitosan derivative (Tube B) and the 125 kDa chitosan derivative (Tube A) shows that greater clumping occurs following treatment with the larger molecule. This data is quantified in FIG. 6. The derivatives as described above, were added to the Gram negative *Pseudomonas aeruginosa* strain PA01 suspension (total volume 5 mL). Following 24 hours treatment, three samples of each treatment in a volume of 100 μl was obtained from the middle (to avoid misrepresentation of the observation because of natural bacterial settling due to gravity) of each bacterial suspension. The OD 595 was measured. A decrease in the OD 595 with respect to the PA01 in water alone indicated the bacteria were aggregating and precipitating out of the suspension, corresponding to visible observations in FIG. 5.

Example 4. Reduction of the Carrier State of *Staphylococcus aureus* and/or *Acinetobacter baumannii* in the Nose (Anterior Nares)

Figure 7A:
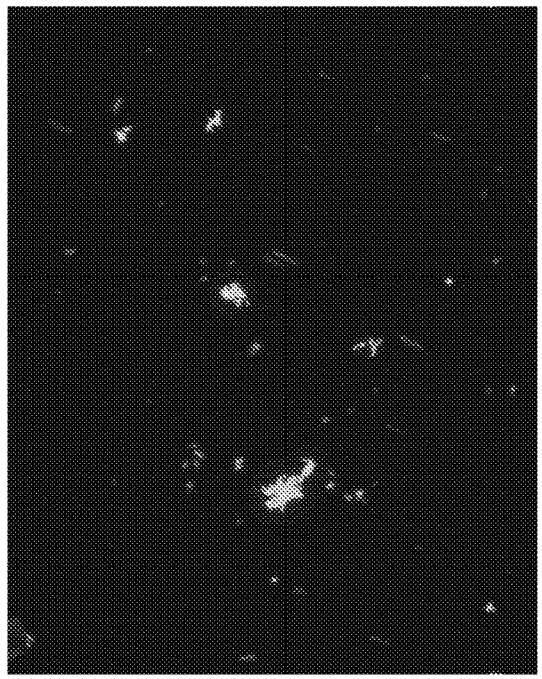
FIG. 7A shows clumping of *Streptococcus mutans* (ATCC 35668) by 2 µg/ml of chitosan-arginine (32 kDa, 29% functionalization, 83% DDA, 1.5 PDI) after five minutes incubation at 200× magnification.
Figure 7B:
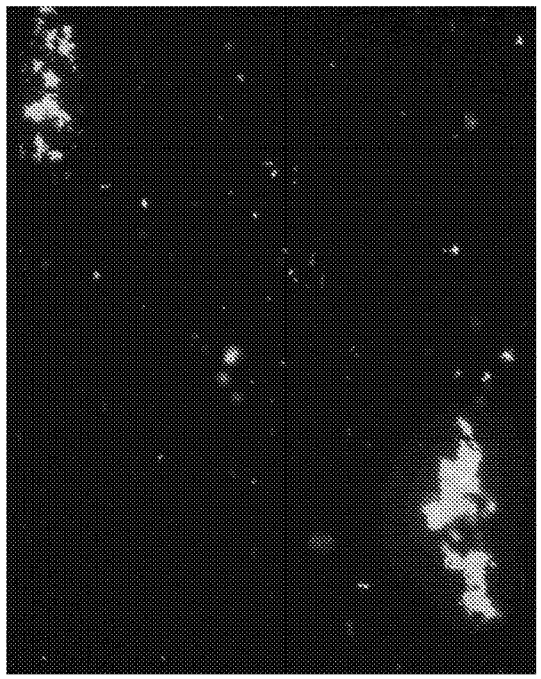
FIG. 7B shows clumping of *Streptococcus mutans* (ATCC 35668) by 10 µg/ml of chitosan-arginine (32 kDa, 29% functionalization, 83% DDA, 1.5 PDI) after five minutes incubation at 200× magnification.
Figure 7C:
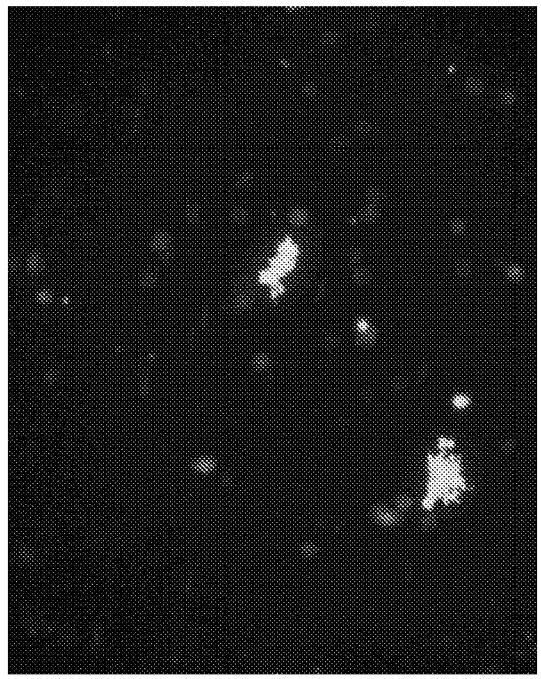
FIG. 7C shows clumping of *Streptococcus mutans* (ATCC 35668) by 20 µg/ml of chitosan-arginine (32 kDa, 29% functionalization, 83% DDA, 1.5 PDI) after five minutes incubation at 200× magnification.
Figure 8B:
FIG. 8B shows the ability of chitosan-arginine (24 kDa, 28% functionalized, 83% DDA, 1.5 PDI) to clump methicillin resistant *Staphylococcus aureus* strain MW-2 (clinical isolate from blood/CSF of community acquired disseminating infection) after 1-minute exposure (400× magnification).
Figure 8A:
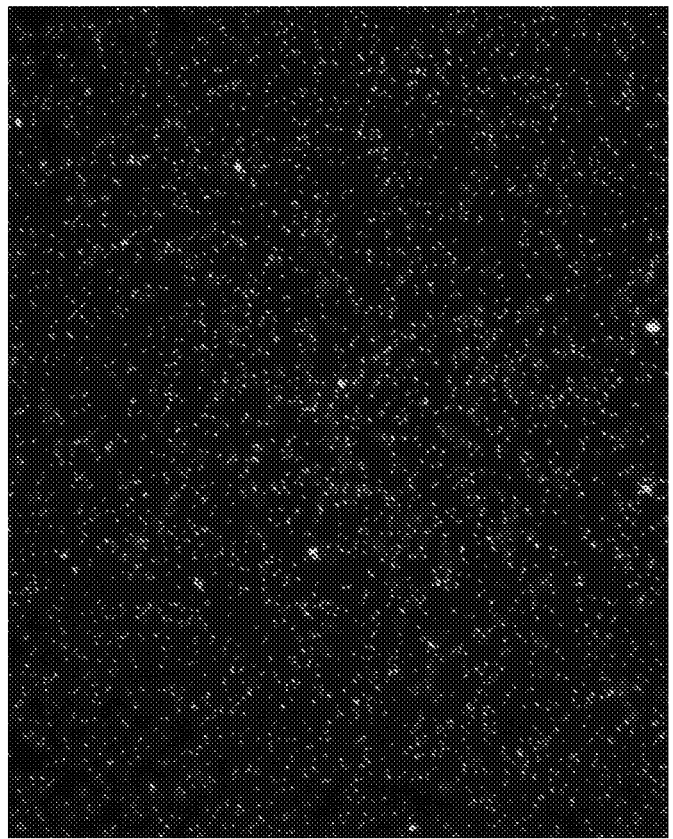
FIG. 8A shows methicillin resistant *Staphylococcus aureus* strain MW-2 (clinical isolate from blood/CSF of community acquired disseminating infection) in ultra pure water (400× magnification).

It has been shown that the reduction of the carrier state of bacteria in the anterior nares is sufficient to reduce nosocomial infections. A chitosan derivative nasal spray in hypotonic, neutral solution is sufficient to clump over $10^8$ bacteria/ml. Chitosan derivatives clump *Acinetobacter baumannii* and multiple strains of MRSA as shown above. FIGS. 7A-7C shows that *Streptococcus mutans* is clumped by various doses of chitosan-arginine after five minutes incubation at 200× magnification. FIGS. 7A through 7C show clumping of *Streptococcus mutans* by 2 μg/ml, 10 μg/ml, and 20 μg/ml of chitosan-arginine, respectively, at 200× magnification. It is important to note that the lowest of these doses is sufficient to cause significant aggregation of the bacteria. Furthermore, clumping is also observed in known resistant bacteria such as MRSA as shown in FIGS. 8A and 8B. FIG. 8A shows *Staphylococcus aureus* strain MW-2, a blood/CSF isolate that is methicillin resistant after a 1-minute exposure to water. It is important to note that Staphylococci tend to exist naturally in very small clusters. However, after the addition of chitosan-arginine as shown in FIG. 8B, clumping dramatically increases.

TABLE 5

Exemplary bacteria clumped by positive and neutral chitosan derivatives

| Gram positive | Gram negative |
|---|---|
| *Staphylococcus aureus* MW-2 | *Escherichia coli* O:157 H:7 |
| *Streptococcus mutans* | *Shigella flexneri* |
| *Clostridium perfringens* | *Salmonella typhimurium* |
| *Streptococcus pyogenes* (GAS) | *Acinetobacter baumannii* |
| | *Pseudomonas aeruginosa* |

Example 5. Mammalian Cells are not Clumped by these Chitosan Derivatives

Figure 9A:
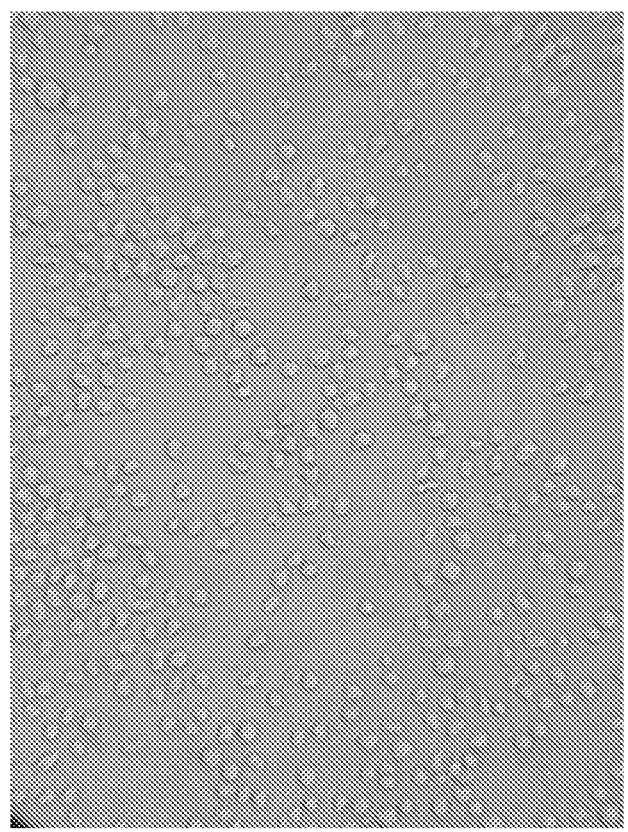
FIG. 9A shows optical microscope images taken at 20× of THP-1 human monocyte cell line exposed to 100 g/ml of 40 kDa chitosan-arginine 37% functionalized for 24 hours at high cell density.
Figure 9B:
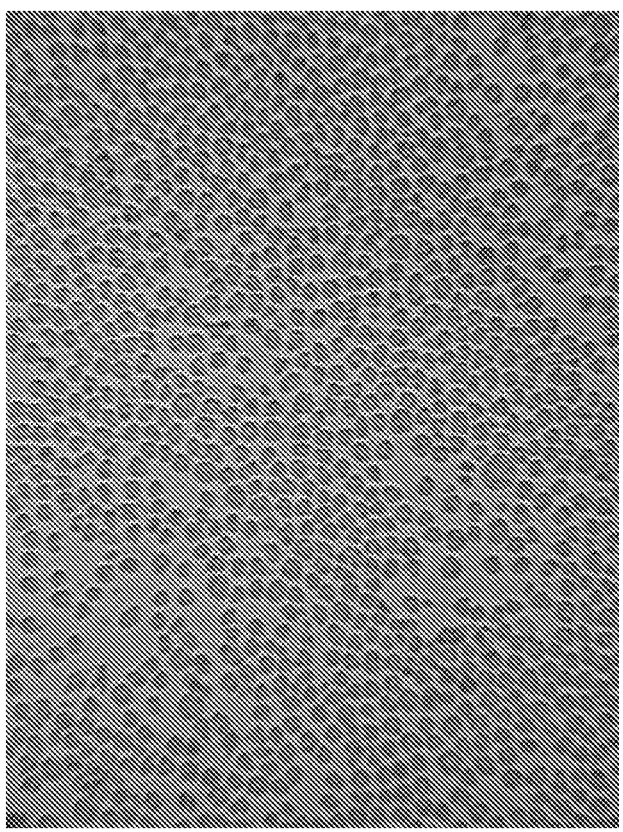
FIG. 9B shows optical microscope images taken at 20× of THP-1 human monocyte cell line exposed to 100 g/ml of 40 kDa chitosan-arginine 37% functionalized for 24 hours at lower cell density.

A number of human cells have been treated with up to 1 mg/ml of chitosan-arginine with no change in viability nor any indication of clumping. FIGS. 9A and 9B shows optical microscope images taken at 20× of THP-1 human monocyte cell line exposed to 100 μg/ml of 40 kDa chitosan-arginine 37% functionalized for 24 hours at high (A) and lower (B) cell density ($10^6$ cells/ml and $10^5$ cells/ml, respectively). The viability and structure of mammalian cells is not affected by the presence of the chitosan derivatives up to doses that are highly effective at clumping bacteria. These positively charged, soluble polymer chitosan derivatives are very broadly effective at clumping bacteria, with somewhat higher efficiency of clumping Gram positive relative to Gram-negative bacteria. As will be understood by one of ordinary skill, selection of an appropriate MW and functionalization depends on the strain and species of the bacteria.

Example 6. The Ability of Chitosan Derivatives to Clump and Reduce Viable *Clostridium difficile*

The ability of chitosan derivatives to treat enteric infection by reducing the effective bacterial load via clumping and reducing viable *Clostridium difficile* is tested. *Clostridium difficile* is closely related to *Clostridium perfringens*, having similar etiology in the gut. *Clostridium difficile* is mostly found in humans, and *Clostridium perfringens* is mostly found in poultry. Efficacious doses of chitosan derivatives are determined in vitro for significant reduction of *Clostridium difficile* viability alone and in synergistic combinations with current antibiotic therapies. Additional information about the potential role for chitosan-lactobionic acid can complement these studies and provide a neutral control aiding in elucidating the role of the positive charge versus the chitosan backbone itself in bacterial interaction. A treatment formulation to be tested in animal models can be developed. Oral therapies of chitosan-arginine can be tested in well-established in vivo models of *Clostridium difficile* infections to ascertain the feasibility and effectiveness of this antimicrobial polysaccharide. Potential applications, although focused here on *Clostridium difficile* infections, extend broadly to enteric infections.

Example 7. Viscosity Studies

1% Sodium Alginate Biofilm Model Treated with Chitosan-Arginine

Homogeneous 1% sodium alginate solutions (35 mL each) were prepared in water. Viscosity was immediately (0.1 hours) measured on a Brookfield digital viscometer (Model DV-E) using spindle 62 at speed 30 rpm, after adding either 100 µg/mL chitosan-arginine (in 2 mL, 25% functionalized, 18 kDa, 88% DDA, PDI 1.47) or an equivalent amount of water (control). Viscosity was also measured 1 and 4 hours following treatment.

Figure 10:
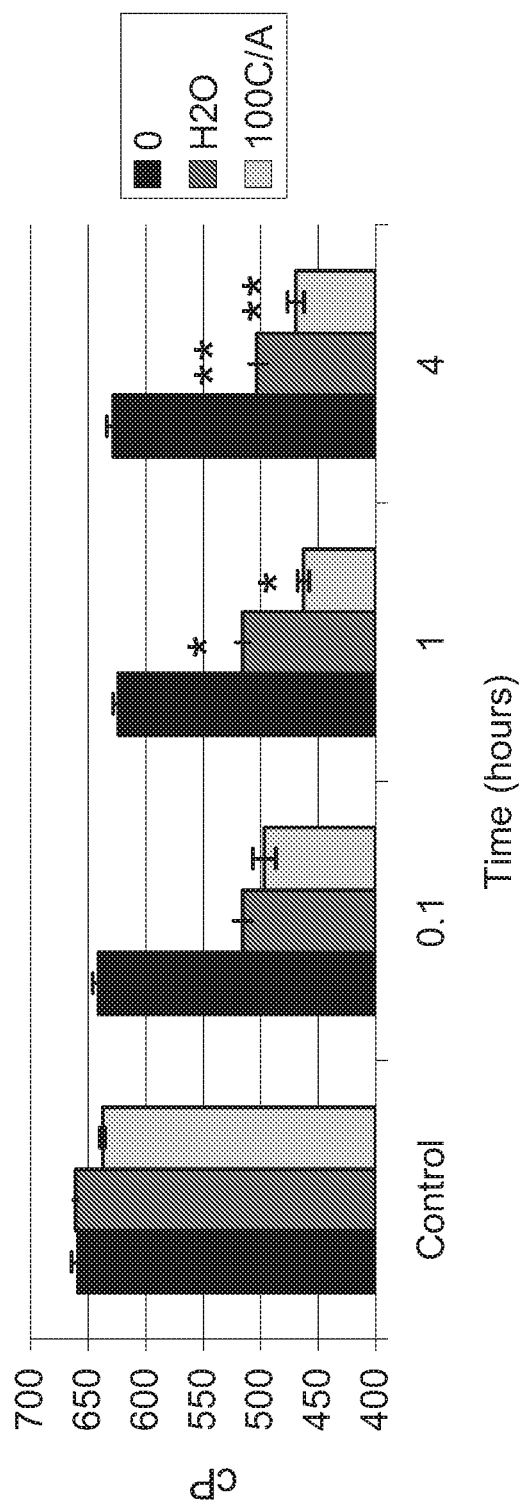
FIG. 10 shows reduction in the viscosity of 1% sodium alginate biofilm model treated with 100 g/ml chitosan-arginine (18 kDa, 25% functionalization, 88% DDA, 1.47 PDI) compared to an equal volume of water 6 minutes, 1 hour, and 4 hours after addition. * or ** indicates significant difference p=0.01.

As shown in FIG. 10, after 1 and 4 hours, chitosan-arginine showed a significant (p=0.01) reduction in the viscosity of the sodium alginate solution compared to water treatment alone.

*Pseudomonas aeruginosa* Biofilm/Spent Media Viscosity Study

Figure 11:
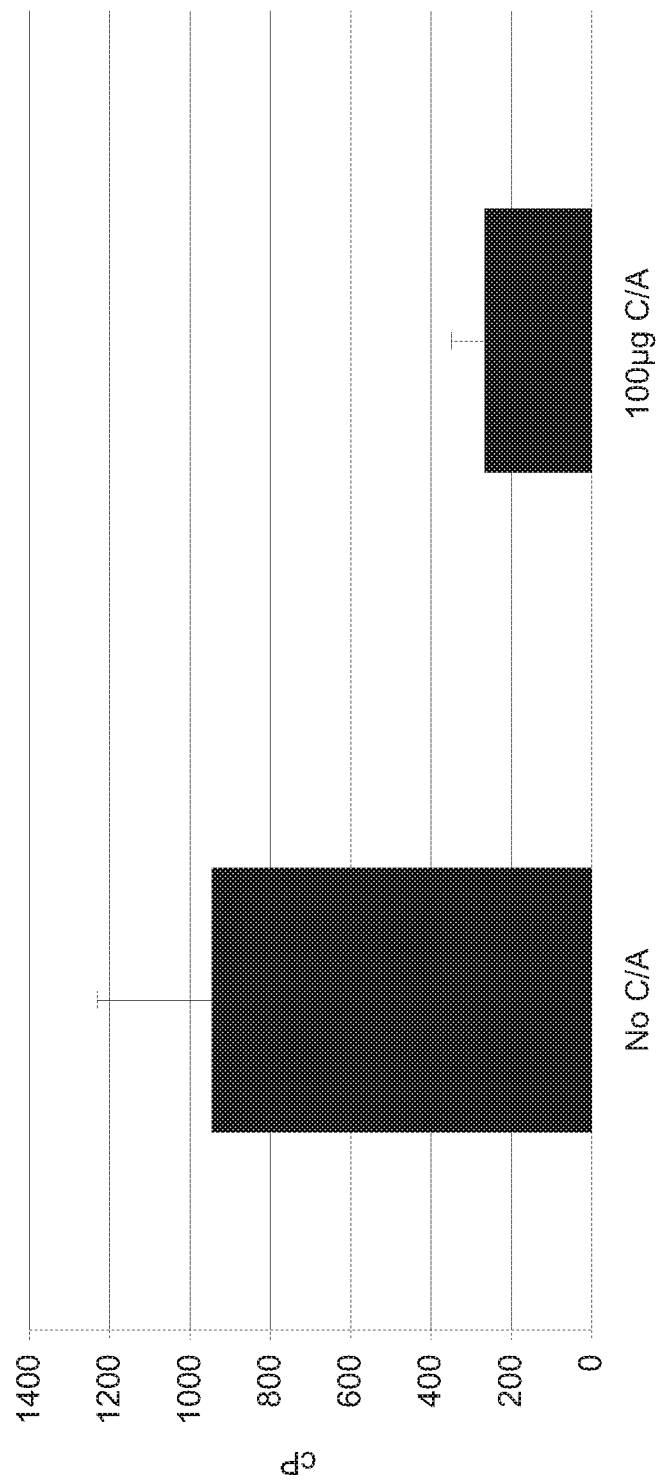
FIG. 11 shows reduction in the viscosity of *Pseudomonas aeruginosa* strain PA01 biofilm/spent media after 1-minute treatment with 100 µg/ml chitosan-arginine (18 kDa, 25% functionalization, 88% DDA, 1.47 PDI).

*Pseudomonas aeruginosa* biofilms were grown in polystyrene plates for 2.5 days at 37° C. The biofilm supernatant/spent media is very viscous due to alginate production and DNA sequestration. We tested the ability of chitosan-arginine to reduce the viscosity of *P. aeruginosa* biofilm supernatants/spent media following a 1-minute treatment with 100 µg/mL chitosan-arginine. First, a dramatic visual reduction in viscosity was observed upon addition of the chitosan-arginine to the gelatinous material. Subsequently, a Brookfield spinning viscometer was used to measure the viscosity of biofilm supernatants that were removed from the polystyrene plates and placed in 1.5 ml tubes. Four samples each were tested before chitosan-arginine treatment and 1-minute after 100 µg/mL chitosan-arginine (28% functionalized, 24 kDa, 83% DDA, PDI 1.54) treatment. Viscosity readings in centipoises (cP) were obtained with spindle number 64 at a speed of 50 rpm. As shown in FIG. 11, the average viscosity before chitosan-arginine treatment was 950±280 cP. Following the 1-minute chitosan-arginine treatment, this measurement was reduced to 270±80 cP and the material appeared visually less opaque than untreated biofilm supernatant.

CF Patient Sputum Study: Pourability

Two sputum samples were obtained from cystic fibrosis patients during routine clinical practice and collected immediately from the hospital. The each sample was briefly vortexed and a volume of 200 µL was placed in two microfuge tubes. The controls were treated with 10 µL of water only. The others were treated with 100 µg/mL of chitosan-arginine (25% functionalized, 43 kDa, 88% DDA, PDI 2.28) in 10 µL of water. After a brief mixing step the tubes were incubated at 37° C. for 1 hour to simulate conditions in the patient. The tubes were removed and tested for pourability.

Figure 12:
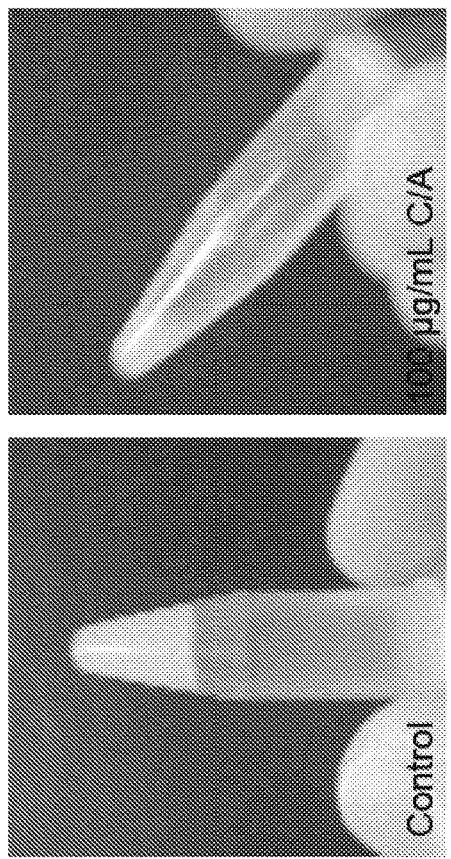
FIG. 12 shows the pourability of cystic fibrosis patient sputum samples treated with 100 µg/ml chitosan-arginine (43 kDa, 25% functionalization, 88% DDA, 2.28 PDI).
Figure 12:
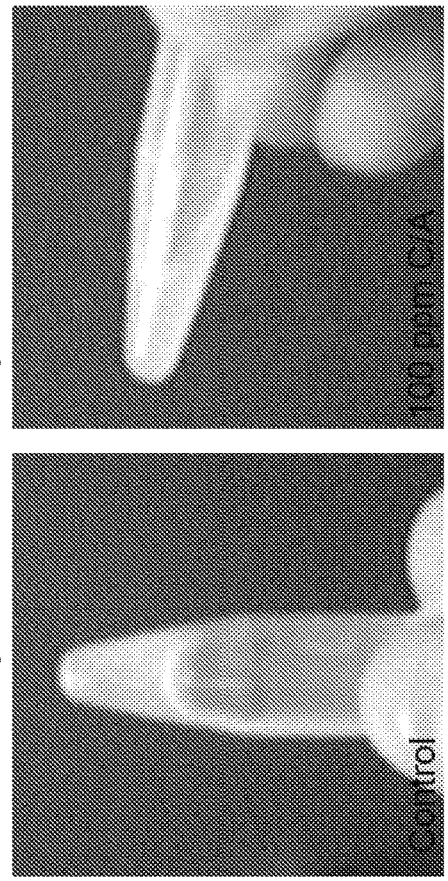
Figure 13A:
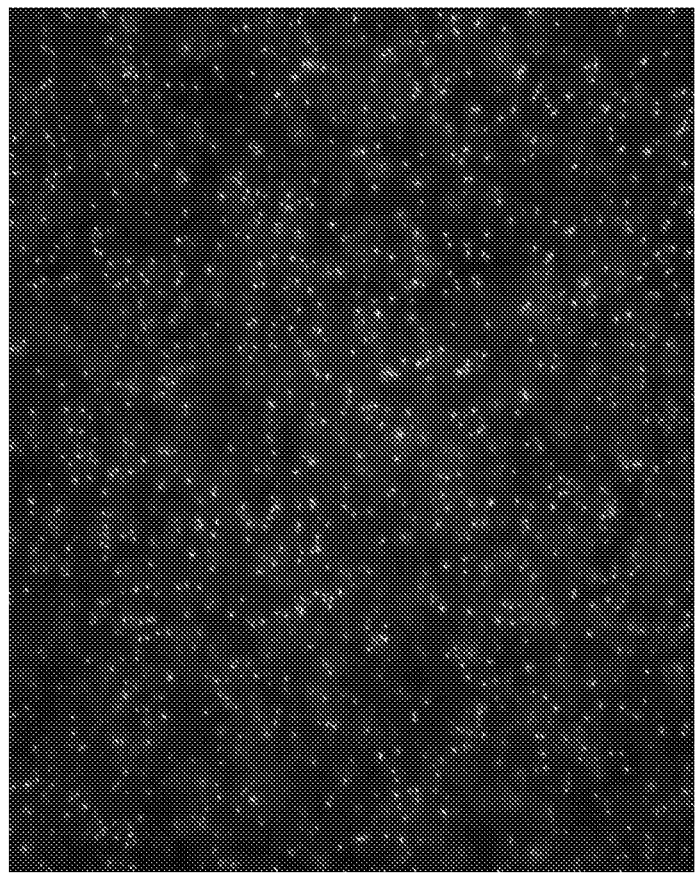
FIG. 13A shows Gram negative *Salmonella enterica* serotype *Typhimurium* (ATCC 700720) in ultra-pure water at 200× magnification.
Figure 13B:
FIG. 13B shows clumping of Gram negative *Salmonella enterica* serotype *Typhimurium* (ATCC 700720) after 1 minute exposure to chitosan-lactobionic acid (100 kDa) in ultra-pure water at 200× magnification.
Figure 14B:
FIG. 14B shows clumping of Gram positive *Clostridium perfringens* (ATCC 12919) after 1 minute exposure to chitosan-lactobionic acid (100 kDa) in ultra-pure water at 200× magnification.
Figure 14A:
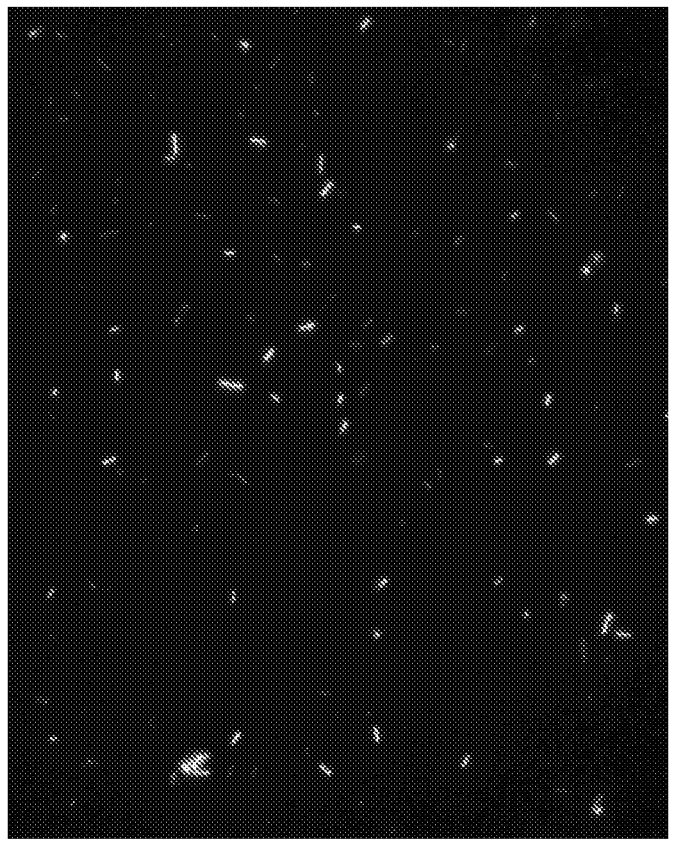
FIG. 14A shows Gram positive *Clostridium perfringens* (ATCC 12919) in ultra-pure water at 200× magnification.
Figure 15B:
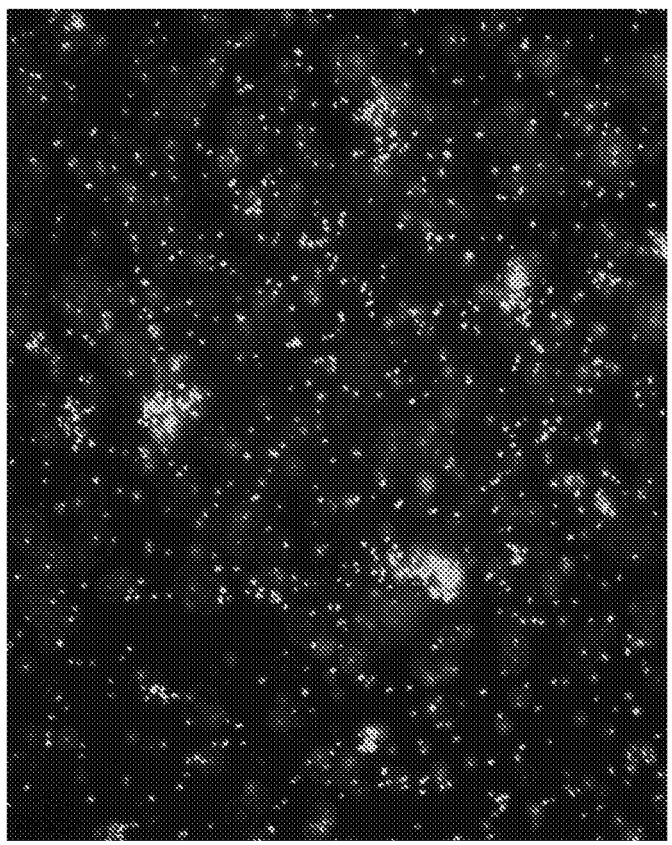
FIG. 15B shows clumping of Gram negative *Escherichia coli* (ATCC 700728) after 1 minute exposure to chitosan-lactobionic acid (100 kDa) in ultra-pure water at 200× magnification.
Figure 15A:
FIG. 15A shows Gram negative *Escherichia coli* (ATCC 700728) in ultra-pure water at 200× magnification.
Figure 16B:
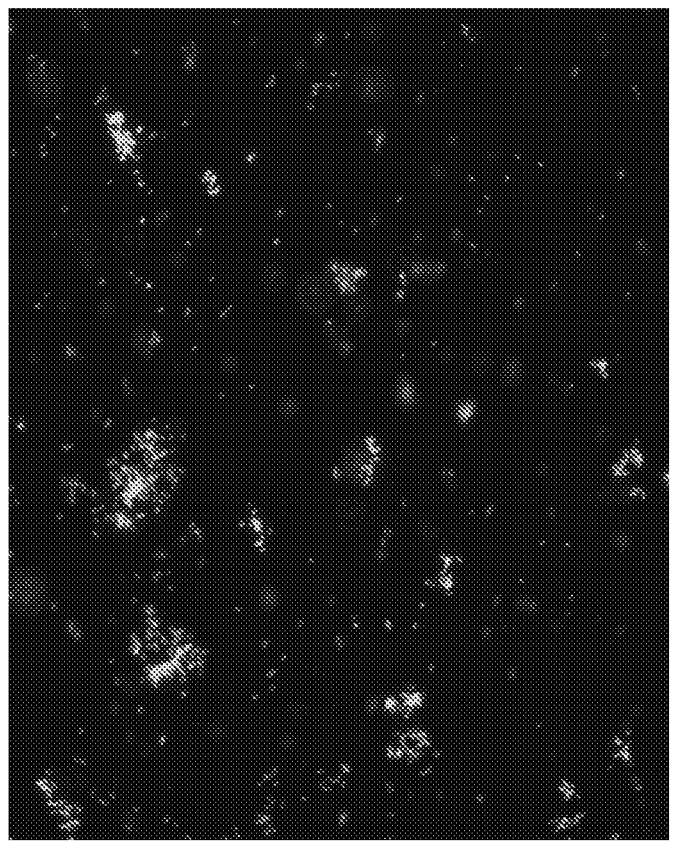
FIG. 16B shows clumping of Gram positive *Streptococcus pyogenes* (ATTC 700294D-5) after 1 minute exposure to chitosan-lactobionic acid (100 kDa) in ultra-pure water at 200× magnification.
Figure 16A:
FIG. 16A shows Gram positive *Streptococcus pyogenes* (ATTC 700294D-5) in ultra-pure water at 200× magnification.
Figure 17B:
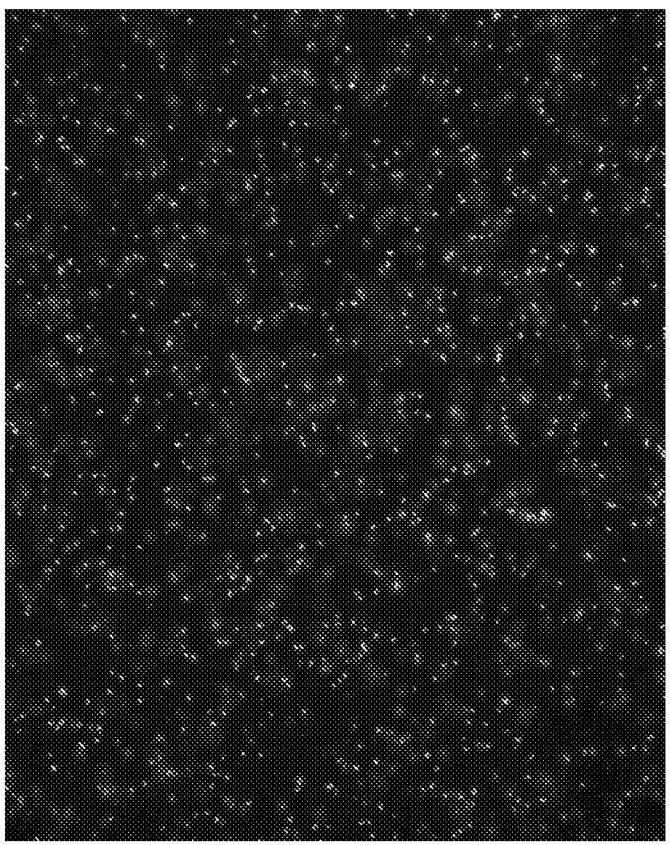
FIG. 17B shows clumping of Gram negative *Shigella flexneri* (ATCC 29903) after 1 minute exposure to chitosan-lactobionic acid (100 kDa) in ultra-pure water at 200× magnification.
Figure 17A:
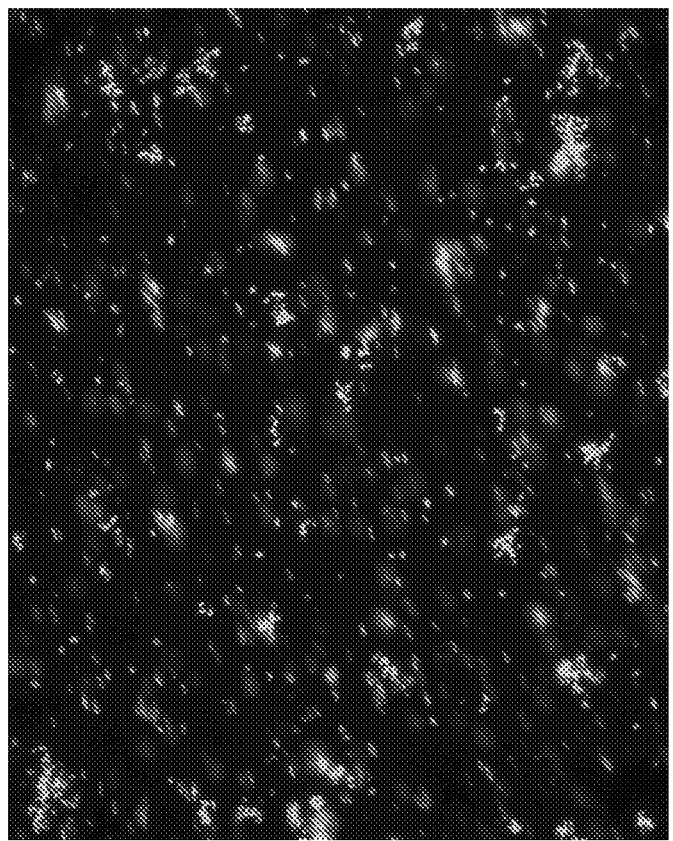
FIG. 17A shows Gram negative *Shigella flexneri* (ATCC 29903) in ultra-pure water at 200× magnification.
Figure 18B:
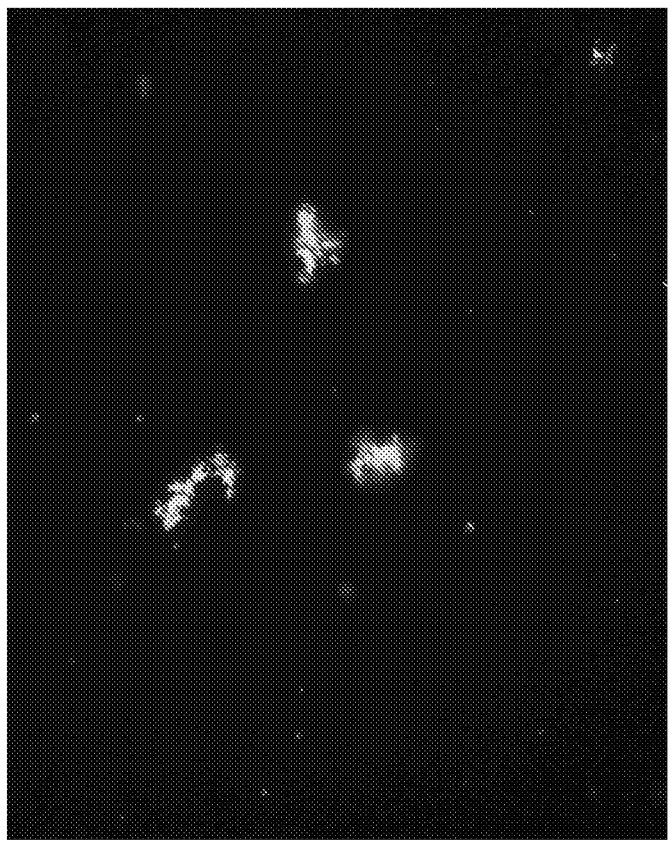
FIG. 18B shows clumping of Gram positive *Streptococcus mutans* (ATCC 35668) after 1 minute exposure to chitosan-lactobionic acid (100 kDa) in ultra-pure water at 200× magnification.
Figure 18A:
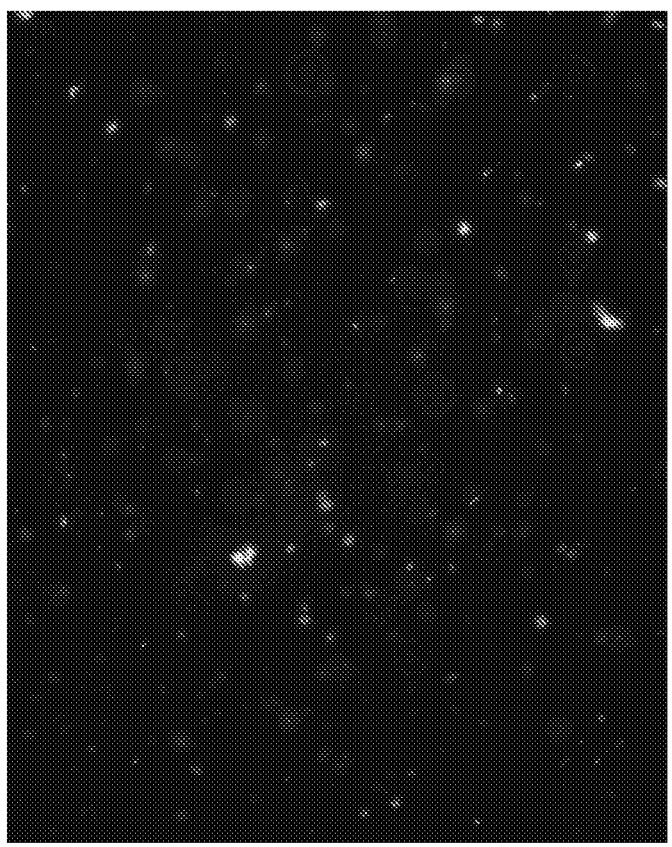
FIG. 18A shows Gram positive *Streptococcus mutans* (ATCC 35668) in ultra-pure water at 200× magnification.
Figure 19A:
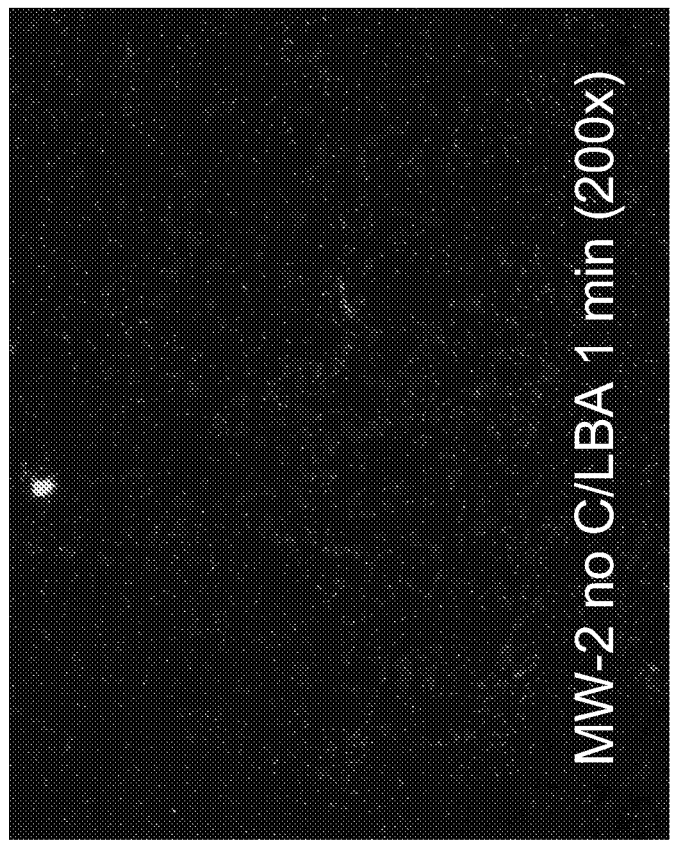
FIG. 19A shows Gram positive *Staphylococcus aureus* strain MW-2 (clinical isolate from blood/CSF of community acquired disseminating infection) in ultra-pure water at 200× magnification.
Figure 19B:
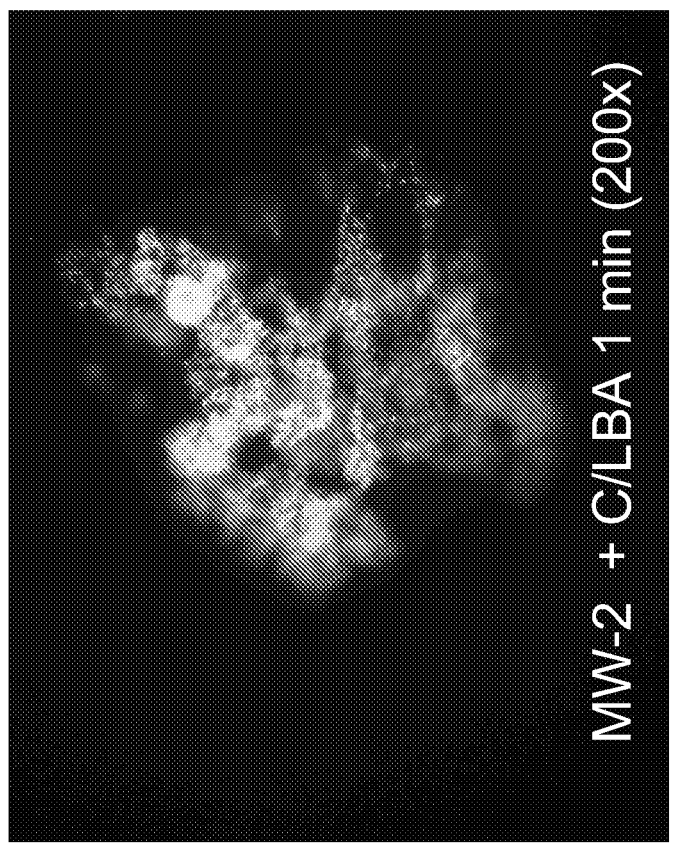
FIG. 19B shows clumping of Gram positive *Staphylococcus aureus* strain MW-2 (clinical isolate from blood/CSF of community acquired disseminating infection) after 1 minute exposure to chitosan-lactobionic acid (277 kDa) in ultra-pure water at 200× magnification.
Figure 19B:
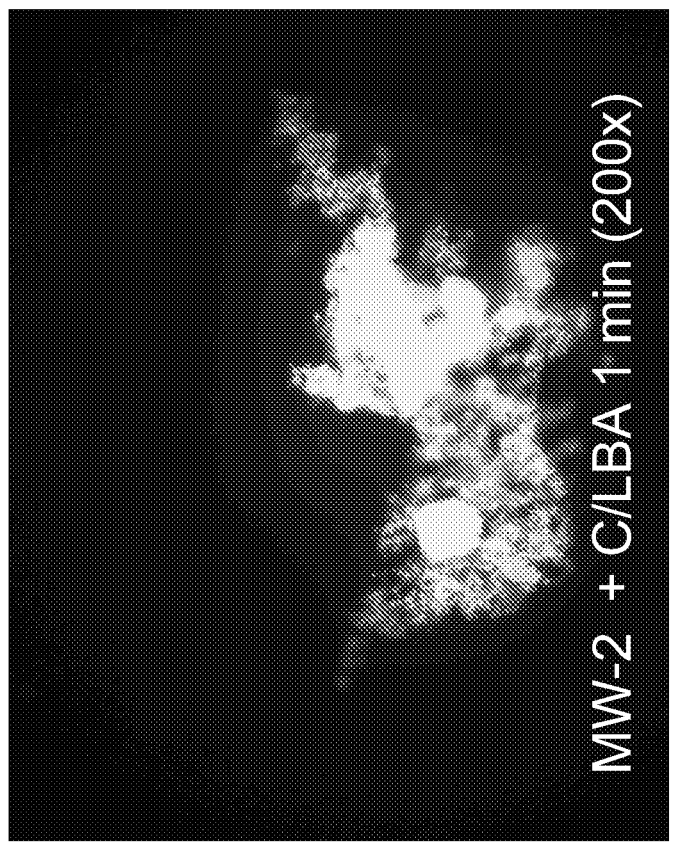

Both control sputum samples were unable to pour, however the chitosan-arginine treated sputum was pourable as shown in FIG. 12. This qualitatively demonstrates the ability of chitosan-arginine to reduce the viscosity of viscous sputum associated with cystic fibrosis.

Example 8. Tobramycin Synergy Experiment

Chronic antibacterial treatment of *Pseudomonas aeruginosa* infections in the lungs of cystic fibrosis patients is thought to facilitate antibacterial resistance (Speert et al., 1990; Govan & Deretic, 1996). Recently, sub-inhibitory aminoglycoside concentrations have been associated with induction of biofilm formation by *P. aeruginosa* (Hoffman et al., 2005).

A checkerboard assay was used to screen 64 unique combinations of antimicrobial concentrations in triplicate. For each study, approximately $10^5$ cells per mL were treated with chitosan-arginine (64-0.5 µg/mL) and/or tobramycin (4-0.031 µg/mL). Bacteria were incubated at 37° C. for 20 hours. The fluorescent pigment pyocyanin produced by *Pseudomonas aeruginosa* can be correlated with bacterial growth. The Minimum Inhibitory Concentration (MIC) values obtained with this protocol (fluorescence was measured 485 nm excitation, 535 nm emission) are the same as those obtained using optical density (Hoffman et. al., 2005).

Three independent checkerboard assays were completed in triplicate using different lots of chitosan-arginine and tobramycin with the MIC of each antimicrobial alone reported in Table 6 (column 1). The amounts of chitosan-arginine (ag/ml) co-administered are in bold. The tobramycin MIC reported in response to co-administered C/A is noted above the bolded values. It is clear that the addition of 0.5 ag/ml chitosan-arginine caused the MIC of tobramycin to be reduced 4 to 8-fold. The MIC of tobramycin is reduced 8 to 32-fold upon the addition of 4 µg/ml of chitosan-arginine (Table 6).

TABLE 6

Summary of the MIC data and FIC calculations to determine synergy

| MIC Antimicrobial Alone (µg/ml) | | Tobramycin MIC (µg/ml) | | | FIC |
|---|---|---|---|---|---|
| | | 0.125 | 0.063 | 0.031 | |
| $CA^1$ (16) | Tobramycin (1) | C/A Treatment (µg/ml) | 0.5 | 2 | 4 | ≤0.28 $(S)^4$ |
| $C/A^2$ (32) | Tobramycin (0.5) | | 0.5 | 2 | 4 | ≤0.27 (S) |

TABLE 6-continued

Summary of the MIC data and FIC calculations to determine synergy

| MIC<br>Antimicrobial Alone | | Tobramycin<br>MIC (μg/ml) | | | |
|---|---|---|---|---|---|
| (μg/ml) | | 0.125 | 0.063 | 0.031 | FIC |
| C/A³ (32) | Tobramycin<br>(0.5) | 0.5 | 4 | 8 | ≤0.30 (S) |

[1]27%, 32 kDa;
[2]31%, 54 kDa;
[3]25%, 40 kD;
[4](S) = Synergistic

All of the treatment concentrations shown in Table 6 were shown to exhibit synergistic relationships as defined by the Fractional Inhibitory Concentration (FIC). The FIC is an interaction coefficient indicating whether the combined inhibitory/bacteristatic effect of drugs is synergistic, additive or antagonistic (FIC=A+B) where: A=(MIC of X with Y)/(MIC of drug X alone) and, B=(MIC of Y with X)/(MIC of drug Y alone). If the FIC<0.5 the relationship is synergistic, additive if the FIC=1, or antagonistic if the FIC>4.

These analyses determined that co-administration of tobramycin and chitosan-arginine is synergistic. Specifically, chitosan-arginine lowers the MIC of tobramycin and works synergistically to eliminate *Pseudomonas aeruginosa*.

Example 9. Neutral Soluble Chitosan Derivative Clumping

Figure 20:
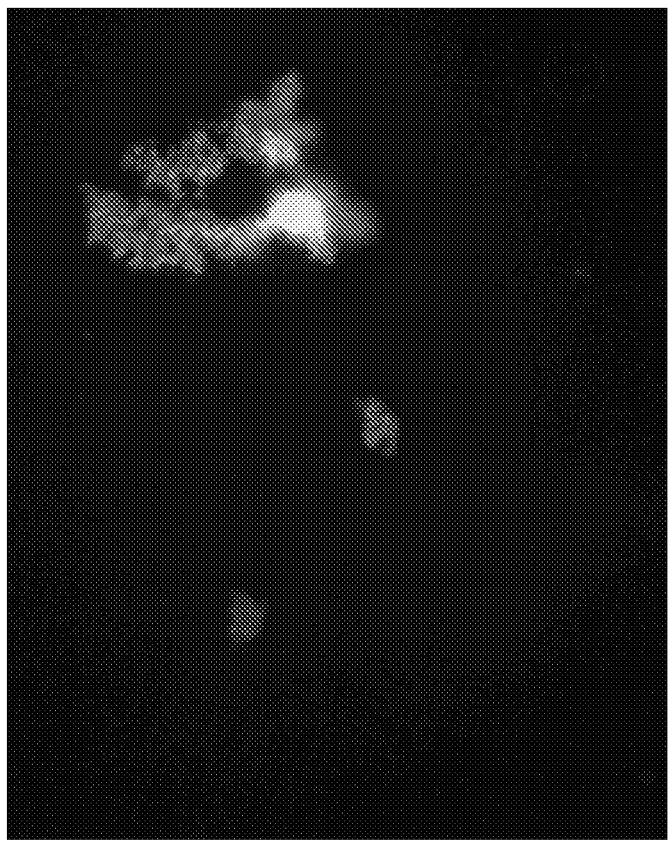
FIG. 20 shows clumping of Gram negative *Pseudomonas aeruginosa* strain PA01 after 1 minute exposure to chitosan-lactobionic acid (100 kDa) in ultra-pure water at 200× magnification.

The ability of chitosan-lactobionic acid (LOT 007; about 100 kDa), a neutral charge chitosan derivative, to clump various bacterial species was evaluated using SYTOX green/propidium iodide staining after a 1-minute incubation with either treatment. As shown in FIGS. 13-20 (magnification 200×), chitosan-lactobionic acid is able to clump these bacteria within a minute of exposure, similar to chitosan-arginine. Bacteria tested were *Salmonella enterica* serotype *Typhimurium* (FIG. 13), *Clostridium perfringens* (FIG. 14), *Escherichia coli* strain O157:H7 (FIG. 15), *Streptococcus pyogenes* also know as Group A Strep (FIG. 16), *Shigella flexneri* (FIG. 17), *Streptococcus mutans* (FIG. 18), methicillin resistant *Staphylococcus aureus* strain MW-2 (FIG. 19), and *Pseudomonas aeruginosa* strain PA01 (FIG. 20, see FIG. 1A for untreated control). FIGS. 13-19A depict the bacteria before treatment (control) compared to FIGS. 13-19B after 1-minute treatment with 100 g/ml of chitosan-lactobionic acid. This observation demonstrates that innate properties of the chitosan backbone, in addition to or instead of the positive charge provided by positive derivatives, is a critical component of the clumping mechanism. This observation also demonstrates that neutral derivatives can be effectively used for clumping in addition to positively charge derivatives.

Example 10. Wound Biofilms

Figure 21:
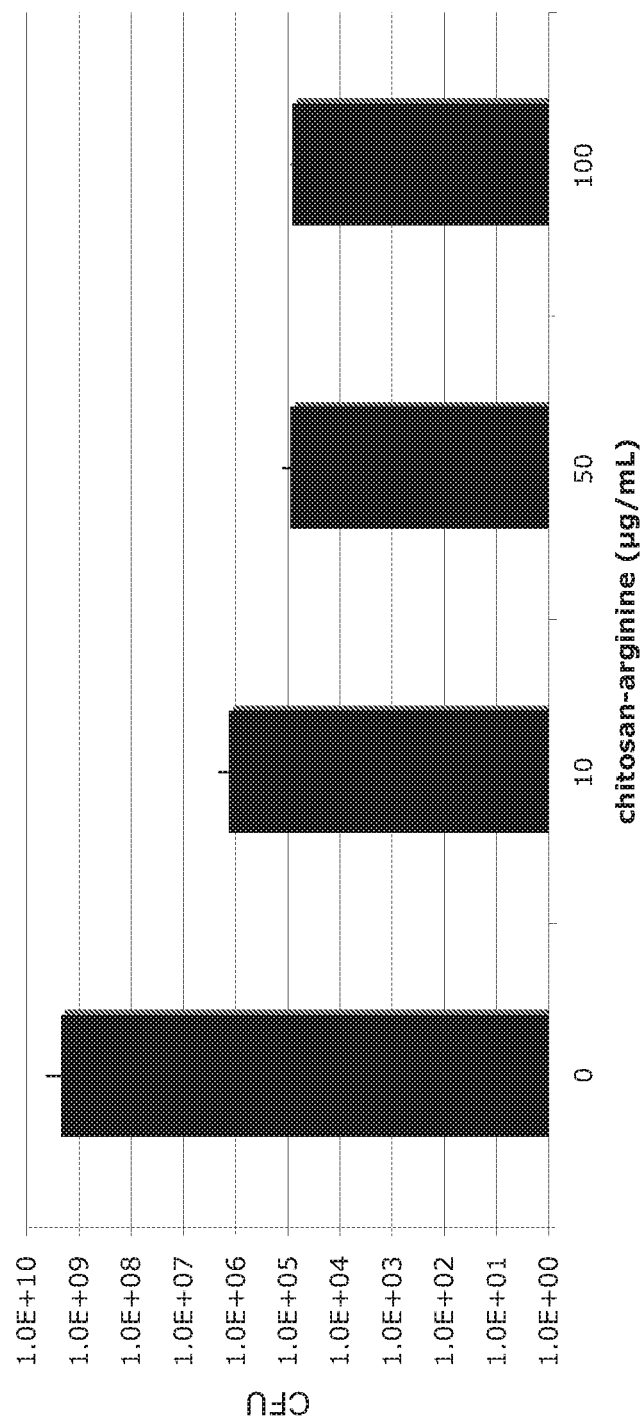
FIG. 21 shows the reduction of *Staphylococcus aureus* strain MW-2 (clinical isolate from blood/CSF of community acquired disseminating infection) biofilms by chitosan-arginine (24 kDa, 28% functionalized, 18% DDA, 1.5 PDI).

Bacteria associated with wound biofilms were also tested for sensitivity to chitosan-arginine. Methicillin resistant *Staphylococcus aureus* strain MW-2 biofilms were grown up in THB stationary at 37° C. for 2.5 days. The biofilms were rinsed and treated with 0, 10, 50, or 100 μg/ml of chitosan-arginine (24 kDa, 28% functionalization, 83% DDA, 1.5 PDI), in triplicate for 4 hours. Then the biofilms were scraped from the wells, diluted and plated to obtain CFU. FIG. 21 shows a 3-log reduction with 10 μg/ml after 4-hours and 4-log reduction at 50 and 100 μg/ml.

Figure 22:
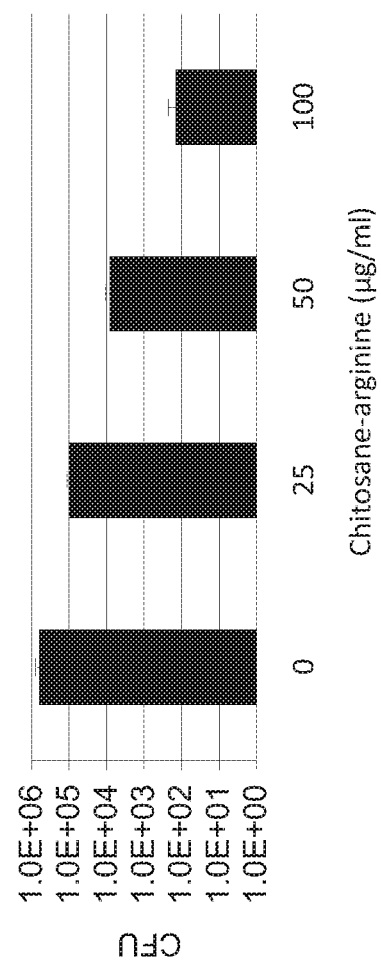
FIG. 22 shows the reduction of Gram negative *Pseudomonas aeruginosa* strain PA01 biofilms by chitosan-arginine (24 kDa, 28% functionalized, 18% DDA, 1.5 PDI).

Chitosan-arginine efficacy against wound pathogen *Pseudomonas aeruginosa* strain PA01 biofilms was also tested. Biofilms were grown for 3 days in 12 well plates in yeast extract and treated with 25, 50, or 100 μg/ml chitosan-arginine for 6-hours. The virtual CFU were enumerated following the technique of Brewster (Brewster, 2003). *Pseudomonas aeruginosa* strain PA01 biofilms are significantly reduced after 6-hour incubation with chitosan-arginine as seen in FIG. 22. A marked dose response was also observed as the concentration of chitosan-arginine was increased from 25-100 μg/ml. The highest dose (100 μg/ml) reduced the virtual CFU by 4 logs with a decrease in efficacy as seen in the figure at lower doses. It is notable that almost half of the data points for the replicates of the 100 g/ml chitosan-arginine treatment did not show any growth at all.

Example 11. Disc Diffusion Assay

Figure 23:
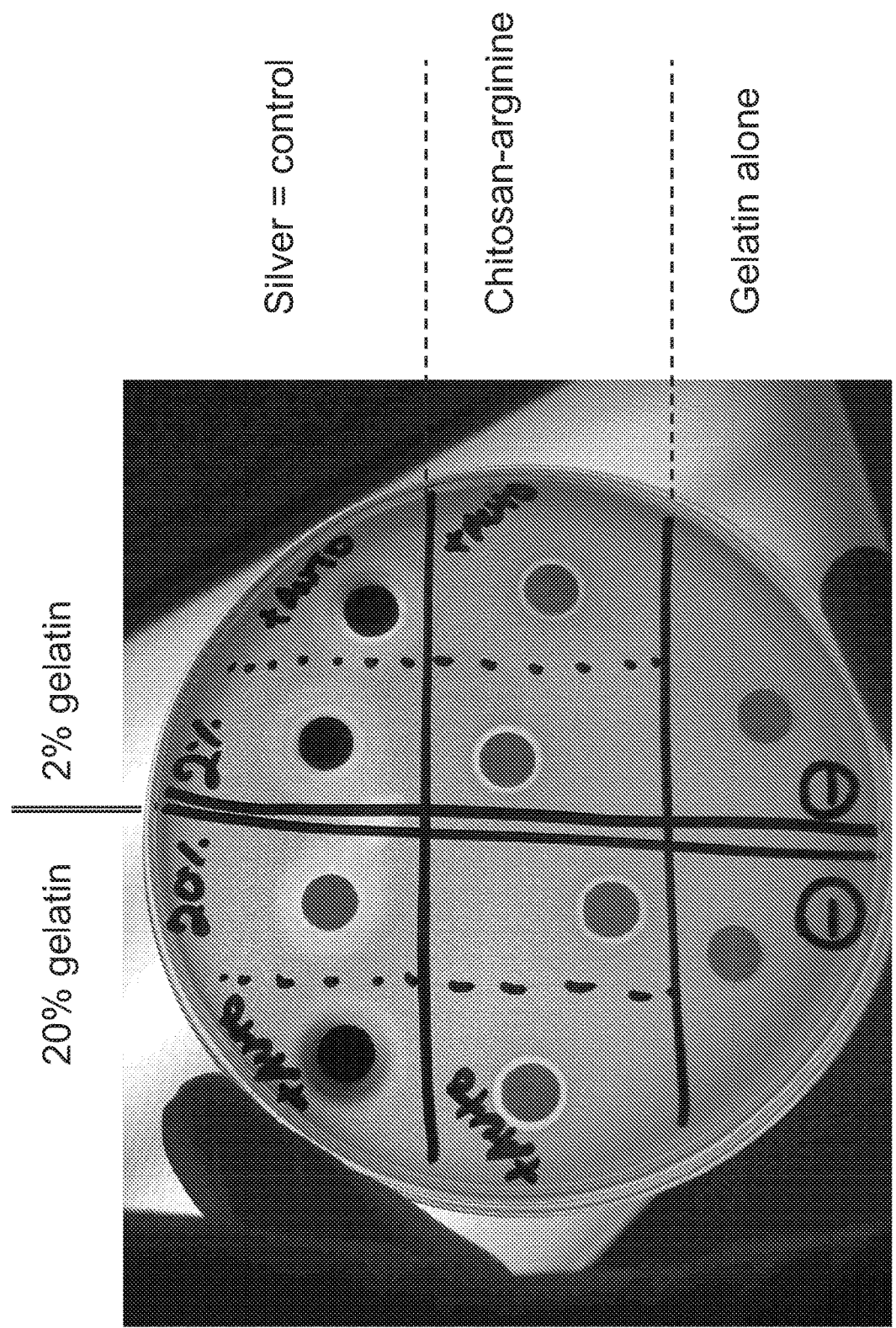
FIG. 23 shows the diffusion of chitosan-arginine from 2% and 20% gelatin formulations in disc diffusion assay. +Auto=autoclaved material.

To test the ability of chitosan-arginine to diffuse from 2% or 20% gelatin formulation, antibiotic test wafers were impregnated with 50 mM silver nitrate (positive control), gelatin alone (negative control), or chitosan-arginine (31%, 9 kDa). Following 18 h incubation at 37° C., diffusion was evident by the observation of a zone of inhibition that occurred around the discs (either autoclave or not) that contained the 9 kDa chitosan-arginine delivered in 2 or 20% gelatin, as shown in FIG. 23. In this instance, autoclaving did not have an effect on activity.

This example suggests that the ability of chitosan-arginine to be delivered in a viscous or gel-like substance facilitates the slow release of chitosan-arginine into the local area of treatment. Maintaining a higher concentration of chitosan-arginine over an extended period of time can extend the spectrum of antibacterial activity and reduces the need for re-application.

Figure 24:
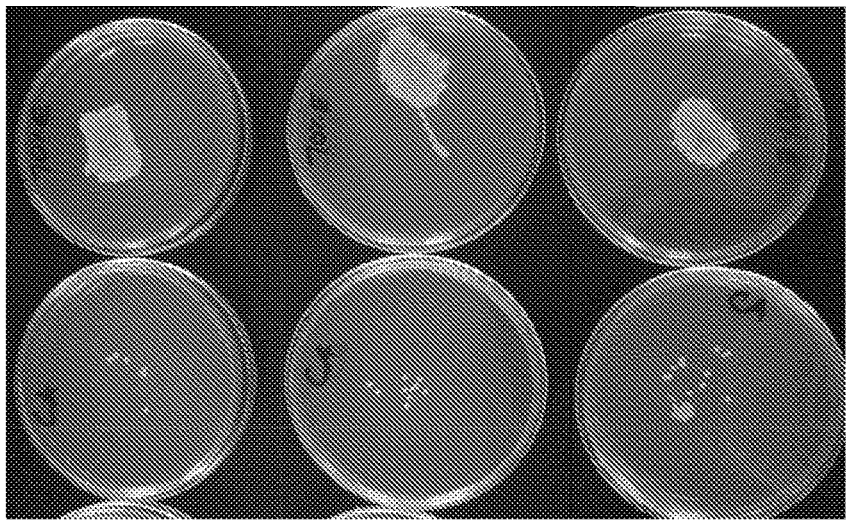
FIG. 24 shows chitosan-arginine (21 kDa, 29% functionalized, 88% DDA, 1.49 PDI) prophylactic activity against MRSA MW-2 (ATCC BAA-1707) compared to other skin decontamination solutions after 1-hour on pigskin. Data is qualitative CFU recovered after 1-hour on the treated skin surface.
Figure 24:
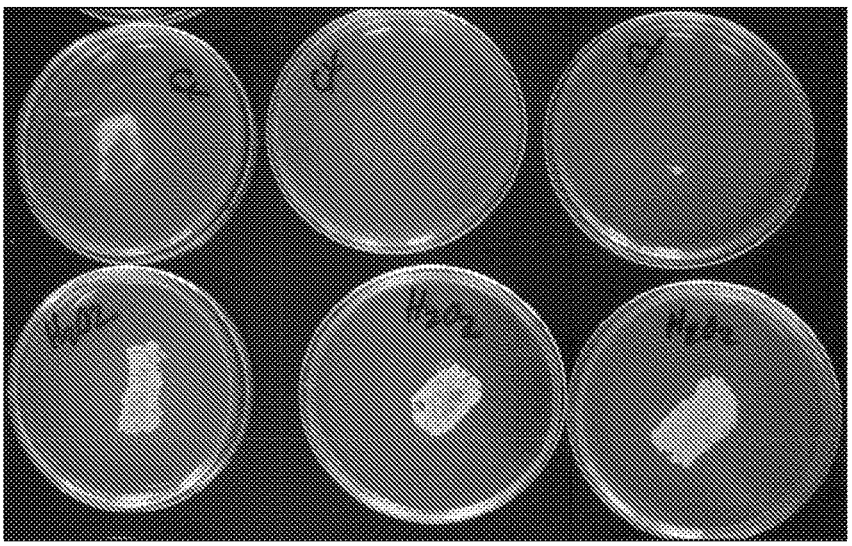
Figure 24:
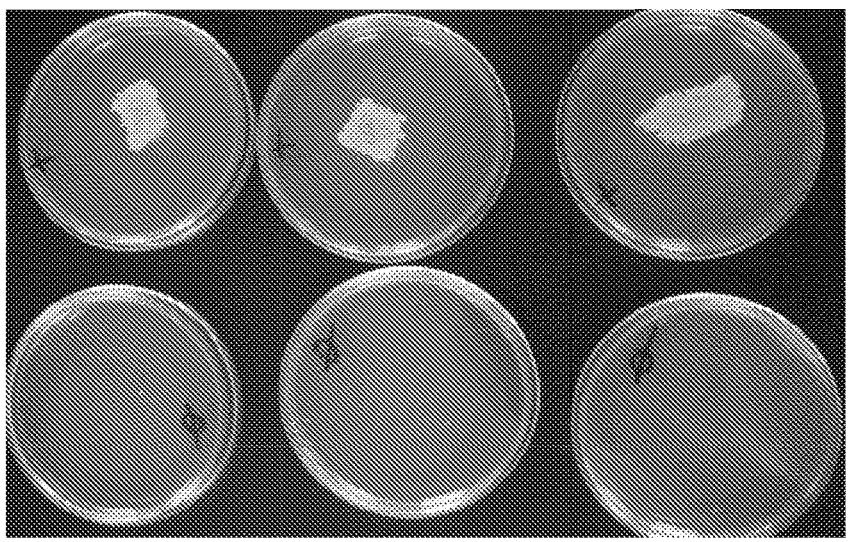

Example 12. The Prophylactic Activity of Chitosan-Arginine Against MRSA on Pigskin Pigskin was obtained from Sinclair Research Center, Inc. (Colombia, MO) shaved, cleaned, and divided into 1-inch square sections. Each skin used was placed in sterile Petri dishes and UV sterilized on both sides for 1-hour each to prepare for testing. In triplicate each skin was treated with 3% hydrogen peroxide, 70% ethanol, Chloroprep (commercial product consisting of 2% chlorohexidine in 70% ethanol), and 60 ag/cm² chitosan-arginine in 70% ethanol, or no treatment and allowed to dry for 1-hour. Approximately $10^3$ CFU of MRSA MW-2 was placed onto the pigskins and left at room temperature to adhere for 1-hour. Three pieces were excluded from treatment for controls to indicate sterilization of the skin occurred. The skin surface was pressed onto a BHI agar plate to obtain a qualitative indication of the amount of bacteria remaining on the skin surface. As shown in FIG. 24, chitosan-arginine and Chloroprep maintained good prophylactic activity while hydrogen peroxide and 70% ethanol had no prophylactic activity.

Figure 25:
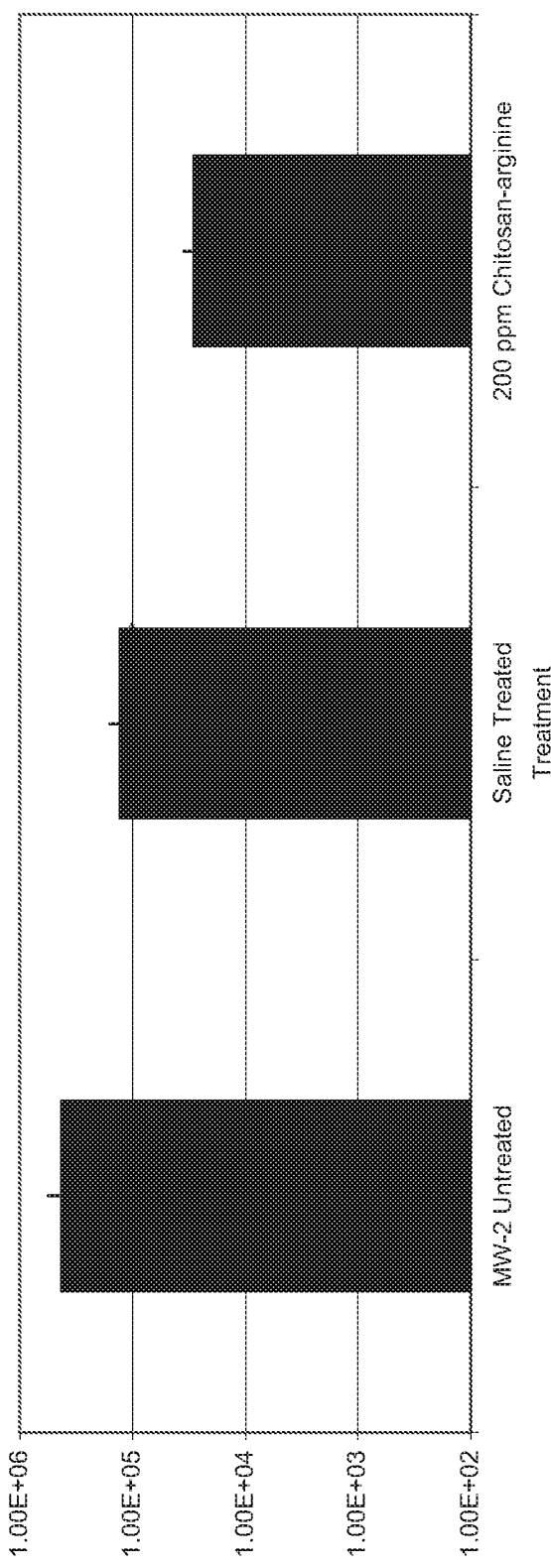
FIG. 25 shows chitosan-arginine (43 kDa, 25% functionalized, 88% DDA, 2.28 PDI) wound rinse activity against MRSA MW-2 (ATCC BAA-1707) contaminated abraded pigskin. Data is CFU recovered 30 minutes after two 5 mL rinses.
Figure 26:
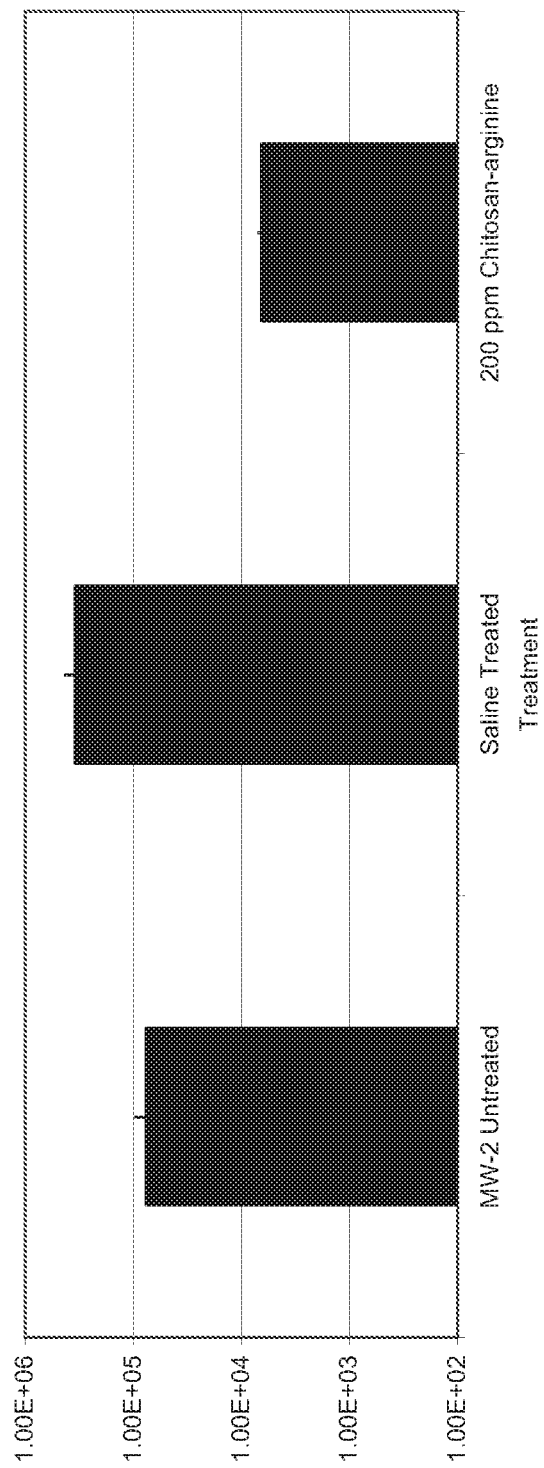
FIG. 26 shows chitosan-arginine (43 kDa, 25% functionalized, 88% DDA, 2.28 PDI) wound rinse activity against *Pseudomonas aeruginosa* PA01 (ATCC BAA-47) contaminated abraded pigskin. Data is CFU recovered 30 minutes after two 5 mL rinses.

Example 13. The Wound Rinse Activity of Chitosan-Arginine Against Bacteria Contaminated Abraded Pigskin Pigskin was obtained from Sinclair Research Center, Inc. (Colombia, MO) shaved, cleaned, and divided into 1-inch square sections. Each skin used was placed in sterile Petri dishes and UV sterilized on both sides for 1-hour each to prepare for testing. Then pigskins were abraded repeatedly with a hypodermic needle and approximately $10^5$ CFU of MRSA (FIG. 25) pr *P. aeruginosa* (FIG. 26) was placed in triplicate onto the pigskins and left at room temperature to adhere for 30 minutes. Controls consisted of abraded skin only and abraded skin with bacterial contamination left untreated. The skins were irrigated with syringes twice with 5 mL of chitosan-arginine (43 kDa, 25% functionalized, 88% DDA, 2.28 PDI) and left at room temperature for 30 minutes. Following treatment the pigskin were placed in 10 ml of PBS, sonicated and the remaining CFU were enumerated by plate counts. Chitosan-arginine was shown to rinse away more bacteria than the standard of care (saline).

Example 14. Chitosan-Arginine Dose Response Against Stationary MRSA Biofilms

Figure 27:
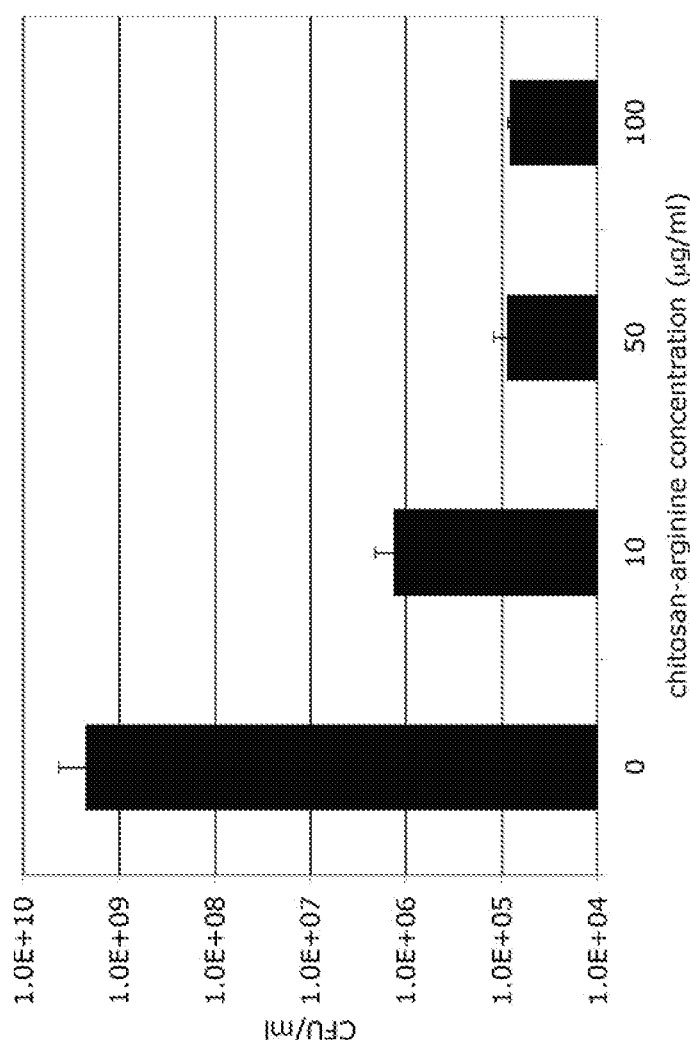
FIG. 27 shows chitosan-arginine (43 kDa, 25% functionalized, 88% DDA, 2.28 PDI) dose response against stationary MRSA MW-2 (ATCC BAA-1707) 2 day-old biofilms. Data is CFU recovered after 4-hour treatment.

The MRSA MW-2 biofilms were grown in 12-well untreated tissue culture plates containing BHI media for approximately 3 days. The biofilms were rinsed with water three times and treated with increasing doses of chitosan-arginine for 4-hours. Following treatment the biofilms were rinsed three times and the chitosan-arginine treated biofilms were resuspended, sonicated, diluted and plated to obtain CFU remaining. As shown in FIG. 27, a 4-log reduction was achieved with 50 µg/ml treatment.

Figure 28:
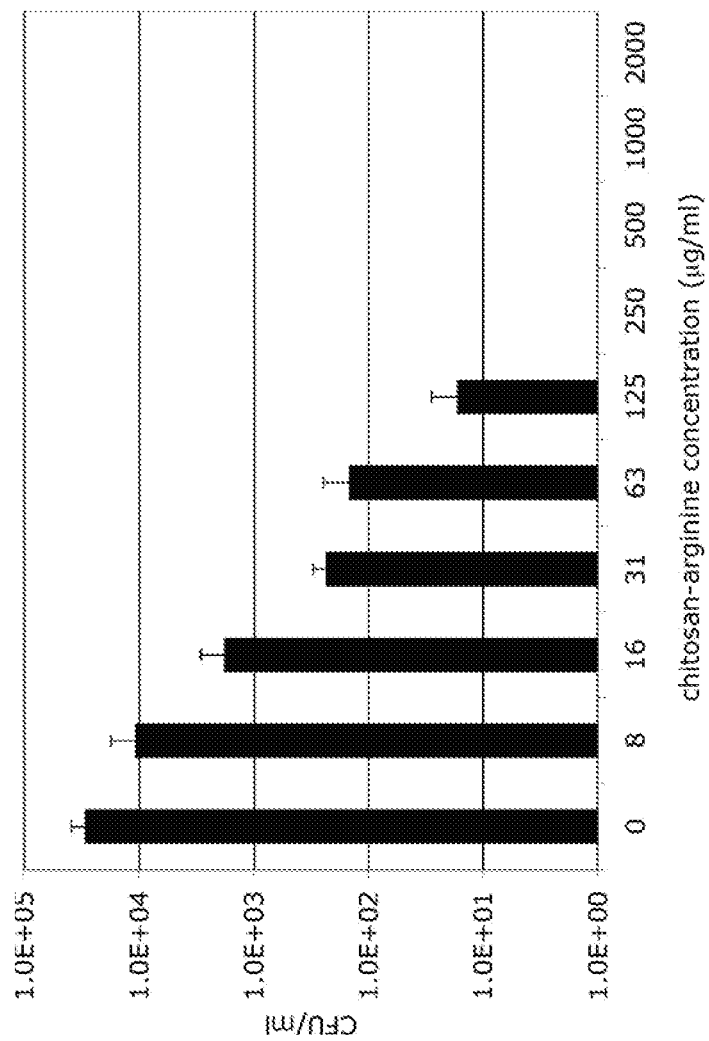
FIG. 28 shows chitosan-arginine (43 kDa, 25% functionalized, 88% DDA, 2.28 PDI) dose response against *Klebsiella pneumoniae* (ATCC 13883) 2 day-old biofilms grown on pegs. Data is CFU recovered after 5-hour treatment. The * indicates sterilization.

Example 15. Chitosan-Arginine Dose Response Against *Klebsiella pneumoniae* Biofilms Chitosan-arginine was analyzed with respect to reduction of mature *K. pneumoniae* biofilms with previously established methods (Harrison, J. J. et al. (2005) High-throughput metal susceptibility testing of microbial biofilms Environ Microbiol 7, 981-994). The biofilms were grown according to MBEC™ for High-throughput Screening (Innovotech, Edmonton, AB Canada) methods on a peg lid placed in trough containing LB media for 36 hours. The pegs were rinsed and placed into a 96-well plate with serial dilutions of the chitosan derivative or controls and exposed for 5-hours at room temperature. The biofilms were rinsed, and the pegs removed and placed into microfuge tubes in 200 µl of water. The tubes were sonicated to remove the peg biofilm. Aliquots of recovered biofilms were diluted and plated onto LB agar to quantify growth. Testing was done in duplicate and representative assays are depicted. The *K. pneumoniae* biofilms showed that the bacterial CFU were significantly reduced by chitosan-arginine. As shown in FIG. 28, a 3-log reduction was observed with 125 µg/ml treatment.

Figure 29:
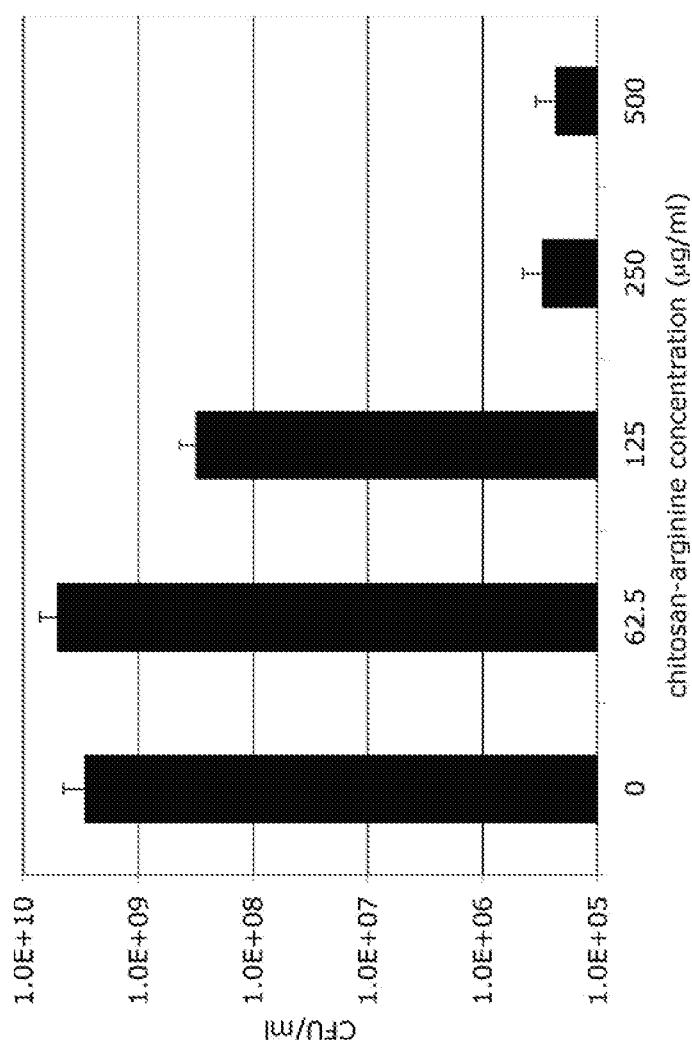
FIG. 29 shows chitosan-arginine (43 kDa, 25% functionalized, 88% DDA, 2.28 PDI) dose response against *Acinetobacter baumannii* (ATCC 19606) 2 day-old biofilms grown on pegs. Data is CFU recovered after 3-hour treatment.

Example 16. Chitosan-Arginine Dose Response Against *Acinetobacter baumannii* Biofilms Chitosan-arginine was analyzed with respect to reduction of mature *A. baumannii* biofilms with previously established methods (Harrison, J. J. et al. (2005) High-throughput metal susceptibility testing of microbial biofilms Environ Microbiol 7, 981-994). The biofilms were grown according to MBEC™ for High-throughput Screening (Innovotech, Edmonton, AB Canada) methods on a peg lid placed in trough containing LB media for 36 hours. The pegs were rinsed and placed into a 96-well plate with serial dilutions of the chitosan derivative or controls and exposed for 3-hours at room temperature. The biofilms were rinsed, and the pegs removed and placed into microfuge tubes in 200 µl of water. The tubes were sonicated to remove the peg biofilm. Aliquots of recovered biofilms were diluted and plated onto LB agar to quantify growth. Testing was done in duplicate and representative assays are depicted. The *A. baumannii* biofilms showed that the bacterial CFU were significantly reduced by chitosan-arginine. As shown in FIG. 29, a 4-log reduction was observed with 250 µg/ml treatment.

Figure 30:
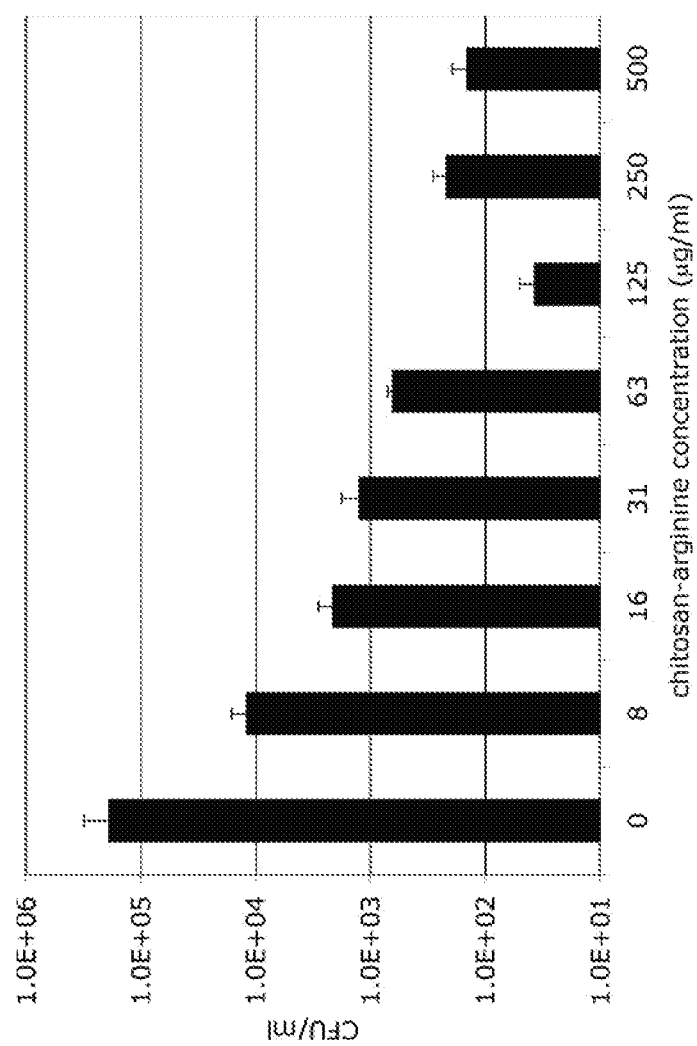
FIG. 30 shows chitosan-arginine (43 kDa, 25% functionalized, 88% DDA, 2.28 PDI) dose response against *Pseudomonas aeruginosa* (ATCC BAA-47) 2 day-old biofilms grown on pegs. Data is CFU recovered after 3-hour treatment.

Example 17. Chitosan-Arginine Dose Response Against *Pseudomonas aeruginosa* Biofilms Chitosan-arginine was analyzed with respect to reduction of mature *P. aeruginosa* biofilms with previously established methods (Harrison, J. J. et al. (2005) High-throughput metal susceptibility testing of microbial biofilms Environ Microbiol 7, 981-994). The biofilms were grown according to MBEC™ for High-throughput Screening (Innovotech, Edmonton, AB Canada) methods on a peg lid placed in trough containing LB media for 36 hours. The pegs were rinsed and placed into a 96-well plate with serial dilutions of the chitosan derivative or controls and exposed for 3-hours at room temperature. The biofilms were rinsed, and the pegs removed and placed into microfuge tubes in 200 µl of water. The tubes were sonicated to remove the peg biofilm. Aliquots of recovered biofilms were diluted and plated onto LB agar to quantify growth. Testing was done in duplicate and representative assays are depicted. The *A. baumannii* biofilms showed that the bacterial CFU were significantly reduced by chitosan-arginine. As shown in FIG. 30, a 3-log reduction in CFU was observed with 125 µg/ml chitosan-arginine treatment.

Figure 31:
FIG. 31 depicts mixed wound biofilms (MRSA MW-2 ATCC BAA-1707, *Pseudomonas aeruginosa* ATCC BAA-47, and Vancomycin-resistant *Enterococcus faecalis* ATCC 51299) grown in a flow cell overnight then treated with either water or 200 µg/mL chitosan-arginine (43 kDa, 25% functionalized, 88% DDA, 2.28 PDI) twice daily for two days and finally rinsed and sonicated for 30 seconds and stained with crystal violet.
Figure 32:
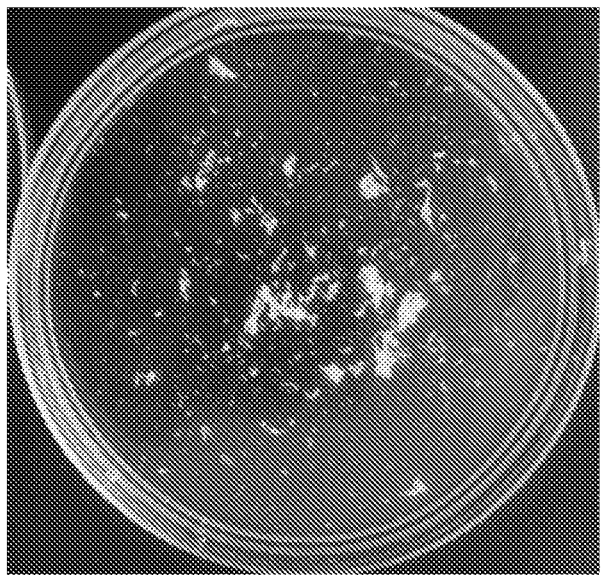
FIG. 32 depicts the amount and consistency of material removed following the final rinse from flow cells treated with either water or chitosan-arginine (43 kDa, 25% functionalized, 88% DDA, 2.28 PDI) in FIG. 32.
Figure 32:
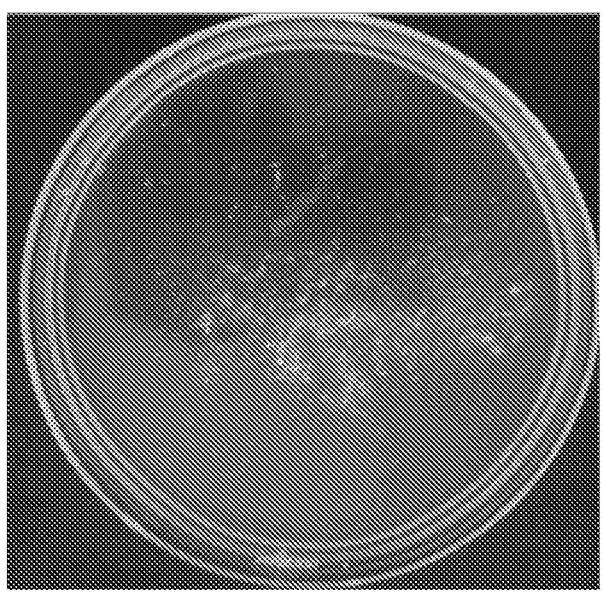

Example 18. The Ability of Chitosan-Arginine to Reduce the Cohesion of Mixed Biofilms The interactions of chitosan derivatives with biofilms were evaluated in more detail in order to determine the effect of mixed wound infections. In these experiments mixed bacterial populations consisting of MRSA MW-2, *P. aeruginosa* PA01, and Vancomycin-resistant *E. faecalis* were use to initiate biofilm growth in a flow cell to examine biofilm cohesion and in an artificial model. This experiment examined the ability of chitosan-arginine to reduce the cohesion of mixed biofilms. Each convertible flow cell slide chamber (Stovall Life Science Inc., CFCAS0003) was assembled into the convertible flow cell apparatus (Stovall Life Science Inc., CFCAS0001) including a bubble trap (Stovall Life Science Inc., ACCFL0002). The bacteria were grown overnight in LB media at 37° C. under anaerobic conditions, centrifuged and resuspended approximately $10^8$ cfu/ml of each in LB media. Each flow cell was primed with approximately 10 ml of the bacterial suspension. An initial attachment phase was carried out for 1-hour with a flow rate of 1.5 ml/min facilitated by an IsmaTec Low Flow, High Accuracy Multichannel Peristaltic Pump (Stovall Life Science Inc., ACCFL0013). Following the attachment phase the flow cells were rinsed and LB media was pumped in at a flow rate of 0.24 ml/min for 8-hours. The flow cells were rinsed for 2 minutes at approximately 29 ml/min with either water or chitosan-arginine at 200 µg/ml then media pumping was resumed overnight. Rinses were repeated at 22 and 26 hours post attachment. For the final rinse the flow cells were disconnected and place in a Petri dish full of water for 5 minutes. Excess water was wiped or drained from the slide careful not to disrupt the biofilm, then dried in a humid chamber 37° C. for 10 minutes. Cohesion was examined by submerging each slide in a beaker of water then sonicating for 30 seconds at amplitude 18 jam at the liquid surface. The slides were removed and excess water was wiped or drained from the slide careful not to disrupt the biofilm, then dried in a humid chamber 37° C. for 10 minutes. The slides were stained with crystal violet for 2-minutes, rinsed and qualitative assessment of biofilm remaining following mechanical disruption to simulate debridement was completed. As shown in FIG. 31, Mixed biofilms treated with chitosan-arginine were less cohesive and were more easily dispersed than untreated biofilms. Further, as shown in FIG. 32, the material removed from the chitosan-arginine treated flow cell during the final rinse was more aggregated and dense and in a larger amount than the untreated mixed biofilm.

Figure 33:
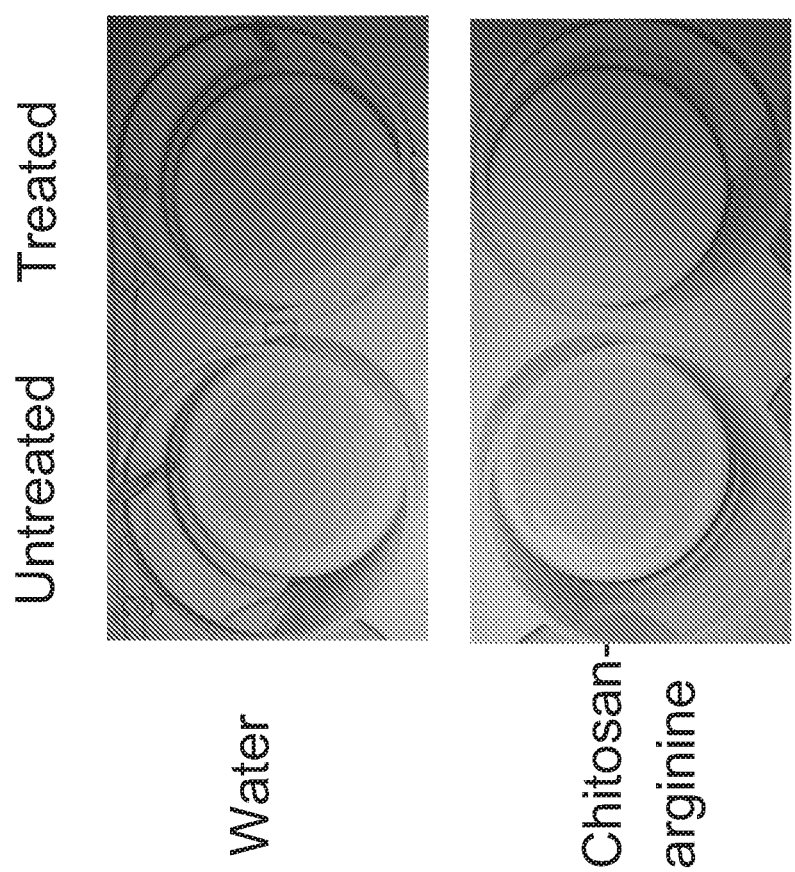
FIG. 33 depicts the immediate dispersal of *Acinetobacter baumannii* (ATCC 19606) 2-day old stationary biofilms treated with 100 µg/ml chitosan-arginine (43 kDa, 25% functionalized, 88% DDA, 2.28 PDI). The biofilms were rinsed, stained with crystal violet and treated with either water or chitosan-arginine for 5 minutes and rinsed.

Example 19. The Effect of Chitosan-Arginine on *Acinetobacter baumannii* Biofilms The *Acinetobacter baumannii* biofilms were grown in 12-well untreated tissue culture plates containing LB media for approximately 3 days. The biofilms were rinsed with water three times and stained with crystal violet for 2 minutes. The biofilms were then rinsed with water three times then treated with 100 μg/ml of chitosan-arginine or water for 5-minutes. Following treatment the biofilms were rinsed three times. As shown in FIG. 33, chitosan-arginine treated biofilms were removed from the surface while the water only treated biofilm was unaffected.

What is claimed is:

1. A method of reducing the viscosity of viscous sputum in the respiratory system of a human subject having cystic fibrosis, the method comprising:
    administering to the subject by inhalation a therapeutically effective amount of a composition comprising a derivatized chitosan, wherein the derivatized chitosan comprises a chitosan of the following formula (I):

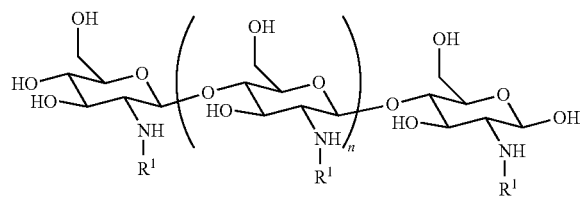

formula (I)

wherein:
n is an integer between 20 and 6000; and
each $R^1$ is independently selected for each occurrence from hydrogen, acetyl, and a group of formula (II):
wherein, formula (II) is selected from

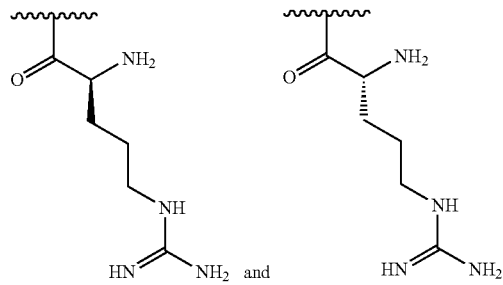 [SMILES: *C(=O)[C@@H](N)CCCNC(=N)N ; "and" ; *C(=O)[C@H](N)CCCNC(=N)N]

wherein at least 25% of $R^1$ substituents are H, at least 1% of $R^1$ substituents are acetyl, and at least 4-30% of $R^1$ substituents are a group of formula (II), the molecular weight of the derivatized chitosan is between 10,000 and 150,000 Da, and the polydispersity index (PDI) of the derivatized chitosan is between 1.5 and 2.5, wherein, upon administration, the composition disrupts a preformed biofilm in the respiratory system of the subject and reduces the viscosity of viscous sputum in the subject relative to sputum that has not been contacted with the composition.

2. The method of claim 1, wherein the method comprises increasing the pourability of sputum compared to the sputum that has not been contacted with the composition.

3. The method of claim 1, wherein the method comprises reducing the viscosity of the sputum by at least 50% compared to the sputum that has not been contacted with the composition.

4. The method of claim 1, further comprising administering an antibiotic, anti-inflammatory, or mucolytic compound to the subject in conjunction with, prior to, or subsequent to the administration of the composition.

5. The method of claim 1, wherein the derivatized chitosan is present in the composition at a concentration of about 10 to 250 μg/mL.

6. The method of claim 1, wherein the molecular weight of the derivatized chitosan is between 15,000 and 100,000 Da.

7. The method of claim 1, wherein the chitosan is functionalized at between 20% and 30%.

8. The method of claim 1, wherein the degree of deacetylation (% DDA) of the derivatized chitosan is between 75% and 95%.

9. The method of claim 1, wherein the polydispersity index (PDI) of the derivatized chitosan is between 1.5 and 2.3.

10. The method of claim 1, wherein the polydispersity index (PDI) of the derivatized chitosan is between 1.5 and 2.0.

11. The method of claim 1, wherein the therapeutically effective amount is from about 5 to 500 μg/mL.

12. The method of claim 1, wherein the method comprises reducing the viscosity of the sputum by at least 80% compared to the sputum that has not been contacted with the composition.

13. A method of reducing the viscosity of viscous sputum in the respiratory system of a human subject having cystic fibrosis, the method comprising:
    administering to the subject by inhalation a therapeutically effective amount of a composition comprising a derivatized chitosan, wherein the derivatized chitosan comprises a chitosan of the following formula (I):

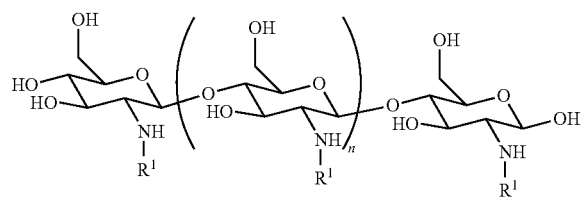

formula (I)

wherein:
n is an integer between 20 and 6000; and
each $R^1$ is independently selected for each occurrence from hydrogen, acetyl, and a group of formula (II):
wherein, formula (II) is selected from

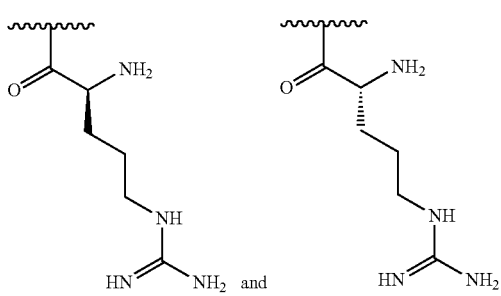 [SMILES: *C(=O)[C@@H](N)CCCNC(=N)N ; "and" ; *C(=O)[C@H](N)CCCNC(=N)N]

wherein at least 25% of $R^1$ substituents are H, at least 1% of $R^1$ substituents are acetyl, and at least 4-30% of $R^1$ substituents are a group of formula (II), the molecular weight of the derivatized chitosan is between 10,000 and 150,000 Da, wherein, upon administration, the composition disrupts a preformed biofilm in the respiratory system of the subject and reduces the viscosity of viscous sputum in the subject by at least 50% relative to the sputum that has not been contacted with the composition.

14. The method of claim 13, wherein the method comprises reducing the viscosity of the sputum by at least 80% compared to the sputum that has not been contacted with the composition.

15. The method of claim 13, wherein the molecular weight of the derivatized chitosan is between 15,000 and 100,000 Da.

16. The method of claim 13, wherein the chitosan is functionalized at between 20% and 30%.

17. The method of claim 13, wherein the degree of deacetylation (% DDA) of the derivatized chitosan is between 75% and 95%.

18. The method of claim 13, wherein the therapeutically effective amount is from about 5 to 500 µg/mL.

* * * * *